US008017326B2

(12) United States Patent
Jan et al.

(10) Patent No.: US 8,017,326 B2
(45) Date of Patent: Sep. 13, 2011

(54) METHODS OF MODULATING CELL DEATH BASED ON THE BIT-1/AES REGULATORY PATHWAY

(75) Inventors: Yiwen Jan, San Diego, CA (US); Michelle Matter, Martinsville, NJ (US); Jih-Tung Pai, San Diego, CA (US); Erkki Ruoslahti, San Diego, CA (US)

(73) Assignee: Sanford-Burnham Medical Research Institute, La Jolla, CA (US)

( * ) Notice: Subject to any disclaimer, the term of this patent is extended or adjusted under 35 U.S.C. 154(b) by 395 days.

(21) Appl. No.: 12/135,068

(22) Filed: Jun. 6, 2008

(65) Prior Publication Data

US 2009/0022711 A1 Jan. 22, 2009

Related U.S. Application Data

(62) Division of application No. 10/655,755, filed on Sep. 5, 2003, now Pat. No. 7,393,653.

(60) Provisional application No. 60/509,052, filed on Sep. 6, 2002.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| 6,132,973 A | 10/2000 | Lal et al. |
| 7,393,653 B2 | 7/2008 | Jan et al. |

FOREIGN PATENT DOCUMENTS

| WO | WO 98/010795 | 3/1998 |
| WO | WO 98/021328 | 5/1998 |

OTHER PUBLICATIONS

Zacharchuk et al. Programmed T lymphocyte death. Cell activation- and steroid-induced pathways are mutually antagonistic. J Immunol. Dec. 15, 1990;145(12):4037-45.*
Alouani, "Scintillation promximity binding assay," *Methods Mol. Biol.* 138:135-141 (2000).
Aoudjit and Vuori, "Matrix attachment regulates FAS-induced apoptosis in endothelial cells: a role for c-flip and implications for anoikis," *J. Cell Biol.* 152:633-643 (2001).
Arap et al., "Cancer treatment by targeted drug delivery to tumor vaculature in a mouse model," *Science* 279:377-380 (1998).
Arap et al., "Chemotherapy targeted to tumor vasculature," *Curr. Opin. Oncol.* 10:560-565 (1998).
Chen and Courey, "Groucho/TLE family proteins and transcriptional repression," *Gene* 249:1-16 (2000).
Daugas et al., "Apoptosis-inducing factor (AIF): a ubiquitous mitochondrial oxidoreductase involved in apoptosis," *FEBS Lett.* 476:118-123 (2000).

Degterev et al., "Identification of small-molecule inhibitors of interaction between the BH3 domain and Bcl-$x_L$," *Nature Cell Biology* 3:173-182 (2001).
Fisher and Caudy, "Groucho proteins: transcriptional corepressors for specific subsets of DNA-binding transcription factors in vertebrates and invertebrates," *Genes & Dev.* 12:1931-1940 (1998).
Frisch and Ruoslahti, "Integrins and anoikis," *Curr. Opin. Cell Biol.* 9:701-706 (1997).
Frisch and Screaton, "Anoikis mechanisms," *Curr. Opin. Cell Biol.* 13:555-562 (2001).
Frisch "Evidence for function of death-receptor-related, death-domain-containing proteins in anoikis," *Curr. Biol.* 9:1047-1049 (1999).
Frisch et al., "A role for jun-N-terminal kinase in anoikis; suppression by bcl-2 and crmA," *J. Cell Biol.* 135:1377-1382 (1996).
Gomez-Manzano et al., "Transfer of E2F-1 to human glioma cells results in transcriptional up-regulation of Bcl-2," *Cancer Res.* 61:6693-6697 (2001).
Heckman et al., "A-Myb up-regulates bcl-2 through a cdx binding site in t(14;18) lymphoma cells," *J. Biol. Chem.* 275:6499-6508 (2000).
Hungerford et al., "Inhibition of pp125FAK in cultured fibroblasts results in apoptosis," *J. Cell Biol.* 135(5):1383-1390 (1996).
Jacobson et al., "Programmed cell death in animal development," *Cell* 88:347-354 (1997).
Ji et al., "CREB proteins function as positive regulators of the translocated bcl-2 allele in t(14;18) lymphomas," *J. Biol. Chem.* 271:22687-22691 (1996).
Laakkonen et al., "A tumor-homing peptide with a targeting specificity related to lymphatic vessels," *Nat. Medicine* 8:751-755 (2002).
Lai et al., "Identification of novel human genes evolutionarily conserved in *Caenorhabditis elegans* by comparative proteomics," *Genome Res.* 703-713 (2000).
Leist and Jaattela, "Four deaths and a funeral: from caspases to alternative mechanisms," *Nat. Rev. Mol. Cell Biol.* 2:589-598 (2001).
Lesault et al., "Direct regulation of BCL-2 by FLI-1 is involved in the survival of FLI-1-transformed erythroblasts," *EMBO J.* 21:694-703 (2002).
Li et al., "Endonuclease G is an apoptotic DNase when released from mitochondria," *Nature* 412:95-99 (2001).
Lockshin and Zakeri, "Caspase-independent cell deaths," *Curr. Opin. Cell Biol.* 14:727-733 (2002).
Mahajan et al., "Bcl-2 and Bax interactions in mitochondria probed with green fluorescent protein and fluorescence resonance energy transfer," *Nat. Biotechnol.* 16:547-552 (1998).

(Continued)

*Primary Examiner* — Daniel E Kolker
*Assistant Examiner* — Gregory S Emch
(74) *Attorney, Agent, or Firm* — Jones Day

(57) ABSTRACT

The present invention provides a method of identifying an effective agent that alters the association of a Bit1 polypeptide with an AES polypeptide. The method is practiced by contacting a Bit1 polypeptide, or active fragment thereof, and an AES polypeptide, or active fragment thereof, with an agent under conditions that allow the Bit1 polypeptide or active fragment thereof to associate with the AES polypeptide or active fragment thereof; and detecting an altered association of the Bit1 polypeptide or active fragment thereof and the AES polypeptide or active fragment thereof, where an altered association indicates that the agent is an effective agent that alters the association of a Bit1 polypeptide with an AES polypeptide. Such an effective agent can modulate apoptosis and can be a useful therapeutic agent.

41 Claims, 20 Drawing Sheets

OTHER PUBLICATIONS

Mallo et al., "Protein characterization and targeted disruption of Grg, a mouse gene related to the groucho transcript of the *Drosophila* Enhancer of split complex," *Dev. Dyn.* 204:338-374 (1995).

Matter and Ruoslahti, "A signaling pathway from the α5β1 and αvβ3 integrins that elevates bcl-2 transcription," *J. Biol. Chem.* 276:27757-27763 (2001).

Mickle et al., "Genotype-phenotype relationships in cystic fibrosis," *Med. Clin. North Am.* 84(3):597-607 (2000).

Miyasaka et al., "Molecular cloning and expression of mouse and human cDNA encoding AES and ESG proteins with strong similarity to *Drosophila* enhancer of split groucho protein," *Eur. J. Biochem.* 216:343-352 (1993).

O'Brien et al., "Expression of the integrin α5 subunit in HT29 colon carcinoma cells suppresses apoptosis triggered by serum deprivation," *Exp. Cell Res.* 224:208-213 (1996).

Porkka et al., "A fragment of the HMGN2 protein homes to the nuclei of tumor cells and tumor endothelial cells in vivo," *Proc. Natl. Acad. Sci. USA* 99:7444-7449 (2002).

Ren et al., "PRDI-BF1/Blimp-1 repression is mediated by corepressors of the Groucho family of proteins," *Genes Dev.* 13:125-137 (1999).

Roose et al., "The Xenopus Wnt effector XTcf-3 interacts with Groucho-related transcriptional repressors," *Nature* 395:608-612 (1998).

Rosas-Sandoval et al., "Orthologs of a novel archaeal and of the bacterial peptidyl-tRNA hydrolase are nonessential in yeast," *Proc. Natl. Acad. Sci. USA* 99:16707-16712 (2002).

Rosen et al., "Cell detachment triggers p38 mitogen-activated protein kinase-dependent overexpression of FAS ligand. A novel mechanism of Anoikis of intestinal epithelial cells," *J. Biol. Chem.* 277:46123-46130 (2002).

Ruoslahti and Rajotte, "An address system in the vasculature of normal tissues and tumors," *Annual Rev. Immunol.* 18:813-827 (2000).

Rytomaa et al., "Involvement of FADD and caspase-8 signalling in detachment-induced apoptosis," *Curr. Biol.* 9:1043-1046 (1999).

Thomas (Ed), Tabers Cyclopedic Medical Dictionary (15th edition), Philadelphia: F.A. Davis Company, p. 870 (1985).

Van Loo et al., "Endonuclease G: a mitochondrial protein released in apoptosis and involved in caspase-independent DNA degradation," *Cell Death Differ.* 8:1136-1142 (2001).

Voet et al., *Biochemistry*, John Wiley & Sons, Inc., pp. 126-129 and pp. 228-234 (1990).

Wang et al., "Growth defect in Grg5 null mice is associated with reduced Ihh signaling in growth plates," *Dev. Dyn.* 224:79-89 (2002).

Wang, "The expanding role of mitochondria in apoptosis," *Genes Dev.* 15:2922-2933 (2001).

Wilson et al., "Induction of bcl-2 expression by phosphorylated CREB proteins during B-cell activation and rescue from apoptosis," *Mol. Cell Biol.* 16:5546-5556 (1996).

Wu et al., "AMID, an apoptosis-inducing factor-homologous mitochondrion-associated protein, induces caspase-independent apoptosis," *J. Biol. Chem.* 277:25617-25623 (2002).

Wu et al., "Negative regulation of bcl-2 expression by p53 in hematopoietic cells," *Oncogene* 20:240-251 (2001).

Yan et al., "Two-amino acid molecular switch in an epithelial morphogen that regulates binding to two distinct receptors," *Science*, 290:523-527 (2000).

Zhang et al., "Integrin activation by R-ras," *Cell* 85:61-69 (1996).

Zhang et al., "The α5β1 integrin supports survival of cells on fibronectin and up-regulates Bcl-2 expression," *Proc. Natl. Acad. Sci. USA* 92:6161-6165 (1995).

GenBank Accession No. AA440080, May 24, 2004.

GenBank Accession No. AA694807, May 24, 2004.

GenBank Accession No. AF151905—*Homo sapiens* CGI-147 protein mRNA, complete cds, May 25, 2004.

GenBank Accession No. CAA40914—properdin [*Homo sapiens*], Sep. 24, 2002.

GenBank Accession No. CAA50220—properdin [*Homo sapiens*], Sep. 24, 2002.

GenBank Accession No. NM_001130—*Homo sapiens* amino-terminal enhancer of split (AES), transcript variant 2, mRNA, Sep. 23, 2002.

GenBank Accession No. Q06195—GRG protein (ESP1 protein) Amino enhancer of split) (AES-1/AES-2)(GRG-5), May 25, 2004.

GenBank Accession No. S35680—AES-1 protein—mouse, May 25, 2004.

GenBank Accession No. X57946—*E.coli* plasmid origin of replication, May 25, 2004.

GenBank Accession No. Z14530, Sep. 24, 2002.

GENESEQ Database (Derwent, London, UK) Accession No. AAG01458, Dumas et al., "Gene Sequence," Sep. 6, 2000.

GENESEQ Database (Derwent, London, UK) Accession No. AAB59026, Rosen et al., "Gene Sequence," Sep. 21, 2000. See abstract.

* cited by examiner

A

C

|  | Bit-1 | AES |
|---|---|---|
|  | − + | − + |
| HSP-70 | 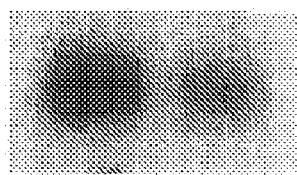 | 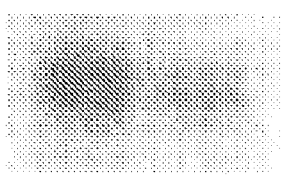 |
| GAPDH | 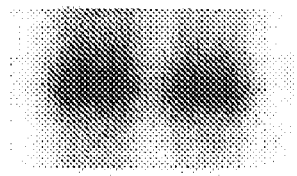 | 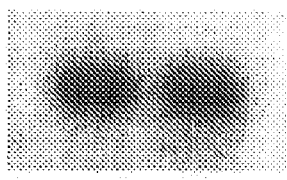 |
| Thy β4 | 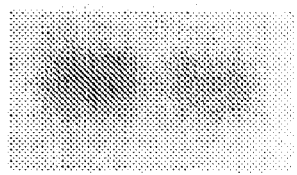 | 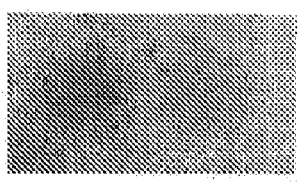 |
| GAPDH | 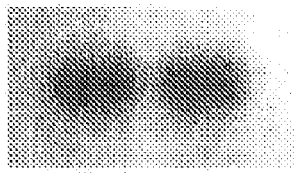 | 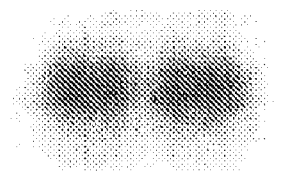 |
FIGURE 7

C
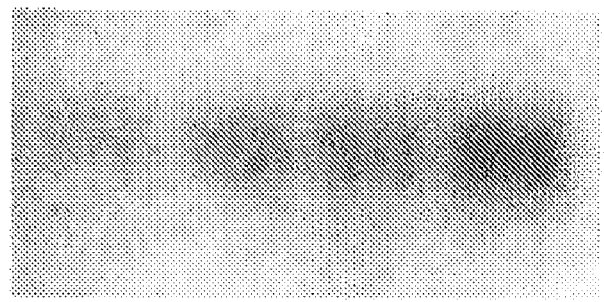
Bit-1
Actin
FIGURE 9

A

```
  1 tcgctttgtg attcttgatc cggaactttg tcacccagga accccggaag aggtagctca
 61 cgcgatagaa acgtgttcgc ttgcccagaa gaagggaagg cgcgagtgag gaaaggaggt
121 actgtagatg ccctccaaat ccttggttat ggaatatttg gctcatccca gtacactcgg
181 cttggctgtt ggagttgctt gtggcatgtg cctgggctgg agccttcgag tatgctttgg
241 gatgctcccc aaaagcaaga cgagcaagac acacacagat actgaaagtg aagcaagcat
301 cttgggagac agcggggagt acaagatgat tcttgtggtt cgaaatgact taaagatggg
361 aaaagggaaa gtggctgccc agtgctctca tgctgctgtt tcagcctaca agcagattca
421 aagaagaaat cctgaaatgc tcaaacaatg gaatactgt ggccagccca aggtggtggt
481 caaagctcct gatgaagaaa ccctgattgc attattggcc catgcaaaaa tgctgggact
541 gactgtaagt ttaattcaag atgctggacg tactcagatt gcaccaggct ctcaaactgt
601 cctagggatt gggccaggac cagcagacct aattgacaaa gtcactggtc acctaaaact
661 ttactaggtg gactttgata tgacaacaac ccctccatca caagtgtttg aagcctgtca
721 gattctaaca acaaaagctg aatttcttca cccaacttaa atgttcttga gatgaaaata
781 aaacctattc ccatgttcta aaaaaa
```

B

MPSKSLVMEYLAHPSTLGLAVGVACGMCLGWSLRVCFGMLPKSK
TSKTHTDTESEASILGDSGEYKMILVVRNDLKMGKGKVAAQCSHAAVSAYKQIQRRNP
EMLKQWEYCGQPKVVVKAPDEETLIALLAHAKMLGLTVSLIQDAGRTQIAPGSQTVLG
IGPGPADLIDKVTGHLKLY

```
   1 ggccgcccgg cgcccccagc agnccgagcc ggggcgcaca gncggggcgc agcccgcgcc
  61 ccccgccgcg attgacatga tgtttccaca aagcaggcat tcgggctcct cgcacctacc
 121 ccagcaactc aaattcacca cctcggactc ctgcgaccgc atcaaagacg aatttcagct
 181 actgcaagct cagtaccaca gcctcaagct cgaatgtgac aagttggcca gtgagaagtc
 241 agagatgcag cgtcactatg tgatgtacta cgagatgtcc tacggcttga acatcgagat
 301 gcacaaacag gctgagatcg tcaaaaggct gaacgggatt tgtgcccagg tcctgcccta
 361 cctctcccaa gagcaccagc agcaggtctt gggagccatt gagagggcca agcaggtcac
 421 cgctcccgag ctgaactcta tcatccgaca gcagctccaa gcccaccagc tgtcccagct
 481 gcaggccctg gccctgccct tgaccccact acccgtgggg ctgcagccgc cttcgctgcc
 541 ggcggtcagc gcaggcaccg gcctcctctc gctgtccgcg ctgggttccc aggcccacct
 601 ctccaaggaa gacaagaacg ggcacgatgg tgacacccac caggaggatg atggcgagaa
 661 gtcggattag caggggccg ggacagggag gttgggaggg gggacagagg ggagacagag
 721 gcacggagag aaaggaatgt ttagcacaag acacagcgga gctcgggatt ggctaatctc
 781 ccatagtatt tatggtggcg ccggcggggc cccagcccag cttgcaggcc acctctagct
 841 ttcttcctac cccattccgg cttccctcct cctccctgc agcctggtta ggtggatacc
 901 tgccctgaca tgtgaggcaa gctaaggcct ggagggtcag atgggagacc aggtcccaag
 961 ggagcaagac ctgcgaagcg cagcagcccc ggccttccc ccgttttgaa catgtgtaac
1021 cgacagtctg ccctgggcca cagccctctc accctggtac tgcatgcacg caatgctagc
1081 tgcccctttc ccgtcctggg cacccccgagt ctcccccgac cccgggtccc aggtatgctc
1141 ccacctccac ctgccccact caccacctct gctagttcca gacacctcca cgcccacctg
1201 gtcctctccc atcgcccaca aaggggggg cacgagggac gagcttagct gagctgggag
1261 gagcagggtg agggtgggcg acccaggatt ccccctcccc ttcccaaata aagatgaggg
1321 tact
```

B

```
                MMFPQSRHSGSSHLPQQLKFTTSDSCDRIKDEFQLLQAQYHSLK
LECDKLASEKSEMQRHYVMYYEMSYGLNIEMHKQAEIVKRLNGICAQVLPYLSQEHQQ
QVLGAIERAKQVTAPELNSIIRQQLQAHQLSQLQALALPLTPLPVGLQPPSLPAVSAG
TGLLSLSALGSQAHLSKEDKNGHDGDTHQEDDGEKSD
```

FIGURE 11

SEQUENCE LISTING

```
<160> NUMBER OF SEQ ID NOS: 16

<210> SEQ ID NO 1
<211> LENGTH: 806
<212> TYPE: DNA
<213> ORGANISM: Homo sapiens
<220> FEATURE:
<221> NAME/KEY: CDS
<222> LOCATION: (128)...(664)

<400> SEQUENCE: 1
tcgctttgtg attcttgatc cggaactttg tcacccagga accccggaag aggtagctca      60
cgcgatagaa acgtgttcgc ttgcccagaa gaagggaagg cgcgagtgag gaaaggaggt     120 actgtag atg ccc tcc aaa tcc ttg gtt atg gaa tat ttg gct cat ccc       169
        Met Pro Ser Lys Ser Leu Val Met Glu Tyr Leu Ala His Pro
          1               5                  10 agt aca ctc ggc ttg gct gtt gga gtt gct tgt ggc atg tgc ctg ggc       217
Ser Thr Leu Gly Leu Ala Val Gly Val Ala Cys Gly Met Cys Leu Gly
 15                  20                  25                  30 tgg agc ctt cga gta tgc ttt ggg atg ctc ccc aaa agc aag acg agc       265
Trp Ser Leu Arg Val Cys Phe Gly Met Leu Pro Lys Ser Lys Thr Ser
                 35                  40                  45 aag aca cac aca gat act gaa agt gaa gca agc atc ttg gga gac agc       313
Lys Thr His Thr Asp Thr Glu Ser Glu Ala Ser Ile Leu Gly Asp Ser
             50                  55                  60 ggg gag tac aag atg att ctt gtg gtt cga aat gac tta aag atg gga       361
Gly Glu Tyr Lys Met Ile Leu Val Val Arg Asn Asp Leu Lys Met Gly
         65                  70                  75 aaa ggg aaa gtg gct gcc cag tgc tct cat gct gct gtt tca gcc tac       409
Lys Gly Lys Val Ala Ala Gln Cys Ser His Ala Ala Val Ser Ala Tyr
     80                  85                  90
```

```
aag cag att caa aga aga aat cct gaa atg ctc aaa caa tgg gaa tac        457
Lys Gln Ile Gln Arg Arg Asn Pro Glu Met Leu Lys Gln Trp Glu Tyr
 95             100                 105                 110 tgt ggc cag ccc aag gtg gtg gtc aaa gct cct gat gaa gaa acc ctg        505
Cys Gly Gln Pro Lys Val Val Val Lys Ala Pro Asp Glu Glu Thr Leu
            115                 120                 125 att gca tta ttg gcc cat gca aaa atg ctg gga ctg act gta agt tta        553
Ile Ala Leu Leu Ala His Ala Lys Met Leu Gly Leu Thr Val Ser Leu
        130                 135                 140 att caa gat gct gga cgt act cag att gca cca ggc tct caa act gtc        601
Ile Gln Asp Ala Gly Arg Thr Gln Ile Ala Pro Gly Ser Gln Thr Val
    145                 150                 155 cta ggg att ggg cca gga cca gca gac cta att gac aaa gtc act ggt        649
Leu Gly Ile Gly Pro Gly Pro Ala Asp Leu Ile Asp Lys Val Thr Gly
160                 165                 170 cac cta aaa ctt tac taggtggact tgatatgac aacaaccct ccatcacaag          704
His Leu Lys Leu Tyr
175 tgtttgaagc ctgtcagatt ctaacaacaa aagctgaatt tcttcaccca acttaaatgt      764 tcttgagatg aaaataaaac ctattcccat gttctaaaaa aa                         806

<210> SEQ ID NO 2
<211> LENGTH: 179
<212> TYPE: PRT
<213> ORGANISM: Homo sapiens

<400> SEQUENCE: 2

Met Pro Ser Lys Ser Leu Val Met Glu Tyr Leu Ala His Pro Ser Thr
 1               5                  10                  15

Leu Gly Leu Ala Val Gly Val Ala Cys Gly Met Cys Leu Gly Trp Ser
             20                  25                  30

Leu Arg Val Cys Phe Gly Met Leu Pro Lys Ser Lys Thr Ser Lys Thr
         35                  40                  45

His Thr Asp Thr Glu Ser Glu Ala Ser Ile Leu Gly Asp Ser Gly Glu
     50                  55                  60

Tyr Lys Met Ile Leu Val Val Arg Asn Asp Leu Lys Met Gly Lys Gly
 65                  70                  75                  80

Lys Val Ala Ala Gln Cys Ser His Ala Ala Val Ser Ala Tyr Lys Gln
             85                  90                  95

Ile Gln Arg Arg Asn Pro Glu Met Leu Lys Gln Trp Glu Tyr Cys Gly
        100                 105                 110

Gln Pro Lys Val Val Lys Ala Pro Asp Glu Glu Thr Leu Ile Ala
    115                 120                 125

Leu Leu Ala His Ala Lys Met Leu Gly Leu Thr Val Ser Leu Ile Gln
130                 135                 140

Asp Ala Gly Arg Thr Gln Ile Ala Pro Gly Ser Gln Thr Val Leu Gly
145                 150                 155                 160

Ile Gly Pro Gly Pro Ala Asp Leu Ile Asp Lys Val Thr Gly His Leu
                165                 170                 175

Lys Leu Tyr

<210> SEQ ID NO 3
<211> LENGTH: 228
<212> TYPE: DNA
<213> ORGANISM: Homo sapiens
<220> FEATURE:
<221> NAME/KEY: CDS
<222> LOCATION: (1)...(228)
```

-continued

```
<400> SEQUENCE: 3 atg ccc tcc aaa tcc ttg gtt atg gaa tat ttg gct cat ccc agt aca      48
Met Pro Ser Lys Ser Leu Val Met Glu Tyr Leu Ala His Pro Ser Thr
 1               5                  10                  15 ctc ggc ttg gct gtt gga gtt gct tgt ggc atg tgc ctg ggc tgg agc      96
Leu Gly Leu Ala Val Gly Val Ala Cys Gly Met Cys Leu Gly Trp Ser
            20                  25                  30 ctt cga gta tgc ttt ggg atg ctc ccc aaa agc aag acg agc aag aca     144
Leu Arg Val Cys Phe Gly Met Leu Pro Lys Ser Lys Thr Ser Lys Thr
        35                  40                  45 cac aca gat act gaa agt gaa gca agc atc ttg gga gac agc ggg gag     192
His Thr Asp Thr Glu Ser Glu Ala Ser Ile Leu Gly Asp Ser Gly Glu
    50                  55                  60 tac aag atg att ctt gtg gtt cga aat gac tta aag                     228
Tyr Lys Met Ile Leu Val Val Arg Asn Asp Leu Lys
65                  70                  75

<210> SEQ ID NO 4
<211> LENGTH: 76
<212> TYPE: PRT
<213> ORGANISM: Homo sapiens

<400> SEQUENCE: 4

Met Pro Ser Lys Ser Leu Val Met Glu Tyr Leu Ala His Pro Ser Thr
 1               5                  10                  15

Leu Gly Leu Ala Val Gly Val Ala Cys Gly Met Cys Leu Gly Trp Ser
            20                  25                  30

Leu Arg Val Cys Phe Gly Met Leu Pro Lys Ser Lys Thr Ser Lys Thr
        35                  40                  45

His Thr Asp Thr Glu Ser Glu Ala Ser Ile Leu Gly Asp Ser Gly Glu
    50                  55                  60

Tyr Lys Met Ile Leu Val Val Arg Asn Asp Leu Lys
65                  70                  75

<210> SEQ ID NO 5
<211> LENGTH: 1324
<212> TYPE: DNA
<213> ORGANISM: Homo sapiens
<220> FEATURE:
<221> NAME/KEY: CDS
<222> LOCATION: (77)...(670)
<220> FEATURE:
<221> NAME/KEY: misc_feature
<222> LOCATION: 23, 42
<223> OTHER INFORMATION: n = A,T,C or G

<400> SEQUENCE: 5
ggccgcccgg cgcccccagc agnccgagcc ggggcgcaca gncgggcgc agcccgcgcc      60 ccccgccgcg attgac atg atg ttt cca caa agc agg cat tcg ggc tcc tcg    112
               Met Met Phe Pro Gln Ser Arg His Ser Gly Ser Ser
                 1               5                  10 cac cta ccc cag caa ctc aaa ttc acc acc tcg gac tcc tgc gac cgc     160
His Leu Pro Gln Gln Leu Lys Phe Thr Thr Ser Asp Ser Cys Asp Arg
            15                  20                  25 atc aaa gac gaa ttt cag cta ctg caa gct cag tac cac agc ctc aag     208
Ile Lys Asp Glu Phe Gln Leu Leu Gln Ala Gln Tyr His Ser Leu Lys
        30                  35                  40 ctc gaa tgt gac aag ttg gcc agt gag aag tca gag atg cag cgt cac     256
Leu Glu Cys Asp Lys Leu Ala Ser Glu Lys Ser Glu Met Gln Arg His
    45                  50                  55                  60 tat gtg atg tac tac gag atg tcc tac ggc ttg aac atc gag atg cac     304
Tyr Val Met Tyr Tyr Glu Met Ser Tyr Gly Leu Asn Ile Glu Met His
```

-continued

```
                    65                  70                  75
aaa cag gct gag atc gtc aaa agg ctg aac ggg att tgt gcc cag gtc     352
Lys Gln Ala Glu Ile Val Lys Arg Leu Asn Gly Ile Cys Ala Gln Val
            80                  85                  90 ctg ccc tac ctc tcc caa gag cac cag cag cag gtc ttg gga gcc att     400
Leu Pro Tyr Leu Ser Gln Glu His Gln Gln Gln Val Leu Gly Ala Ile
        95                  100                 105 gag agg gcc aag cag gtc acc gct ccc gag ctg aac tct atc atc cga     448
Glu Arg Ala Lys Gln Val Thr Ala Pro Glu Leu Asn Ser Ile Ile Arg
    110                 115                 120 cag cag ctc caa gcc cac cag ctg tcc cag ctg cag gcc ctg gcc ctg     496
Gln Gln Leu Gln Ala His Gln Leu Ser Gln Leu Gln Ala Leu Ala Leu
125                 130                 135                 140 ccc ttg acc cca cta ccc gtg ggg ctg cag ccg cct tcg ctg ccg gcg     544
Pro Leu Thr Pro Leu Pro Val Gly Leu Gln Pro Pro Ser Leu Pro Ala
                145                 150                 155 gtc agc gca ggc acc ggc ctc ctc tcg ctg tcc gcg ctg ggt tcc cag     592
Val Ser Ala Gly Thr Gly Leu Leu Ser Leu Ser Ala Leu Gly Ser Gln
            160                 165                 170 gcc cac ctc tcc aag gaa gac aag aac ggg cac gat ggt gac acc cac     640
Ala His Leu Ser Lys Glu Asp Lys Asn Gly His Asp Gly Asp Thr His
        175                 180                 185 cag gag gat gat ggc gag aag tcg gat tag caggggccg ggacagggag        690
Gln Glu Asp Asp Gly Glu Lys Ser Asp *
    190                 195 gttgggaggg gggacagagg ggagacagag gcacggagag aaaggaatgt ttagcacaag  750
acacagcgga gctcgggatt ggctaatctc ccatagtatt tatggtggcg ccggcggggc  810
cccagcccag cttgcaggcc acctctagct ttcttcctac cccattccgg cttccctcct  870
cctcccctgc agcctggtta ggtggatacc tgccctgaca tgtgaggcaa gctaaggcct  930
ggagggtcag atgggagacc aggtcccaag ggagcaagac ctgcgaagcg cagcagcccc  990
ggcccttccc ccgttttgaa catgtgtaac cgacagtctg ccctgggcca cagccctctc 1050
accctggtac tgcatgcacg caatgctagc tgcccctttc ccgtcctggg caccccgagt 1110
ctcccccgac cccgggtccc aggtatgctc ccacctccac ctgccccact caccacctct 1170
gctagttcca gacacctcca cgcccacctg gtcctctccc atcgcccaca aaggggggg  1230
cacgagggac gagcttagct gagctgggag gagcagggtg agggtgggcg acccaggatt 1290
cccccctcccc ttcccaaata aagatgaggg tact                             1324
```

<210> SEQ ID NO 6
<211> LENGTH: 197
<212> TYPE: PRT
<213> ORGANISM: Homo sapiens

<400> SEQUENCE: 6

```
Met Met Phe Pro Gln Ser Arg His Ser Gly Ser Ser His Leu Pro Gln
1               5                   10                  15

Gln Leu Lys Phe Thr Thr Ser Asp Ser Cys Asp Arg Ile Lys Asp Glu
            20                  25                  30

Phe Gln Leu Leu Gln Ala Gln Tyr His Ser Leu Lys Leu Glu Cys Asp
        35                  40                  45

Lys Leu Ala Ser Glu Lys Ser Glu Met Gln Arg His Tyr Val Met Tyr
    50                  55                  60

Tyr Glu Met Ser Tyr Gly Leu Asn Ile Glu Met His Lys Gln Ala Glu
65                  70                  75                  80

Ile Val Lys Arg Leu Asn Gly Ile Cys Ala Gln Val Leu Pro Tyr Leu
```

-continued

```
                    85                  90                  95
Ser Gln Glu His Gln Gln Gln Val Leu Gly Ala Ile Glu Arg Ala Lys
            100                 105                 110

Gln Val Thr Ala Pro Glu Leu Asn Ser Ile Ile Arg Gln Gln Leu Gln
        115                 120                 125

Ala His Gln Leu Ser Gln Leu Gln Ala Leu Ala Leu Pro Leu Thr Pro
    130                 135                 140

Leu Pro Val Gly Leu Gln Pro Pro Ser Leu Pro Ala Val Ser Ala Gly
145                 150                 155                 160

Thr Gly Leu Leu Ser Leu Ser Ala Leu Gly Ser Gln Ala His Leu Ser
                165                 170                 175

Lys Glu Asp Lys Asn Gly His Asp Gly Asp Thr His Gln Glu Asp Asp
            180                 185                 190

Gly Glu Lys Ser Asp
        195

<210> SEQ ID NO 7
<211> LENGTH: 147
<212> TYPE: DNA
<213> ORGANISM: Homo sapiens
<220> FEATURE:
<221> NAME/KEY: CDS
<222> LOCATION: (1)...(147)

<400> SEQUENCE: 7 atg cag cgt cac tat gtg atg tac tac gag atg tcc tac ggc ttg aac      48
Met Gln Arg His Tyr Val Met Tyr Tyr Glu Met Ser Tyr Gly Leu Asn
 1               5                  10                  15 atc gag atg cac aaa cag gct gag atc gtc aaa agg ctg aac ggg att      96
Ile Glu Met His Lys Gln Ala Glu Ile Val Lys Arg Leu Asn Gly Ile
            20                  25                  30 tgt gcc cag gtc ctg ccc tac ctc tcc caa gag cac cag cag cag gtc     144
Cys Ala Gln Val Leu Pro Tyr Leu Ser Gln Glu His Gln Gln Gln Val
        35                  40                  45 ttg                                                                 147
Leu

<210> SEQ ID NO 8
<211> LENGTH: 49
<212> TYPE: PRT
<213> ORGANISM: Homo sapiens

<400> SEQUENCE: 8

Met Gln Arg His Tyr Val Met Tyr Tyr Glu Met Ser Tyr Gly Leu Asn
 1               5                  10                  15

Ile Glu Met His Lys Gln Ala Glu Ile Val Lys Arg Leu Asn Gly Ile
            20                  25                  30

Cys Ala Gln Val Leu Pro Tyr Leu Ser Gln Glu His Gln Gln Gln Val
        35                  40                  45

Leu

<210> SEQ ID NO 9
<211> LENGTH: 32
<212> TYPE: PRT
<213> ORGANISM: Homo sapiens

<400> SEQUENCE: 9

Met Gln Arg His Tyr Val Met Tyr Tyr Glu Met Ser Tyr Gly Leu Asn
 1               5                  10                  15

Ile Glu Met His Lys Gln Ala Glu Ile Val Lys Arg Leu Asn Gly Ile
```

<210> SEQ ID NO 10
<211> LENGTH: 25
<212> TYPE: DNA
<213> ORGANISM: Homo sapiens

<400> SEQUENCE: 10
acttgtggcc cagataggca cccag                                          25

<210> SEQ ID NO 11
<211> LENGTH: 25
<212> TYPE: DNA
<213> ORGANISM: Homo sapiens

<400> SEQUENCE: 11
cgacttcgcc gagatgtcca gccag                                          25

<210> SEQ ID NO 12
<211> LENGTH: 9
<212> TYPE: PRT
<213> ORGANISM: Artificial Sequence
<220> FEATURE:
<223> OTHER INFORMATION: synthetic construct

<400> SEQUENCE: 12

Cys Asp Cys Arg Gly Asp Cys Phe Cys
 1               5

<210> SEQ ID NO 13
<211> LENGTH: 5
<212> TYPE: PRT
<213> ORGANISM: Artificial Sequence
<220> FEATURE:
<223> OTHER INFORMATION: synthetic construct

<400> SEQUENCE: 13

Cys Asn Gly Arg Cys
 1               5

<210> SEQ ID NO 14
<211> LENGTH: 6
<212> TYPE: PRT
<213> ORGANISM: Artificial Sequence
<220> FEATURE:
<223> OTHER INFORMATION: synthetic construct

<400> SEQUENCE: 14

Asn Gly Arg Ala His Ala
 1               5

<210> SEQ ID NO 15
<211> LENGTH: 13
<212> TYPE: PRT
<213> ORGANISM: Artificial Sequence
<220> FEATURE:
<223> OTHER INFORMATION: synthetic construct

<400> SEQUENCE: 15

Cys Asn Gly Arg Cys Val Ser Gly Cys Ala Gly Arg Cys
 1               5                   10

<210> SEQ ID NO 16
<211> LENGTH: 7
<212> TYPE: PRT
<213> ORGANISM: Artificial Sequence
<220> FEATURE:

```
<223> OTHER INFORMATION: synthetic construct

<400> SEQUENCE: 16

Cys Gly Ser Leu Val Arg Cys
1               5
```

METHODS OF MODULATING CELL DEATH BASED ON THE BIT-1/AES REGULATORY PATHWAY

This application is a divisional of U.S. Ser. No. 10/655,755, filed Sep. 5, 2003, now U.S. Pat. No. 7,393,653, which claims the benefit of priority of U.S. Provisional Application No. 60/509,052, filed Sep. 6, 2002, which was converted from U.S. Ser. No. 10/236,458, each of which the contents is incorporated herein by reference.

This work was supported by grants CA82713, CA79984 and CA30199 awarded by the National Cancer Institute and grant CA33000 awarded by the National. Institute of Health. The United States Government has certain rights in this invention.

BACKGROUND OF THE INVENTION

1. Field of the Invention

This invention relates generally to the fields of molecular biology and molecular medicine and, more specifically, to polypeptides involved in the regulation of apoptotic cell death.

2. Background Information

Apoptosis is the term used to describe a type of cellular death that occurs in many tissues as a normal physiological process. This form of cellular demise involves activation of a built-in genetic program for cell suicide by which cells essentially autodigest. Remnants of the dead cells are then cleared by neighboring phagocytic cells, without resulting in inflammation or scarring. Apoptosis thus stands in marked contrast to cell death caused, for example, by oxygen-deprivation in the settings of myocardial infarction or stroke, where cells lose their energy supplies, rupture and spill their contents into the extracellular milieu. This type of cell death, known as necrosis, often results in inflammation and undesirable consequences.

Apoptosis plays a role in many normal processes including tissue turnover, proper development and maintenance of the immune system, development of the nervous system, and elimination of virus-infected cells. It is a well-ordered process that is characterized by DNA fragmentation, chromatin condensation, membrane blebbing and cell shrinkage. Cells undergoing apoptosis ultimately disassemble into membrane-enclosed vesicles (apoptotic bodies) that are engulfed by neighboring cells and phagocytes, thus preventing an inflammatory response.

In contrast to the role of apoptosis in normal cellular processes, aberrantly regulated apoptotic cell death can lead to a variety of disease states and pathological conditions. As an example, dysregulation of apoptosis in the nervous system can result in unintended neuronal cell death which contributes to neurodegenerative diseases such as Alzheimer's disease, Parkinson's disease and amyotrophic lateral sclerosis (ALS). Additionally, viral infection can cause apoptosis such as T-cell apoptosis induced by the human immunodeficiency virus (HIV). The failure of normal apoptosis also can lead to disease, as in the case of autoimmune diseases in which immune cells that normally would have been eliminated through apoptosis attack normal tissues. Suppression of apoptosis can also contribute to tumorigenesis.

Integrin-mediated cell attachment is one of the main regulators of apoptosis. Most types of normal cells are anchorage-dependent; in these cells, the loss of integrin-mediated cell attachment to the extracellular matrix results in a subtype of apoptosis known as "anoikis." Integrins suppress apoptosis (anoikis) in attached cells by activating signaling pathways that promote survival and by inactivating pathways that promote apoptosis. A number of these pathways, which vary in importance in different cell types, have been partially characterized. One integrin-regulated pathway initiates with activation of focal adhesion kinase (FAK) by extracellular matrix-bound integrins and results in the activation of PI3K and Akt/protein kinase B, providing a major source of survival signaling in many cell types. This pathway may function through inactivation of the pro-apoptotic proteins Bad and caspase-9. Direct binding and activation of a caspase-8 by unliganded integrins also can contribute to anoikis, an effect which is reversed by integrin binding to the extracellular matrix.

Bcl-2 is one anti-apoptotic protein that protects cells against anoikis. The $\alpha_5\beta_1$ and $\alpha_v\beta_3$ integrins are particularly efficient in up-regulating Bcl-2 expression, whereas other integrins such as the $\alpha_v\beta_1$ integrin are ineffective. Akt activation through a FAK/Shc-Ras-PI3K pathway also can play a role in the Bcl-2-dependent survival pathway. Unfortunately, the molecules that participate in integrin regulation of Bcl-2 expression, which can be important diagnostic indicators as well as targets for therapeutic intervention, remain to be identified.

Thus, there exists a need to identify polypeptides that regulate anoikis, such as polypeptides that play a role in integrin regulation of Bcl-2 expression, as well as molecules that bind these polypeptides or modulate their interactions. The present invention satisfies this need and provides related advantages as well.

SUMMARY OF THE INVENTION

The present invention provides a method of identifying an effective agent that alters the association of a Bit1 polypeptide with an AES polypeptide. The method is practiced by contacting a Bit1 polypeptide, or active fragment thereof, and an AES polypeptide, or active fragment thereof, with an agent under conditions that allow the Bit1 polypeptide or active fragment thereof to associate with the AES polypeptide or active fragment thereof; and detecting an altered association of the Bit1 polypeptide or active fragment thereof and the AES polypeptide or active fragment thereof, where an altered association indicates that the agent is an effective agent that alters the association of a Bit1 polypeptide with an AES polypeptide. A method of the invention can be practiced in vitro or in vivo, and further can be practiced, without limitation, in a cultured cell such as a cultured mammalian or yeast cell. In one embodiment, the altered association is detected by measuring the transcriptional activity of a reporter gene.

In a method of the invention, the altered association can be an increased or decreased association. Furthermore, a variety of assays can be used to detect an altered association including, but not limited to, two-hybrid assays, co-immunoprecipitation assays, co-localization assays, scintillation proximity assays (SPA), UV and chemical cross-linking assays, biomolecular interaction analyses (BIA), mass spectrometry (MS) assays, nuclear magnetic resonance (NMR) assays, and fluorescence polarization assays (FPA). In one embodiment, a method of the invention is practiced by detecting an altered association using a yeast two-hybrid assay.

The present invention further provides a method of identifying an effective agent that modulates apoptosis by contacting a Bit1 polypeptide or fragment thereof with an agent; and determining selective binding of the agent to the Bit1 polypeptide or fragment thereof, where selective binding indicates that the agent is an effective agent that modulates apoptosis. In a method of the invention, the Bit1 polypeptide or fragment can be, for example, immobilized. If desired, the agent to be assayed can be labeled, for example, with a fluorescent label. A variety of means can be used to determine selective binding including, without limitation, fluorescence resonance energy transfer assays and competitive binding assays.

Further provided herein is a method of identifying an effective agent that modulates cell death by contacting a cell containing an exogenous nucleic acid molecule encoding a Bit1 polypeptide or active fragment thereof with an agent; and detecting altered cell death, where altered cell death indicates that the agent is an effective agent that modulates cell death. In one embodiment, the contacted cell expresses an AES polypeptide or active fragment thereof, for example, an exogenous AES polypeptide or active fragment thereof. A variety of cells are useful in the methods of the invention including, without limitation, mammalian cells. Furthermore, it is understood that a variety of assays can be useful for detecting altered cell death in a method of the invention. Assays for detecting increased or decreased cell death include yet are not limited to trypan blue exclusion assays, thymidine uptake assays, deoxytransferase-mediated (TdT) dUTP biotin nick end-labeling (TUNEL) assays, digoxygenin labeling assays, and DNA filter elution assays.

Also provided by the invention is a method for identifying an effective agent that modulates cell death that involves (a) determining an amount of Bit1 polypeptide in the cytoplasm of a cell in the presence or absence of a candidate agent, and (b) identifying an agent that modulates the amount of Bit1 polypeptide in the cytoplasm, wherein an agent that modulates the amount of Bit1 polypeptide in the cytoplasm of a cell is an effective agent that modulates cell death.

The present invention also provides a method of identifying an effective agent that modulates apoptosis by contacting a cell containing an exogenous nucleic acid molecule encoding a Bit1 polypeptide or active fragment thereof and a Bcl-2 promoter with an agent; and detecting an altered Bcl-2 level, where the altered Bcl-2 level indicates that the agent is an effective agent that modulates apoptosis. A cell useful in the invention can optionally express an AES polypeptide or active fragment thereof and, in one embodiment, expresses an exogenous AES polypeptide or active fragment thereof. In another embodiment, the altered Bcl-2 level is an increased level. In a further embodiment, the altered Bcl-2 level is a decreased level. In yet a further embodiment, the Bcl-2 promoter is operably linked to a reporter gene, which can be, without limitation, a luciferase, green fluorescent protein (GFP) or β-galactosidase (β-GAL) reporter gene.

The present invention additionally provides a method of diagnosing or predicting susceptibility to a cell accumulation disorder or a disorder of cell loss in an individual by contacting a sample from the individual with a Bit1 nucleic acid molecule; determining a test expression level of Bit1 mRNA in the sample; and comparing the test expression level to a control expression level of Bit1 mRNA, where an altered test expression level as compared to the control expression level indicates the presence of a cell accumulation disorder or a disorder of cell loss, or a predisposition thereto. In a method of the invention, the Bit1 nucleic acid molecule can include, for example, at least 10 contiguous nucleotides of SEQ ID NO:1. In one embodiment, the altered test expression level is an increased expression level that indicates the presence of a disorder of cell loss, or a predisposition thereto. As non-limiting examples, the disorder of cell can be Alzheimer's disease, Parkinson's disease, amyotrophic lateral sclerosis, retinitis pigmentosa, anemia, myocardial infarction or stroke. In another embodiment, the altered test expression level is a decreased expression level that indicates the presence of a cell accumulation disorder, or a predisposition thereto. Exemplary cell accumulation disorders include, without limitation, cancer, autoimmune disease and atherosclerosis.

Also provided herein is a method of diagnosing or predicting susceptibility to a cell accumulation disorder or a disorder of cell loss in an individual by contacting a sample from the individual with a binding agent that selectively binds a Bit1 polypeptide; determining a test expression level of Bit1 polypeptide in the sample; and comparing the test expression level to a control expression level of Bit1 polypeptide, where an altered test expression level as compared to the control expression level indicates the presence of a cell accumulation disorder or a disorder of cell loss, or a predisposition thereto. As a non-limiting example, the binding agent can be an antibody or antigen-binding fragment thereof. In one embodiment, the altered test expression level is an increased expression level that indicates the presence of a disorder of cell loss, or a predisposition thereto. Such a disorder of cell loss can be, for example, Alzheimer's disease, Parkinson's disease, amyotrophic lateral sclerosis, retinitis pigmentosa, anemia, myocardial infarction or stroke. In another embodiment, the altered test expression level is a decreased expression level that indicates the presence of a cell accumulation disorder, or a predisposition thereto, including but not limited to cancer, autoimmune disease or atherosclerosis.

The present invention further provides a method of diagnosing or predicting susceptibility to a cell accumulation disorder or a disorder of cell loss in an individual by determining a test amount of Bit1 polypeptide-AES polypeptide complex in a sample from the individual; and comparing the test amount to a control amount of Bit1 polypeptide-AES polypeptide complex, where an altered test amount as compared to the control amount indicates the presence of a cell accumulation disorder or a disorder of cell loss, or a predisposition thereto. The altered test amount can be an increased or decreased test amount. In particular embodiments, the invention is practiced to diagnose or predict susceptibility to one of the following disorders of cell loss: Alzheimer's disease, Parkinson's disease, amyotrophic lateral sclerosis, retinitis pigmentosa, anemia, myocardial infarction or stroke. In other embodiments, the invention is practiced to diagnose or predict susceptibility to one of the following cell accumulation disorders: cancer, autoimmune disease or atherosclerosis. A variety of means can be used to determine the amount of a Bit1 polypeptide-AES polypeptide complex including, for example, co-immunoprecipitation assays.

Also provided by the invention is a method of diagnosing or predicting susceptibility to a cell accumulation disorder or a disorder of cell loss in an individual that involves (a) contacting a cell or subcellular fraction thereof from the individual with a binding agent that selectively binds a Bit1 polypeptide; (b) determining a test expression level of Bit1 polypeptide in a cellular location or subcellular fraction; and (c) comparing the test expression level to a control expression level of Bit1 polypeptide in the cellular location or subcellular fraction, wherein an altered test expression level as compared to the control expression level indicates the presence of a cell accumulation disorder or a disorder of cell loss, or a predisposition thereto. In one embodiment, the cellular location or subcellular fraction is a cytoplasmic location or fraction. In another embodiment, the cellular location or subcellular fraction is a mitochondrial location or fraction.

In addition, there is provided herein a method of preventing or reducing the severity of a disorder of cell loss in a subject by administering to the subject an agent that selectively decreases Bit1 expression or activity, thereby inhibiting apoptosis in the subject. Disorders of cell loss to be treated include, without limitation, Alzheimer's disease, Parkinson's disease, amyotrophic lateral sclerosis, retinitis pigmentosa, anemia, myocardial infarction and stroke. A variety of agents that selectively decrease Bit1 expression or activity can be useful in the invention. As non-limiting examples, such agents include small molecules, nucleic acid molecules, polypeptides, peptides, peptidomimetics, and antibodies or antigen-binding fragments thereof. Any of the above agents can be optionally linked to a homing peptide such as a tumor homing peptide.

Further provided herein is a method of preventing or reducing the severity of a cell accumulation disorder in a subject by administering to the subject an agent that selectively increases Bit1 expression or activity, thereby enhancing apoptosis in the subject. A variety of cell accumulation disorders can be treated according to a method of the invention including, for example, cancer, autoimmune disease and atherosclerosis. Exemplary agents that selectively increase Bit1 expression or activity include, without limitation, small molecules, nucleic acid molecules, and polypeptides. Nucleic acid molecules useful in the invention include, but are not limited to, nucleic acid molecules encoding Bit1 or a pro-apoptotic fragment thereof. Any of the agents that selectively increase Bit1 expression or activity can be linked, if desired, to a homing molecule, which can be a homing peptide such as a tumor homing peptide.

The present invention also provides a method of inducing apoptosis in cancer cells in vivo by administering to a subject Bit1 or a pro-apoptotic fragment thereof, thereby inducing apoptosis in the cancer cells. A pro-apoptotic Bit1 fragment can be, for example, a Bit1 fragment including residues 1-76 of Bit1 or residues 27-76 of Bit1. AES or a pro-apoptotic fragment thereof can optionally also be administered to the subject.

Further provided herein is a method of inducing apoptosis in cancer cells in vivo by administering to a subject AES or a pro-apoptotic fragment thereof, thereby inducing apoptosis in the cancer cells. A method of the invention can be practiced, for example, with a pro-apoptotic AES fragment containing residues 57-105 of AES or a pro-apoptotic AES fragment containing residues 57-88 of AES.

The present invention also provides a method of selectively inducing apoptosis in cancer cells in vivo by administering to a subject a conjugate which contains a homing peptide linked to Bit1 or a pro-apoptotic fragment thereof, whereby the conjugate selectively homes to cancer cells and induces apoptosis in the cancer cells. In a method of the invention, the conjugate can include, for example, a pro-apoptotic Bit1 fragment which includes residues 1-76 of Bit1, or which includes residues 27-76 of Bit1. If desired, AES or a pro-apoptotic fragment thereof can additionally be administered to the subject.

The present invention further provides a method of inducing apoptosis in cancer cells in vivo by administering to a subject a conjugate which contains a homing peptide linked to AES or a pro-apoptotic fragment thereof, where the conjugate selectively homes to cancer cells and induces apoptosis in the cancer cells. A conjugate useful in the invention can contain, for example, a pro-apoptotic AES fragment containing residues 57-105 of AES or a pro-apoptotic AES fragment containing residues 57-88 of AES.

The present invention further provides a pro-apoptotic Bit1 fragment which includes residues 1-76 of Bit1 or a portion thereof, where the pro-apoptotic Bit1 fragment has at most 150 residues of Bit1 and has pro-apoptotic activity. In one embodiment, the pro-apoptotic Bit1 fragment includes residues 1-76 of Bit1. In further embodiments, a pro-apoptotic Bit1 fragment of the invention includes residues 1-76 of Bit1 or a portion thereof and further includes at most 100 residues, at most 76 residues or at most 50 residues of Bit1. In a further embodiment, the pro-apoptotic Bit1 consists of residues 1-76 of Bit1. In yet another embodiment, the pro-apoptotic Bit1 consists of residues 27-76 of Bit1.

The present invention further provides a pro-apoptotic AES fragment that includes residues 57-105 of AES or a portion thereof, where the pro-apoptotic fragment includes at most 150 residues of AES and has pro-apoptotic activity. In one embodiment, a pro-apoptotic AES fragment of the invention includes residues 57-105 of AES. In further embodiments, the pro-apoptotic AES fragment includes residues 57-105 of AES or a portion thereof and further includes at most 100, at most 70 or at most 50 residues of AES. In a further embodiment, the pro-apoptotic AES fragment consists of residues 57-105 of AES.

Also provided herein is a pro-apoptotic AES fragment that includes residues 57-88 of AES or a portion thereof and that includes at most 75 residues of AES, where the fragment having pro-apoptotic activity. A pro-apoptotic AES fragment of the invention can have, for example, at most 50 residues of AES, at most 40 residues of AES, or at most 35 residues of AES. In one embodiment, the pro-apoptotic AES fragment consists of residues 57-88 of AES.

BRIEF DESCRIPTION OF THE DRAWINGS

FIG. 7 shows expression of HSP-70 and thymosin β4 mRNA in cells without (−) or with (+) ecdysone to induce Bit1 (left panel) or AES (right panel) expression.

FIG. 10 shows the nucleic acid sequence (SEQ ID NO:1) and corresponding amino acid sequence (SEQ ID NO:2) of human Bit1 (Genbank accession AF151905.1; see, also, Lai et al., *Genome Res.* 10:703-713 (2000)). (A) Human Bit1 nucleic acid sequence. (B) Human Bit1 amino acid sequence.

FIG. 11 shows the nucleic acid sequence (SEQ ID NO:5) and corresponding amino acid sequence (SEQ ID NO:6) of human AES (Genbank accession NM_001130.3; see, also, Miyasaka et al., *Eur. J. Biochem.* 216:343-352 (1993)). (A) Human AES nucleic acid sequence. (B) Human AES amino acid sequence.

DETAILED DESCRIPTION OF THE INVENTION

As disclosed herein in Example I, an expression cloning strategy was used to identify regulators of Bcl-2 transcription in cells in which the integrin-Bcl-2 pathway was disabled by truncation of the α5 integrin cytoplasmic domain. Using this strategy, a clone encoding a fragment of a coding sequence was identified and designated Bit1 for Bcl-2 inhibitor of transcription.

Figure 1:
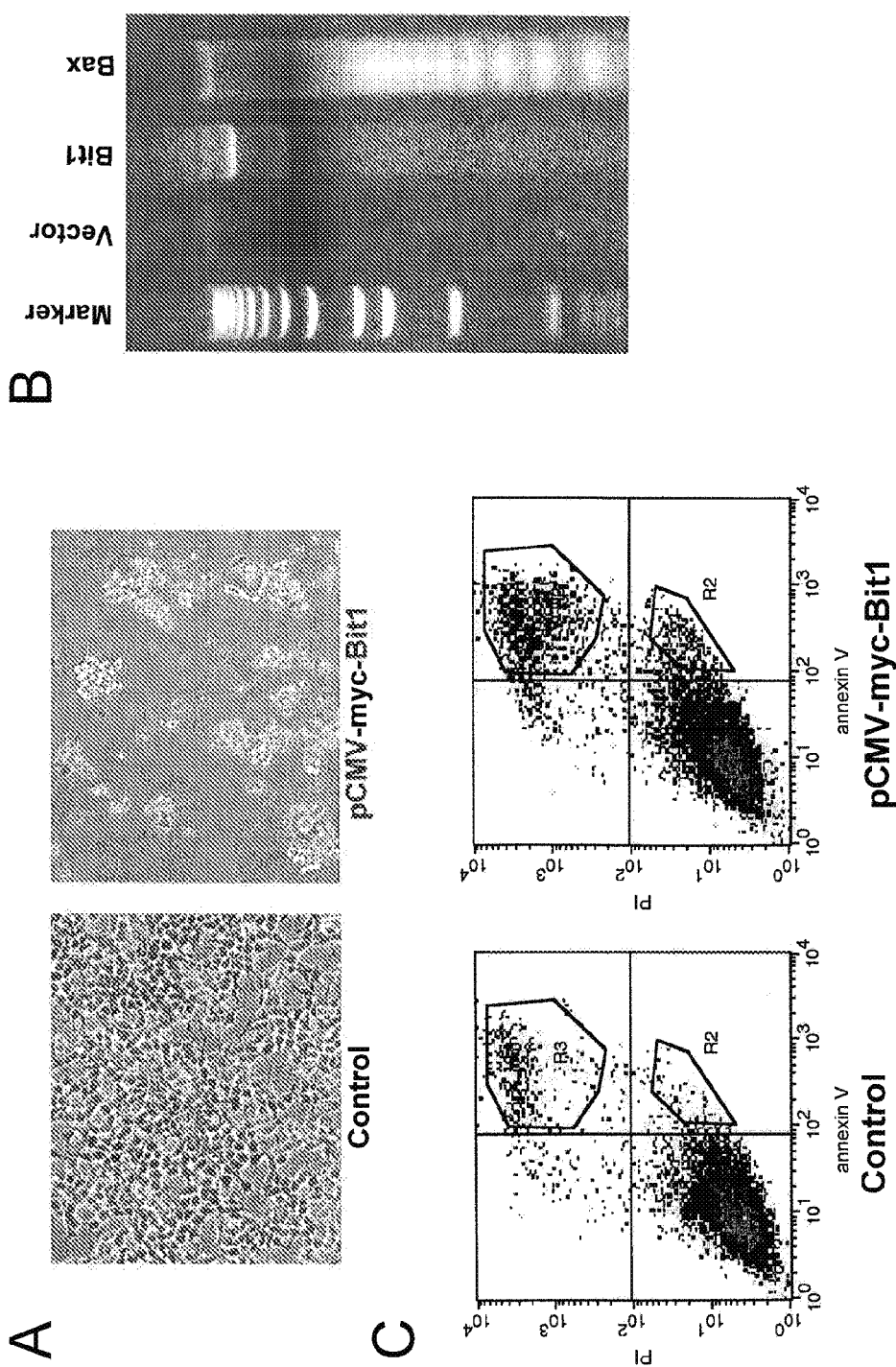
FIG. 1 shows that Bit1 induces apoptosis in HEK 293 cells. (A) HEK 293T cells round up and detach when transfected with Bit1 containing an N-terminal myc-tag, while vector (pCMV) control cells do not. (B) Agarose gel electrophoresis reveals a DNA ladder typical of apoptosis in Bit1-transfected cells. (C) Bit1 transfection increases the number of annexin V-positive cells 48 h after transfection. Shown is flow cytometric analysis of vector-transfected (left panel) and Bit1-transfected (right panel) cells.

Transfection of the full-length Bit1 clone into the human embryonic kidney cell line HEK 293 resulted in the appearance of apoptotic morphology and dramatic cell death within 48 hours (see FIG. 1A). Furthermore, as evidenced by the DNA fragmentation pattern shown in FIG. 1B, Bit1-induced cell death was apoptotic. This finding was corroborated by the increase in annexin V-positive cells observed in Bit1-transfected cultures (see FIG. 1C). Thus, Bit1 transfected cells display typical apoptotic morphology; DNA fragmentation producing a characteristic DNA ladder upon electrophoresis; and annexin V staining, which serves as an early marker for apoptosis.

As further disclosed herein, deletion analysis identified a fragment of Bit1 sufficient for apoptosis. In particular, deletion of 38 amino-terminal residues abolished Bit1 pro-apoptotic activity, while deletion of 46 carboxy-terminal residues resulted in a construct that retained pro-apoptotic activity. Furthermore, deletion of the amino-terminal seven residues of Bit1 accelerated Bit1 apoptotic activity, as did a larger carboxy-terminal deletion, indicating that the first few amino-terminal residues and the carboxy-terminal portion of Bit1 can serve as negative regulatory domains (see FIG. 2). In sum, these results indicate that full-length Bit1 inhibits transcription of the pro-survival protein Bcl-2 and induces apoptosis, while amino-terminal deletions of Bit1 can have dominant negative activity.

Figure 3:
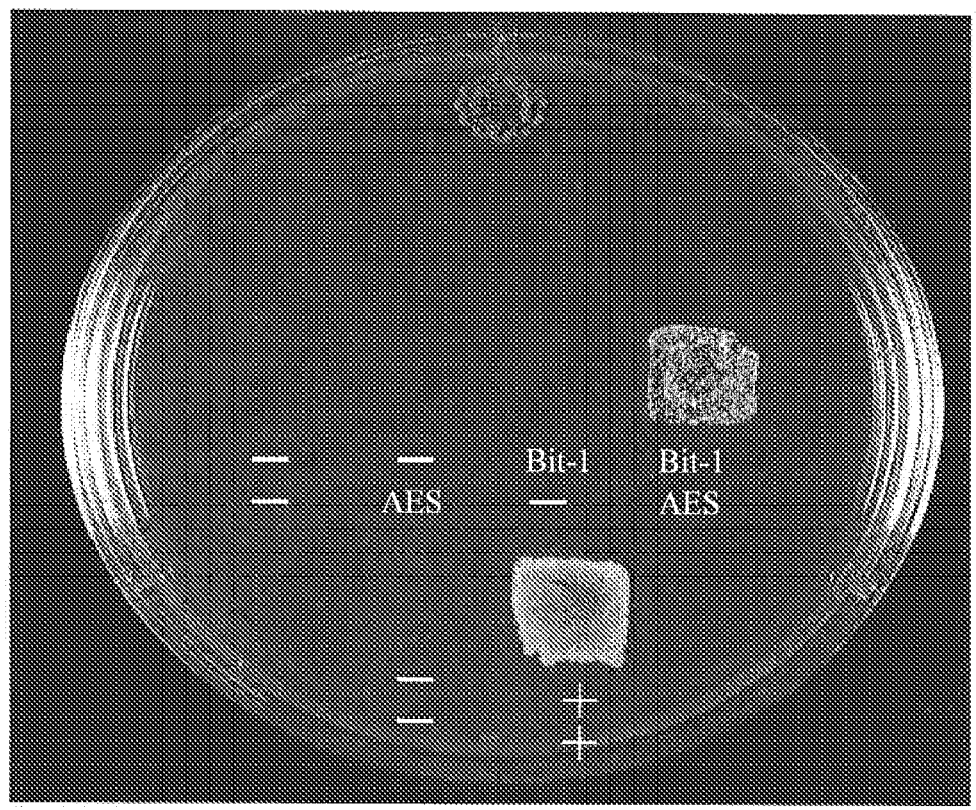
FIG. 3 shows that Bit1 interacts with AES. (A) Yeast two-hybrid analysis. (B) Co-immunoprecipitation of Bit1 and AES. (C) Interaction of endogenous Bit1 and AES. (D) Cytoplasmic Bit1 interacts with AES in cells. (E) Bit1 and AES are both required for apoptosis induction.
Figure 3:
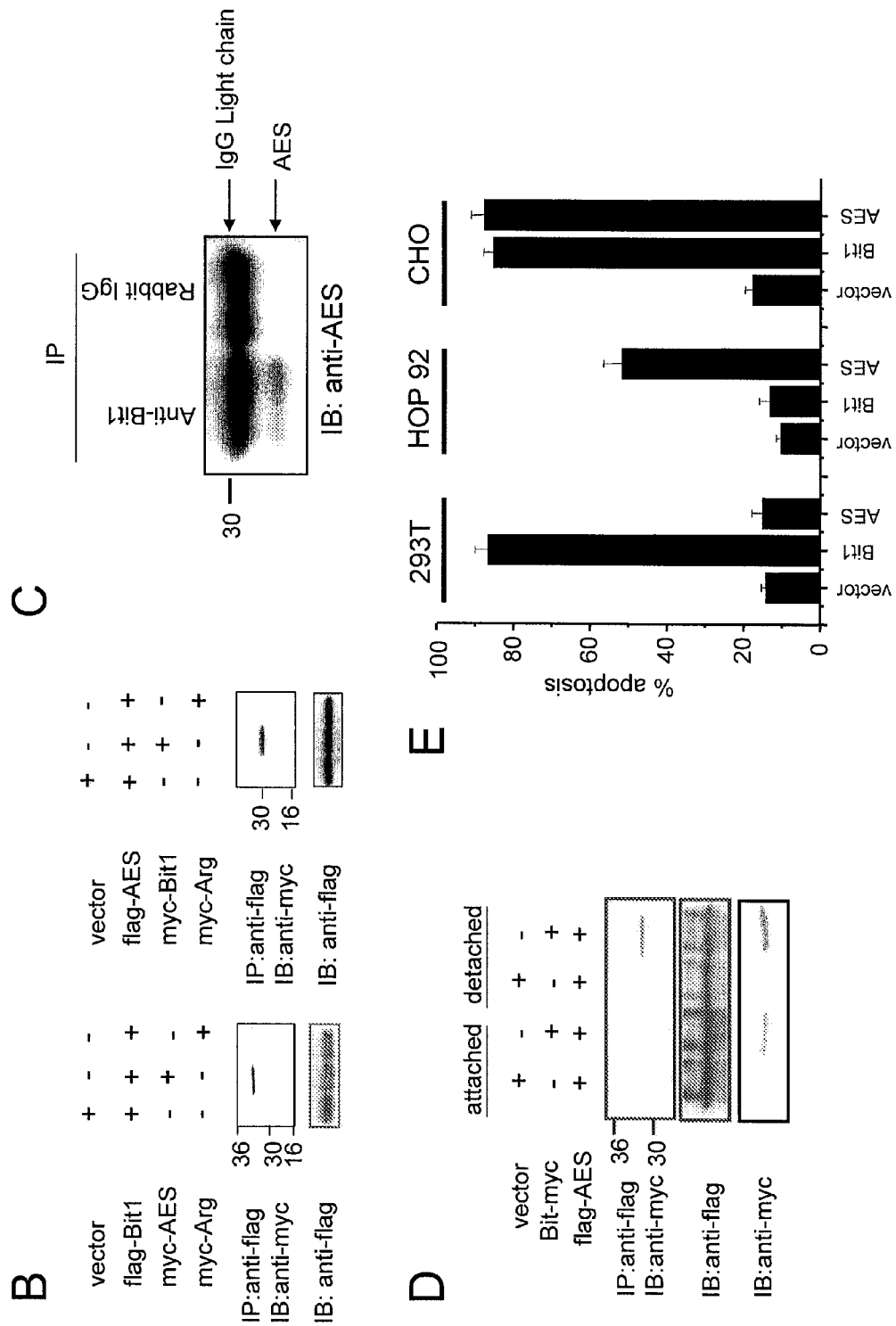

As further disclosed herein in Example II, a yeast two-hybrid screening assay was performed to identify binding partners for the Bit1 protein. Approximately thirty clones identified in the yeast two-hybrid screen encoded human AES, a developmentally regulated transcriptional co-repressor with about 50% identity to the amino-terminal region of the *Drosophila* protein Groucho (Chen and Courey, *Gene* 249:1-16 (2000); and Fisher and Caudy, *Genes Dev.* 12:1931-1940 (1998)). As shown in FIG. 3A, yeast grew when co-transformed with vectors encoding both Bit1 and AES, indicating an interaction between the two proteins. As shown in FIG. 3B, co-immunoprecipitation experiments with myc-tagged Bit1 and flag-tagged AES expressed in HEK 293 cells confirmed the ability of AES to physically interact with Bit1 in mammalian cells in vivo. FIG. 3C shows that endogenous Bit1 and AES did not detectably co-precipitate from attached HeLa cell extracts, but endogenous Bit1/AES complexes were detected when the release of Bit1 from mitochondria was initiated by culturing cells in suspension. This result indicates that Bit1 forms a complex with AES when released from the mitochondria into the cytoplasm. In addition, C-terminally tagged Bit1, which is sequestered in mitochondria, did not form complexes with AES in intact cells, but did so in suspended cells (FIG. 3C). Moreover, CHO cells, which express both Bit1 and AES, underwent apoptosis upon transfection with either protein (FIG. 3D). These results indicate that Bit1 and AES biologically interact in cells.

Figure 4:
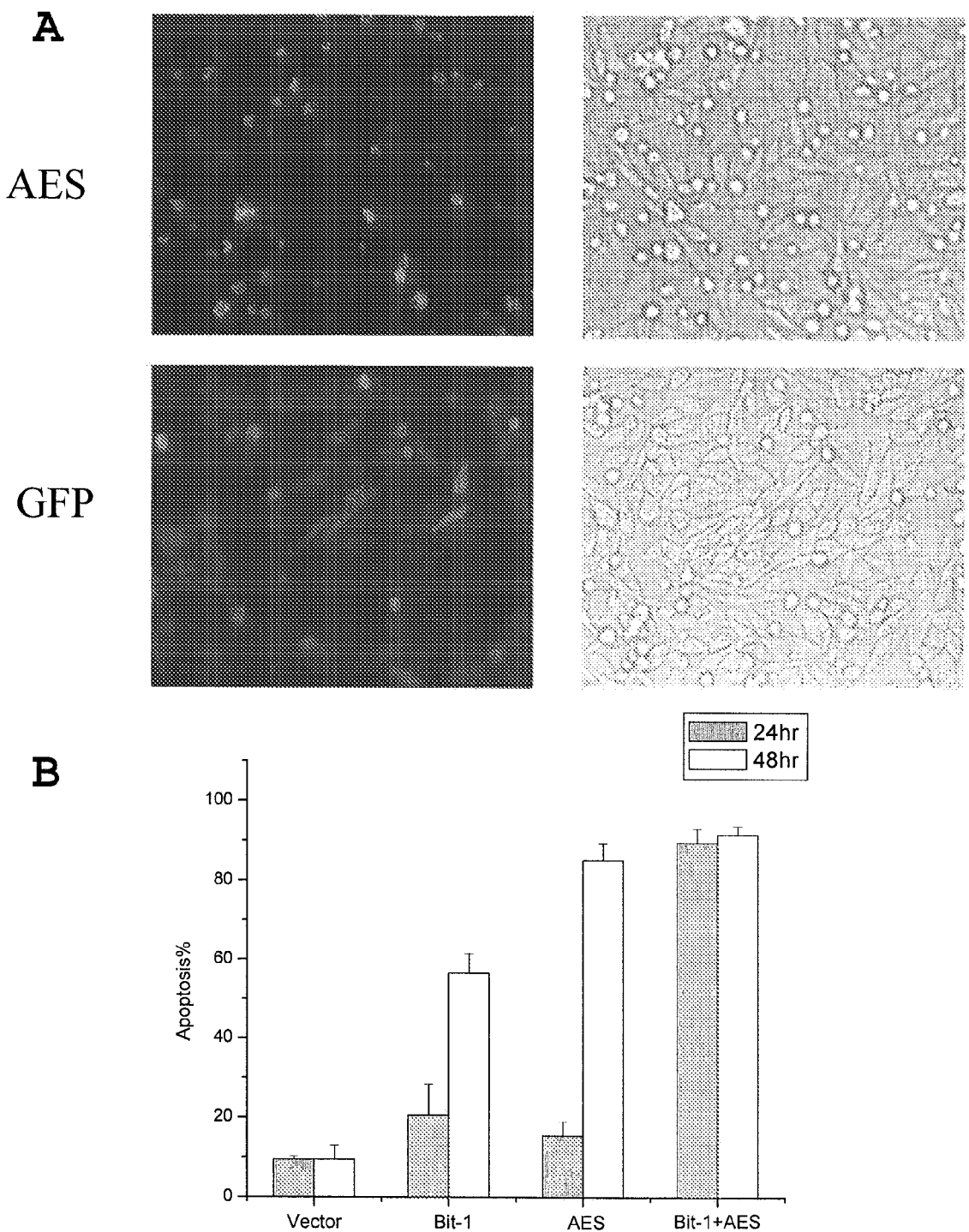
FIG. 4 shows apoptosis induced by AES transfection. (A) CHO cells transfected with AES-GFP fusion protein construct or with GFP control were examined 48 hours post-transfection. Left panels: phase contrast. Right panels: GFP fluorescence. (B) Quantification of apoptosis in cells transfected with Bit1, AES or both. Rounded up cells expressing GFP were scored as dead cells 24 and 48 hours post-transfection.

Additional results disclosed herein in Example III demonstrate that the Bit1 interacting protein, AES, can enhance Bit1-mediated apoptosis. As shown in FIG. 4A, CHO cells transfected with a green fluorescent protein (GFP)-AES fusion, as indicated by GFP fluorescence, died within 48 hours. However, in HEK 293 cells, which express no detectable Bit1 by immunohistochemistry or Northern analysis, transfection of AES alone was not apoptotic, indicating that AES pro-apoptotic activity requires co-expression of Bit1.

Figure 5:
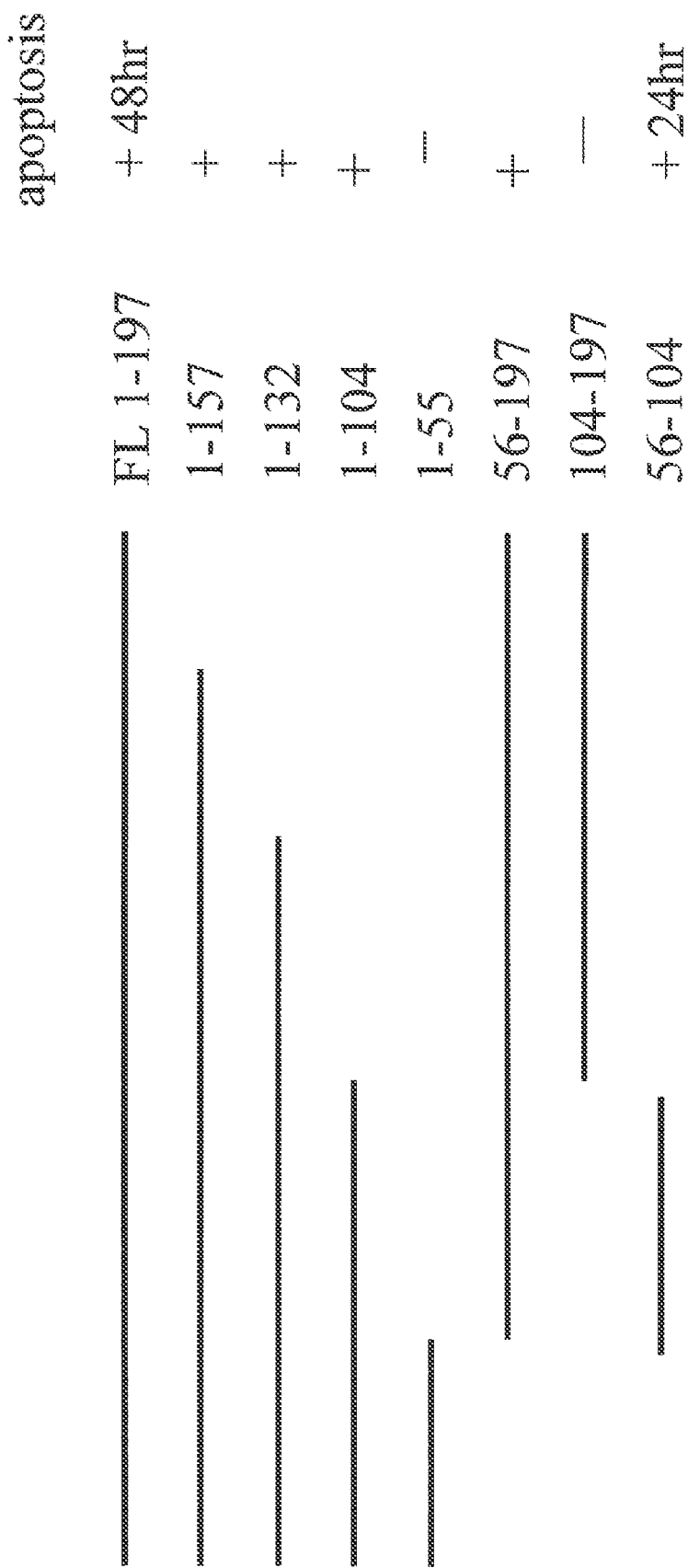
FIG. 5 shows the effect of various AES deletion mutants on apoptosis in CHO cells. A schematic of the AES construct is shown in the left column, with the AES residues present in the deletion construct indicated in the center column. Cell death (right column) was measured by trypan blue exclusion 48 hours post-transfection.

Moreover, in CHO cells co-transfected with Bit1 and AES, apoptosis was accelerated, with 100% of the doubly transfected cells dead within 24 hours. Together with the results described above, these results indicate that the pro-apoptotic protein, Bit1, down-regulates Bcl-2 expression, and binds to and acts in concert with the Groucho/TLE family transcriptional regulator, AES. The results shown in Example III also demonstrate that a construct expressing AES residues 57-105 or 57-88 efficiently induced apoptosis in CHO cells, whereas constructs including only residues 1-56 or 106-197 of AES lacked apoptotic activity. These results indicate that residues 57-105 constitute the pro-apoptotic domain of AES and that residues 57-88 are sufficient for activity (see FIG. 5).

Figure 6:
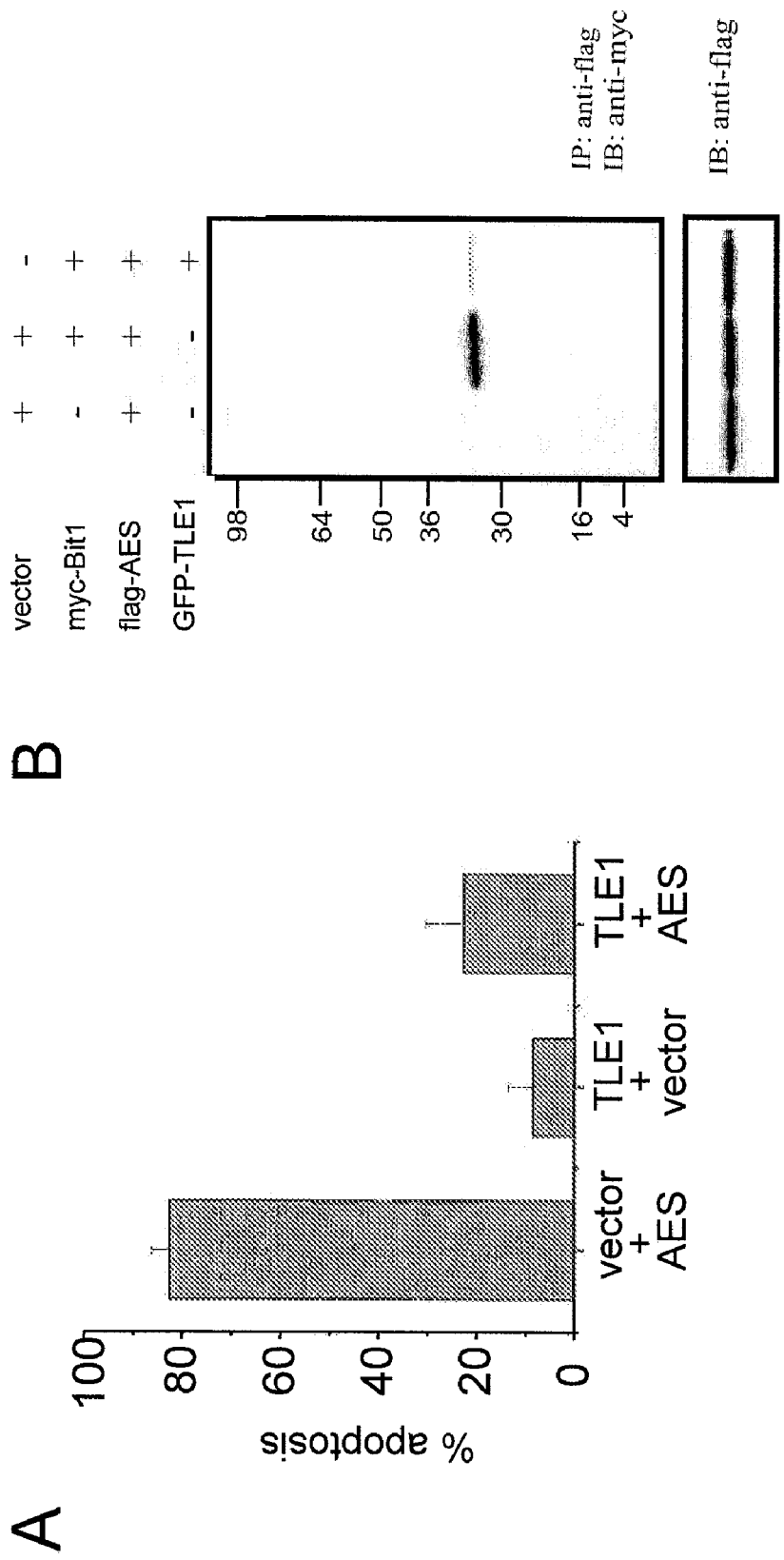
FIG. 6 shows that TLE1 suppresses AES-induced apoptosis. (A) TLE1 suppresses apoptosis induced by AES in CHO cells. (B) Reduced Bit1-AES association in HEK 293T cells transfected with TLE1. (C) Cells attached to fibronectin contain less Bit1-AES complex than cells attached to collagen. (D) TLE2 modestly suppresses apoptosis induced by AES in CHO cells.
Figure 6:
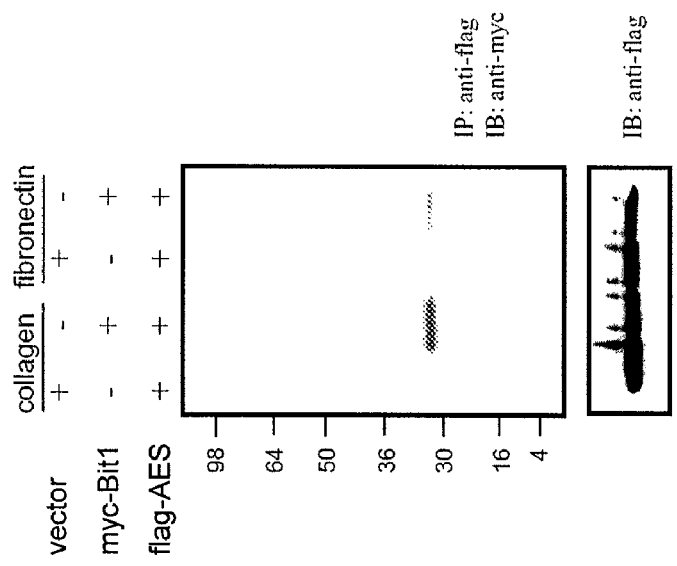
Figure 6:
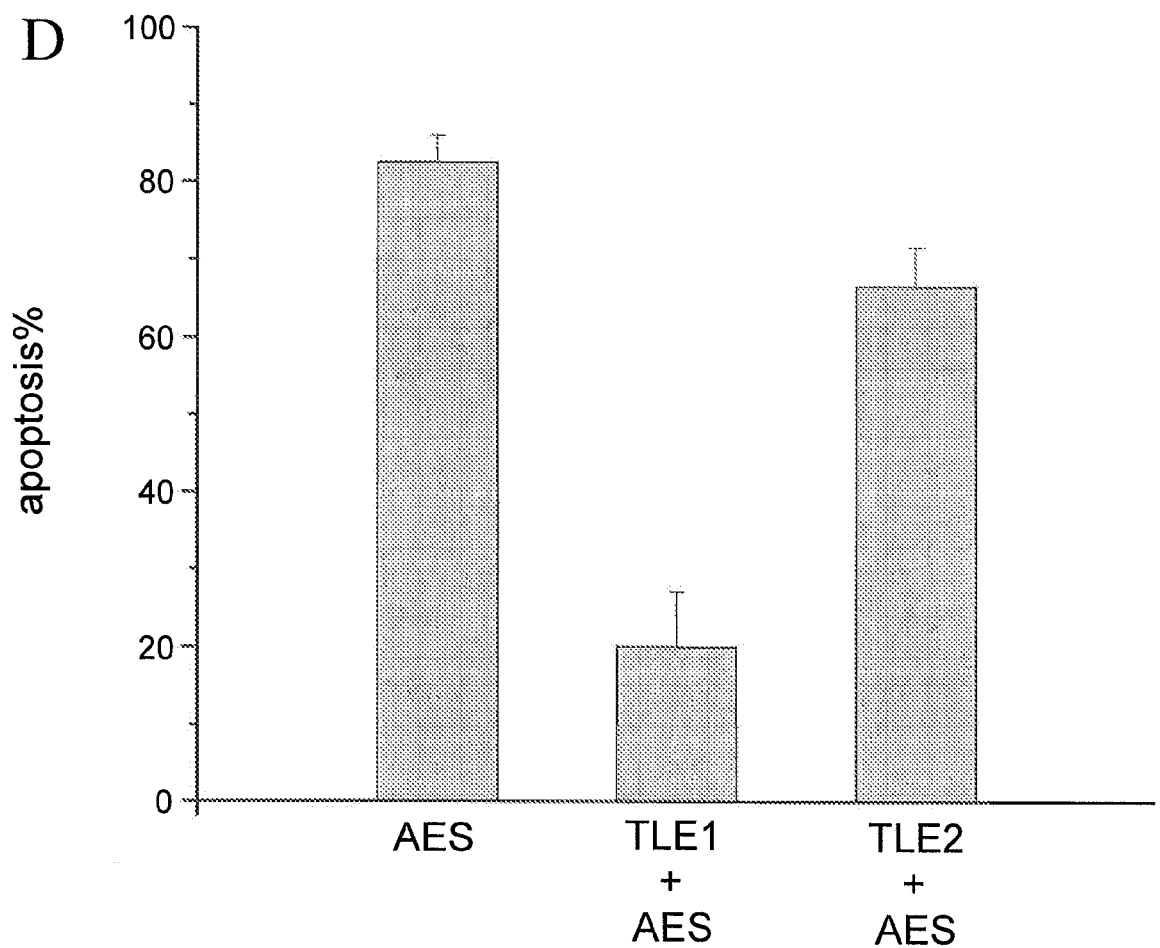

As further disclosed herein in Example IV, one of the larger TLE proteins, TLE1, was co-expressed with GFP-AES in CHO cells. As shown in FIG. 6, TLE1 blocked AES-induced cell death. TLE1 also blocked apoptosis induced by Bit1, indicating that TLE1 antagonizes apoptosis resulting from activation of the Bit1/AES pathway. Further, Bit1-AES complex formation was inhibited in cells co-expressing TLE1, as is shown in FIG. 6B. In agreement with the ability of fibronectin attachment to prevent apoptosis induced by Bit1 or AES, immunoprecipitation experiments also revealed less Bit1-AES complex in HeLa cells plated on fibronectin than on collagen (FIG. 6C). Quantification of the gel bands in FIG. 6C showed that the reduction was approximately 75%. Controls indicated that HeLa cells express higher levels of collagen receptors than of $\alpha_5\beta_1$ fibronectin receptor. Thus, a low level of the Bit1/AES complex was shown to correlate with cell survival while a high level correlated with apoptosis.

Furthermore, as disclosed herein in Example V, two stable cell lines were established expressing either Bit1 or AES under control of an ecdysone-inducible promoter to determine whether the Bit1/AES pathway can regulate the transcription of genes other than Bcl-2. In particular, probes prepared from the ecdysone-induced cell lines were used to screen microarrays representing 19,000 human cDNAs. As summarized in Table 1, two additional anti-apoptotic genes, HSP-70 and thymosin 54, were down-regulated by both Bit1 and AES, and this regulation was confirmed by Northern blotting (see FIG. 7). When Bcl-2, HSP-70 and thymosin β4 expression were restored, the pro-apoptotic effect of Bit1 was unaffected. These results indicate that the Bit1/AES pathway can regulate a wide array of pro-apoptotic genes.

The results shown herein in Example VI demonstrate that Bit1 is part of a cell-attachment regulated cell death pathway.

Figure 8:
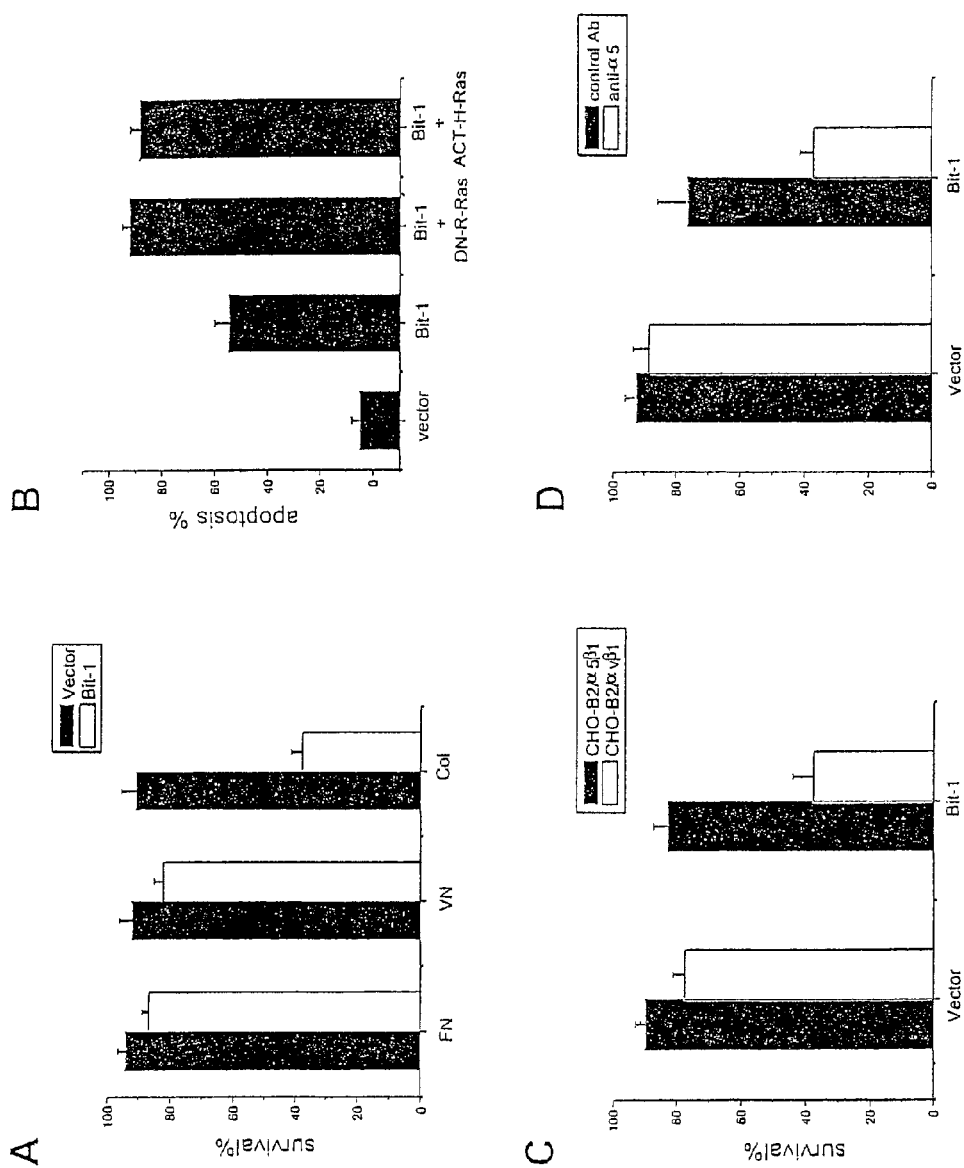
FIG. 8 shows the effect of specific extracellular matrix proteins and intracellular anti-apoptotic proteins on Bit1-induced apoptosis. (A) Effect of fibronectin (FN), vitronectin (VN) and collagen (Col) on Bit1-induced apoptosis in HEK 293 cells. Cell death was measured by trypan blue staining 48 hours post-transfection. (B) Effect of modulation of integrin activity with Ras proteins. DN-R-Ras represents dominant negative R-Ras. ACT-H-Ras represents activated H-Ras. Cell death was measured by trypan blue staining 48 hours post-transfection. (C) Expression of α5β1, but not αvβ1, suppresses Bit1-induced apoptosis. Cell survival was measured by trypan blue staining 24 hours post-transfection. (D) Function-blocking anti-α5 antibody eliminates the protective effect of fibronectin attachment. Transfected HEK 293 cells plated on fibronectin-coated wells were treated with control IgG or monoclonal anti-human α5 antibody. Cell survival was measured by trypan blue staining 24 hours post-transfection. (E) Effect of several anti-apoptotic proteins on Bit1-induced apoptosis in HEK 293 cells. Cell death was measured by trypan blue staining 48 hours post-transfection. (F) Effects of various anti-apoptotic proteins on Bit1/AES-induced apoptosis. HEK 293T cells were transfected with Bit1 or AES, along with expression vectors for the indicated proteins and assayed for cell death. (G) Cultures of HEK 293T cells plated onto bacterial culture plates coated with fibronectin (FN) or type I collagen. (H) Bit1 transfection promotes anoikis. The mean±SEM from three independent experiments is shown. P<0.05.
Figure 8:
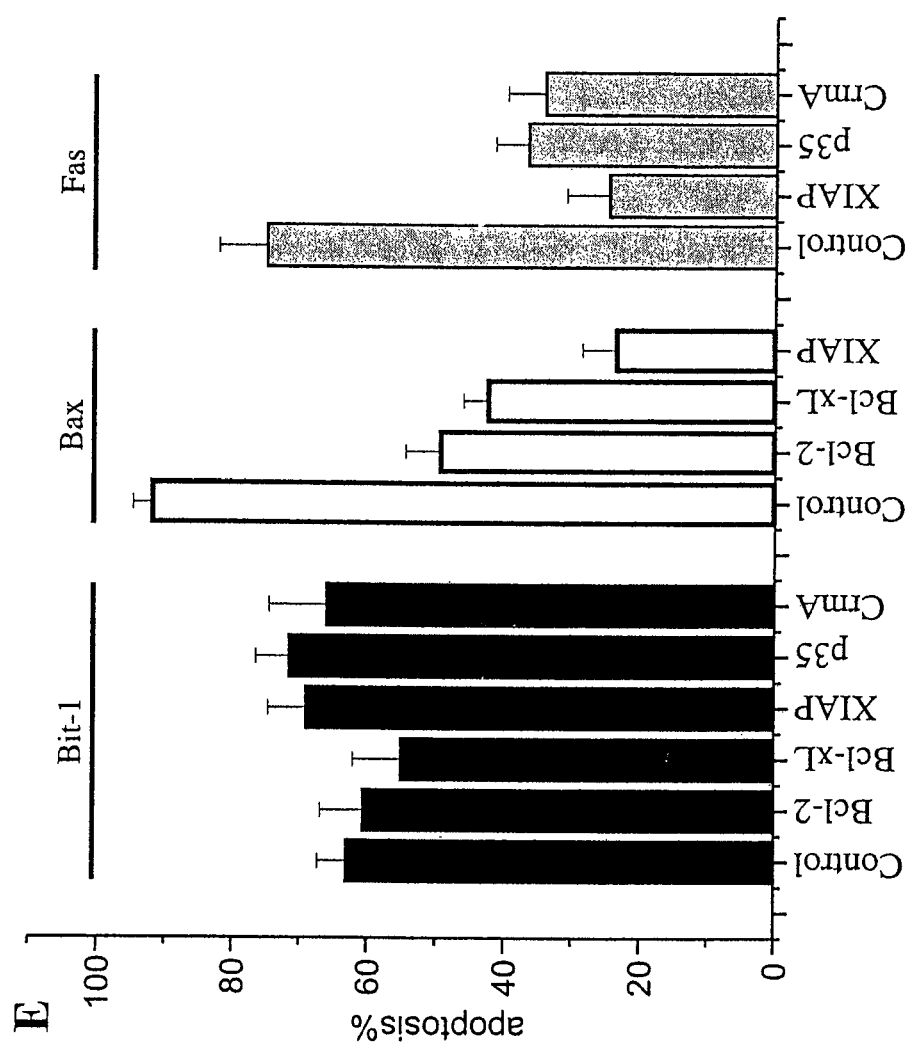
Figure 8:
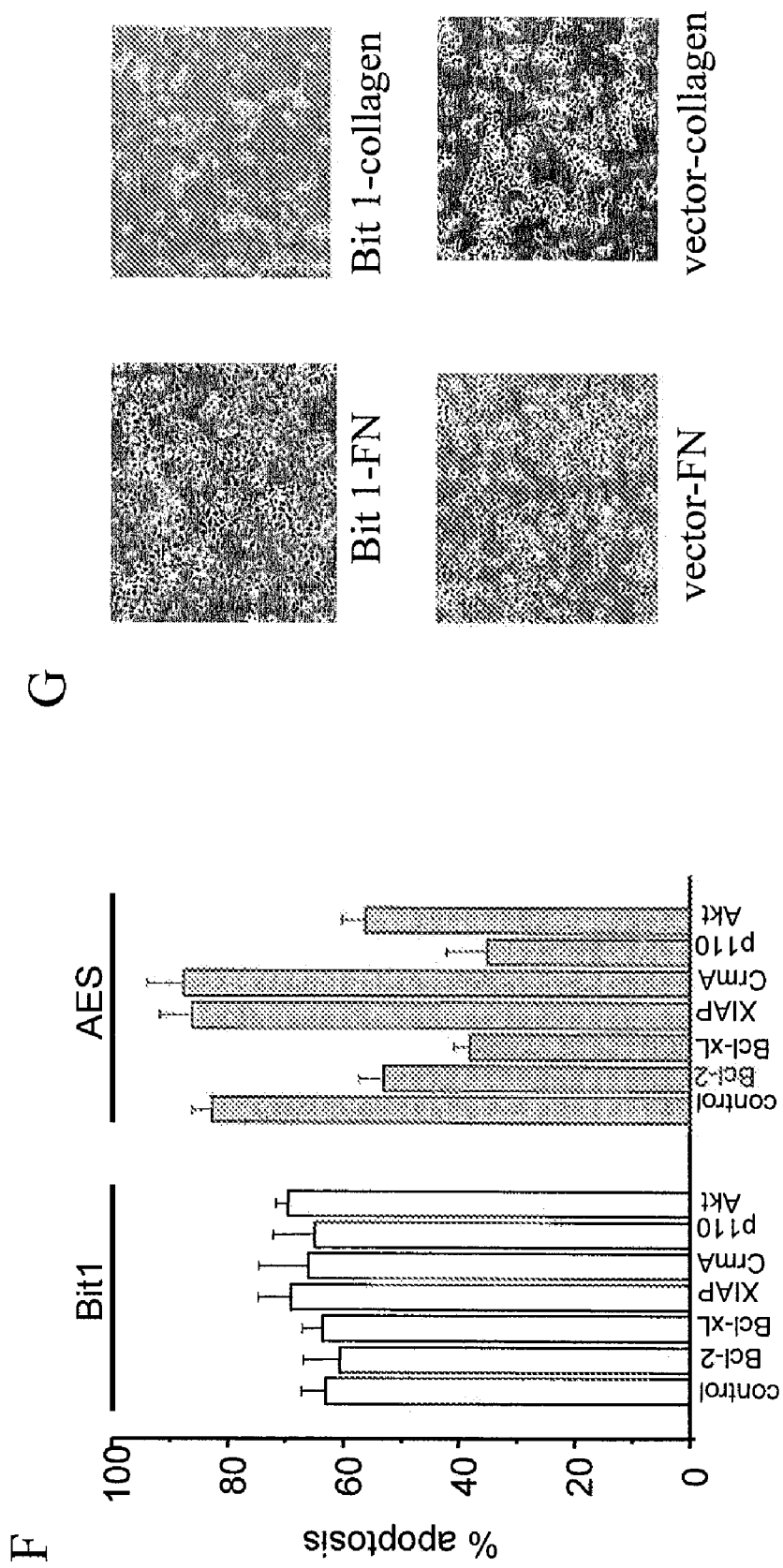
Figure 8:
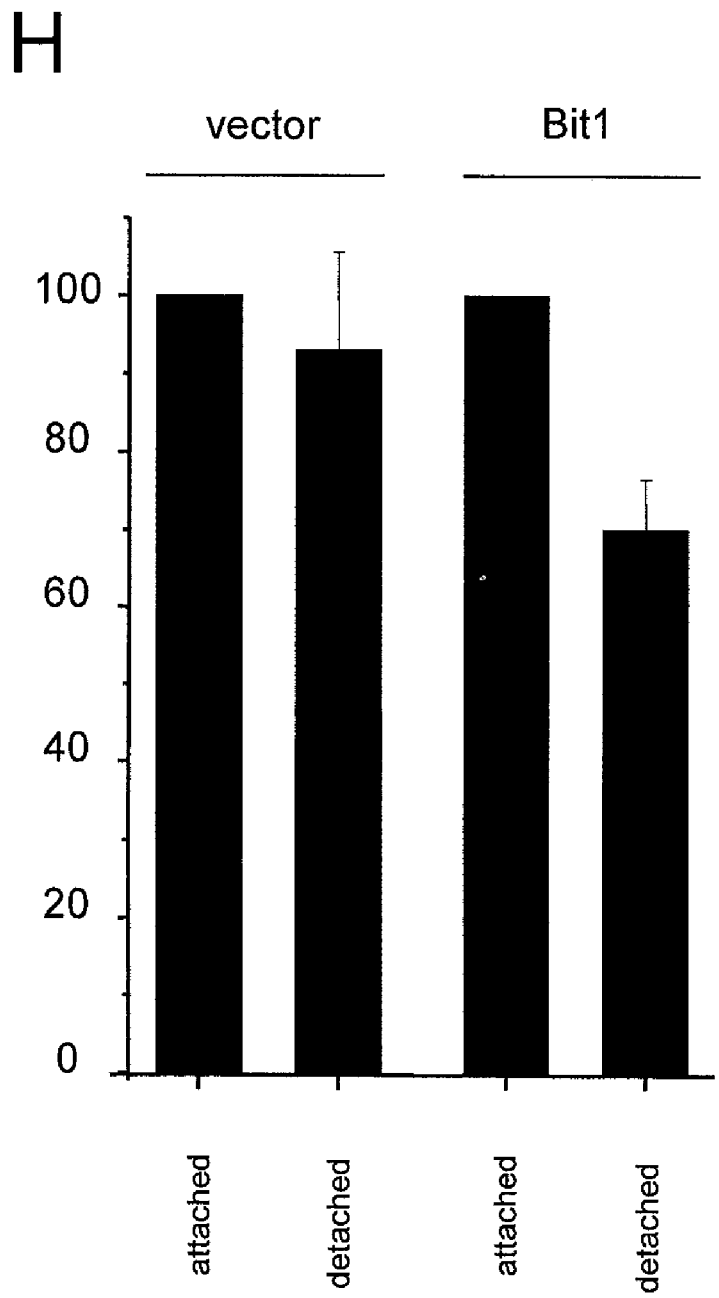

As shown in FIG. 8A, HEK 293 cells plated onto dishes coated with fibronectin (FN) or vitronectin (VN) were partially protected from Bit1-induced apoptosis, while cells plated on collagen-coated dishes were not protected. Moreover, dominant negative R-Ras and an activated form of H-Ras, both of which are negative regulators of integrin activity, each enhanced the apoptosis-inducing effect of Bit1 (see FIG. 8B) as did dominant negative FAK. As further disclosed herein, the $\alpha5\beta1$ integrin, but not $\alpha V\beta1$, suppressed Bit1-induced apoptosis (see FIG. 8C), and function blocking anti-$\alpha5\beta1$ integrin antibodies eliminated the protective effective of fibronectin attachment on Bit1-induced apoptosis in HEK 293 cells (FIG. 8D). These results demonstrate that integrin-mediated cell attachment can regulate the Bit1/AES pathway and, given the difference observed between vitronectin or fibronectin and collagen, further indicate that specific integrins are involved in this regulation.

The results shown herein in Example VI also demonstrate 293T cells transfected with a Bit1 construct that expresses mitochondrial-localized Bit1 protein had the same level of spontaneous apoptosis when grown attached to a culture dish as did control cells. However, detachment induced a higher level of cell death in the Bit1-transfected cells than in control cells. These results further demonstrate that Bit1/AES pathway plays a role in integrin-mediated cell survival (FIG. 8H).

As disclosed in Example VI, HEK 293 cells were transfected with a Bit1 expression vector together with a vector encoding an activated form of PI3K, or Bcl-2, Bcl-$X_L$ or one of several caspase inhibitors (XIAP, p35 or CrmA). None of these proteins significantly affected apoptosis induced by Bit1 in HEK 293 cells (see FIG. 8E). These results demonstrate that, among several anti-apoptotic treatments, including overexpression of Bcl-2 or caspase inhibitors, only cell attachment to fibronectin or vitronectin protected cells against Bit1-induced apoptosis. These results further indicate that the Bit1/AES pathway can play a role in anoikis.

Additional results disclosed herein in Example VII demonstrated that a single Bit1 transcript of about 1 kilobase was present in human tissues and, in particular, was prominently expressed in testis, prostate, skeletal muscle, and liver tissue, with heart, ovary, placenta and colon tissue expressing intermediate levels of Bit1. A similar expression pattern was observed for AES, with expression particularly high in the prostate and skeletal muscle, two tissues also expressing high levels of Bit1. These similar tissue distributions indicate that there can be coordinate transcriptional control of the Bit1 and AES genes and support that the physical and functional interaction of these proteins is physiologically significant. Furthermore, as discussed above, HEK 293 cells, which lack detectable endogenous Bit1, are resistant to apoptosis induced by AES. The broad expression profiles of Bit1 and AES and the Bit1 dependency of AES activity indicate that the Bit1 and AES form a apoptosis-regulating pathway which can be active in a variety of tissues and cell types.

As disclosed herein in Example VIII, Bit1 is a mitochondrial protein whose cytoplasmic expression induces cell death. Endogenous Bit1 was determined to be colocalized with a mitochondrial marker in HeLa cells (FIG. 12A). In addition, C-terminally tagged Bit1 maintained mitochondrial localization, while N-terminally tagged Bit1 had cytosolic localization, indicating that disruption of the N-terminus hinders mitochondrial localization (FIGS. 12D-G). These results are in agreement with the suggestion that eukaryotic Bit1 proteins contain a hydrophobic N-terminal sequence that could function as a mitochondrial localization signal (Rosas-Sandoval et al. *Proc. Natl. Acad. Sci. USA* 99:16707-16712 (2002)).

Thus, cytosolic Bit1 was demonstrated to induce cell death, while mitochondrial Bit1 did not have this effect unless expressed at concentrations high enough to overwhelm mitochondrial localization machinery. Also demonstrated was that culturing cells in suspension, or treating adherent cells with the pro-apoptotic compound staurosporin, caused release of Bit1 from the mitochondria to the cytoplasm. That Bit1 enters the cytoplasm to have pro-apoptotic function agrees with the disclosure herein that the pro-apoptotic activity of Bit1 correlates with the appearance of Bit1 in complexes with AES, which is a cytoplasmic and nuclear protein. Moreover, as is described in Example IX, promoter assays show that Bit1 and AES down-regulate Bcl-2 promoter activity, which is consistent with the ability of Bit1/AES to induce apoptosis.

Based on the above discoveries, the present invention provides a method of identifying an effective agent that alters the association of a Bit1 polypeptide with an AES polypeptide by contacting a Bit1 polypeptide, or active fragment thereof, and an AES polypeptide, or active fragment thereof, with an agent under conditions that allow the Bit1 polypeptide or active fragment thereof to associate with the AES polypeptide or active fragment thereof; and detecting an altered association of the Bit1 polypeptide or active fragment thereof and the AES polypeptide or active fragment thereof, where an altered association indicates that the agent is an effective agent that alters the association of a Bit1 polypeptide with an AES polypeptide. A method of the invention can be practiced in vitro or in vivo, and further can be practiced, without limitation, in a cultured cell such as a cultured mammalian or yeast cell. In one embodiment, the altered association is detected by measuring the transcriptional activity of a reporter gene.

In a method of the invention, the altered association can be an increased or decreased association. Furthermore, a variety of assays can be used to detect an altered association including, but not limited to, two-hybrid assays, co-immunoprecipitation assays, co-localization assays, scintillation proximity assays (SPA), UV and chemical crosslinking assays, biomolecular interaction analyses (BIA), mass spectrometry (MS) assays, nuclear magnetic resonance (NMR) assays, and fluorescence polarization assays (FPA). In one embodiment, a method of the invention is practiced by detecting an altered association using a yeast two-hybrid assay.

The present invention further provides a method of identifying an effective agent that modulates apoptosis by contacting a Bit1 polypeptide or fragment thereof with an agent; and determining selective binding of the agent to the Bit1 polypeptide or fragment thereof, where selective binding indicates that the agent is an effective agent that modulates apoptosis. In a method of the invention, the Bit1 polypeptide or fragment can be, for example, immobilized. If desired, the agent to be assayed can be labeled, for example, with a fluorescent label. A variety of means can be used to determine selective binding including, without limitation, fluorescence resonance energy transfer assays and competitive binding assays.

The invention additionally provides a method of identifying an effective agent that modulates apoptosis by contacting an AES polypeptide or fragment thereof with an agent; and determining selective binding of the agent to the AES polypeptide or fragment thereof, where selective binding indicates that the agent is an effective agent that modulates apoptosis. In one embodiment, the AES polypeptide or fragment is immobilized. In another embodiment, the agent to be assayed is labeled, for example, with a fluorescent label. A variety of means described herein or known in the art can be used to determine selective binding to an AES polypeptide; these means encompass but are not limited to fluorescence resonance energy transfer assays and competitive binding assays.

The screening methods of the invention can employ. Bit1 and AES polypeptides or "fragments" or "active fragments" thereof. An exemplary Bit1 polypeptide is provided herein as the human Bit1 polypeptide shown in FIG. 10 (SEQ ID NO:2). As shown herein in FIG. 10B, human Bit1 is a protein of 179 residues. As disclosed herein, Bit1 functions to down-regulate the Bcl-2 promoter and physically associates with AES. In addition, Bit1 has pro-apoptotic activity, and residues 1 to 76 or 27 to 76 of Bit1 can be sufficient for this activity. The term "Bit1," as used herein, is synonymous with "Bcl-2 inhibitor of transcription" and means a polypeptide that has substantially the amino acid sequence of naturally occurring human Bit1 or a homolog of this polypeptide and that functions to down-regulate the Bcl-2 promoter, to associate with an AES polypeptide, and that has pro-apoptotic activity. Bit1 polypeptides useful in the invention include human and other primate Bit1 polypeptides, mammalian Bit1 polypeptides such as bovine, porcine, murine and rat Bit1 polypeptides, and other vertebrate and invertebrate orthologs such as chicken, *Danio rerio, X. laevis, Drosophila* and yeast homologs. Thus, the term Bit1 encompasses species homologs, alternatively spliced forms, isotype variants and precursors of the human Bit1 sequence shown in FIG. 10. A Bit1 polypeptide generally has an amino acid sequence with at least 60% amino acid identity to the sequence of the naturally occurring human Bit1 SEQ ID NO:2 and can have, for example, 70%, 75%, 80%, 85%, 90% or 95% or more amino acid identity with SEQ ID NO:2. It is understood that a Bit1 polypeptide useful in the invention can be obtained by a variety of well known methods, including, without limitation, purification from a natural source, recombinant expression, and peptide or chemical synthesis, described further below.

Thus, a Bit1 polypeptide can be the human sequence shown in FIG. 10, or a similar, non-identical amino acid sequence that retains the ability to down-regulate the Bcl-2 promoter, to associate with an AES polypeptide and which has pro-apoptotic activity. Such a Bit1 polypeptide can have one or more amino acid additions, deletions or substitutions relative to the amino acid sequence of human Bit1, shown as SEQ ID NO:2, provided that the modifications do not substantially alter the ability of the polypeptide to down-regulate the Bcl-2 promoter, to associate with an AES polypeptide and which has pro-apoptotic activity. Therefore, it is understood that limited modifications can be made without destroying the biological function of a Bit1 polypeptide and that only a portion of the entire primary sequence can be required for activity. Genetically engineered fragments of Bit1 either alone or fused to heterologous proteins such as fusion proteins that retain measurable Bit1 biological activities also fall within the definition of the polypeptides claimed as such.

An AES polypeptide is exemplified herein as the human AES polypeptide shown in FIG. 11 (SEQ ID NO:6). As disclosed herein, human AES is a 197 residue protein that physically associates with Bit1. AES also has pro-apoptotic activity as disclosed herein, and residues 57-105 of AES display pro-apoptotic activity which is accelerated as compared to the full-length protein. The term "AES," as used herein, is synonymous with "amino enhancer of split" and means a polypeptide that has substantially the amino acid sequence of naturally occurring human AES or a homolog of this polypeptide and that functions to associate with a Bit1 polypeptide and which has pro-apoptotic activity. AES polypeptides useful in the invention include human and other primate AES polypeptides, mammalian AES polypeptides such as bovine, porcine, murine and rat AES polypeptides, and other vertebrate and invertebrate homologs such as chicken, *Danio rerio, X. laevis, Drosophila* and yeast homologs. As non-limiting examples, an AES polypeptide useful in the invention can be a human AES such as hAES1 (Genbank accession S35678) or hAES2 (Genbank accession S35680); a murine AES such as mAES1 (Genbank accession Q06195) or mAES2 (Genbank accession Q06195); an *X. laevis* AES such as xAES (Genbank accession O42470); or a *Drosophila* AES such as dAES1 (GenBank accession AA440080) or dAES2 (GenBank accession AA694807). Thus, the term AES encompasses human AES1 and AES2 as well as species homologs, alternatively spliced forms, isotype variants and precursors of the human AES sequence shown in FIG. 11. An AES polypeptide generally has an amino acid sequence with at least about 60% amino acid identity to the sequence of the naturally occurring human AES polypeptide SEQ ID NO:6 and can have, for example, 70%, 75%, 80%, 85%, 90% or 95% or more amino acid identity with SEQ ID NO:6. It is understood that an AES polypeptide useful in the invention can be obtained by well known methods such as purification from a natural source, recombinant expression and peptide or chemical synthesis.

One skilled in the art understands that an AES polypeptide can be the human sequence shown in FIG. 11, or a similar, non-identical amino acid sequence that retains the ability to associate with a Bit1 polypeptide and which has pro-apoptotic activity. Such an AES polypeptide can have one or more amino acid additions, deletions or substitutions relative to the amino acid sequence of human AES, shown as SEQ ID NO:6, provided that the modifications do not substantially alter the ability of the polypeptide to associate with a Bit1 polypeptide and which has pro-apoptotic activity. Therefore, it is understood that limited modifications can be made without destroying the biological function of an AES polypeptide and that only a portion of the entire primary sequence can be sufficient for activity. Genetically engineered fragments of AES either alone or fused to heterologous proteins such as fusion proteins that retain measurable AES biological activities also fall within the definition of the polypeptides claimed as such.

Fragments of Bit1 and AES polypeptides also can be useful in the invention. As used herein, the term "fragment" means a portion of a complete Bit1 or AES polypeptide sequence. A fragment of Bit1 or AES can have, for example, 5 or more, 6 or more, 7 or more, 8 or more, 9 or more, 10 or more, 20 or more, 30 or more, 40 or more, 50 or more 60 or more, 70 or more, 80 or more, 90 or more, or 100 or more residues. Furthermore, a fragment of Bit1 of AES can have, for example, less than 150, less than 125, less than 100, less than 90, less than 80, less than 70, less than 60, less than 50, less than 40, less than 30 or less than 20 residues.

As used herein in reference to a fragment of Bit1, the term "active fragment" means a Bit1 fragment that retains one or more, but not necessarily all, biological functions of Bit1. Thus, an active fragment of Bit1 has at least the ability to down-regulate a Bcl-2 promoter, the ability to associate with an AES polypeptide, or pro-apoptotic activity, and may have more than one or all of these activities. In the methods of the invention that comprise detecting an altered association of a Bit1 polypeptide and an AES polypeptide, it is understood that an active fragment of Bit1 retains, at least, the ability to associate with an AES polypeptide and that an active fragment of AES retains, at least, the ability to associate with a Bit1 polypeptide. Similarly, in the methods of the invention that comprise detecting altered cell death, it is understood that an active fragment of Bit1 or an active fragment of AES retains, at least, pro-apoptotic activity. In an analogous fashion, in the methods of the invention that relate to detecting an altered Bcl-2 level, it is understood that an active fragment of Bit1 retains, at least, the ability to down-regulate Bcl-2 transcription.

The screening assays disclosed herein provide a means of identifying an "effective agent," which is an agent that has activity in one of the assays disclosed herein such as an assay that relies on a Bit1 polypeptide or AES polypeptide or both. An effective agent can be an agent that alters the association of a Bit1 polypeptide with an AES polypeptide; such an agent increases or decreases the association of a Bit1 polypeptide with an AES polypeptide. An effective agent also can be an agent that selectively binds a Bit1-polypeptide, that selectively binds an AES polypeptide, or that produces altered Bcl-2 transcription. As disclosed herein, such effective agents modulate apoptosis and, thus, can be useful for therapeutic intervention in disorders resulting from inappropriate cell loss or inappropriate cell accumulation.

If desired, a collection, or library, of agents can be screened according to one of the assays disclosed herein, for example, for the ability to alter the association of a Bit1 polypeptide with an AES polypeptide, for selective binding to a Bit1 polypeptide, for selective binding to an AES polypeptide, or for the ability to alter Bcl-2 transcription. Such a library can be a diverse, random library, or can be a focused library of related agents. Where a library is screened, the component agents can be assayed individually or in pools of various sizes. As an example, several agents can be added to one well of a multi-well plate; the agents from the well generating a positive signal can be subdivided, and the agents assayed again individually or in smaller pools for the desired activity. Those skilled in the art recognize that assaying several agents at one time in a multiplexed reaction facilitates rapid testing of a large number of agents.

The size of a library to be screened in a particular assay can be determined by one skilled in the art. A library of agents can have, for example, 2 or more, 5 or more, 10 or more, 15 or more, 20 or more, 50 or more, or 100 or more different agents. In some cases, it may be desirable to screen $10^3$ or more, $10^5$ or more, $10^7$ or more, or $10^9$ or more different agents, which can be related or unrelated.

A library of agents to be screened can be, for example, a library of random polypeptides, peptides or peptidomimetics, or a library of polypeptides, peptides or peptidomimetics of interest. Such libraries encompass, without limitation, tagged chemical libraries containing polypeptide, peptide and peptidomimetic molecules. Polypeptide libraries can be generated by a variety of methodologies including, without limitation, by phage display technology. Phage display technology includes the expression of polypeptide or peptide molecules on the surface of phage as well as other methodologies by which a proteinaceous ligand is or can be associated with an encoding nucleic acid molecule. Methods for production of phage display libraries, including vectors and methods of diversifying the population of polypeptides or peptides which are expressed, are well known in the art (see, for example, Smith and Scott, *Methods Enzymol.* 217:228-257 (1993); Scott and Smith, *Science* 249:386-390 (1990); and Huse, WO 91/07141 and WO 91/07149). These and other well known methods can be used to produce a phage display library which can be screened to identify an effective agent according to one of the screening methods disclosed herein.

Several of the methods of the invention serve to identify an effective agent through an altered association of a Bit1 polypeptide with an AES polypeptide. As used herein in reference to the association of a Bit1 polypeptide and an AES polypeptide, the term "altered association" means an association that is detectably increased or decreased due to the presence of an effective agent. As a result of an altered association of a Bit1 polypeptide with an AES polypeptide in a cell, the activity of the Bit1 or AES polypeptide can be increased or decreased, thereby modulating the level of apoptosis in the cell.

One skilled in the art understands that an effective agent can function directly or indirectly and by a variety of mechanisms to alter the association of a Bit1 polypeptide with an AES polypeptide. An effective agent can function, for example, as a competitor of the binding interaction between a Bit1 polypeptide and an AES polypeptide. As an example, a peptide or peptidomimetic that mimics the structure of the AES-binding region of a Bit1 polypeptide can be an effective agent that decreases the association of a Bit1 polypeptide with an ABS polypeptide. Similarly, a peptide or peptidomimetic that mimics the structure of the Bit1-binding region of an AES polypeptide can be an effective agent that decreases the association of a Bit1 polypeptide with an AES polypeptide. A fragment of a Bit1 polypeptide or AES polypeptide also can be useful as an effective agent, providing that the fragment can alter the association of a Bit1 polypeptide and as AES polypeptide. Such agents, which can be peptides as small as about five amino acids, can be identified, for example, by screening a peptide library (see, for example, Ladner et al., U.S. Pat. No. 5,223,409) using an assay for protein-protein interactions such as one of the assays described herein below.

An effective agent also can be a molecule that binds to a Bit1 or AES polypeptide at a site distant from the site of interaction, thereby altering the three-dimensional conformation of a Bit1 or AES polypeptide such that the association of Bit1 with AES is increased or decreased. An effective agent also can produce an altered association by promoting a modification such as phosphorylation of a Bit1 or AES polypeptide. An effective agent further can act by sequestering or altering the subcellular localization of a Bit1 or AES polypeptide, thereby modulating the effective concentration of one or both polypeptides and the extent to which a Bit1 polypeptide associates with an AES polypeptide. It is understood that molecules which act by these or other direct or indirect mechanisms to increase or decrease the association of a Bit1 polypeptide with an AES polypeptide, as well as precursors of such molecules, are encompassed by the term "effective agent" as used herein.

Binding agents that selectively bind a Bit1 polypeptide or AES polypeptide can be useful in the diagnostic methods of the invention. Such binding agents bind with substantially higher affinity to the Bit1 or AES polypeptide than to an unrelated polypeptide. Useful binding agents can be, without limitation, simple or complex organic molecules, peptides, peptidomimetics, polypeptides, antibodies, nucleic acid molecules or small molecules that bind with substantially higher affinity to a Bit1 or AES polypeptide than to an unrelated polypeptide.

In the methods of the invention, the Bit1 and AES polypeptides, or fragments or active fragments thereof, can be contacted with an agent in an in vivo or in vitro environment. As used herein, the term "in vivo" means an environment within a living organism or living cell. Such a living organism can be, for example, a multi-cellular organism such as a rodent, mammal, primate or human or another animal such as an insect, worm, frog or fish, or a uni-cellular organism such as a single-celled protozoan, bacterium or yeast. Both living cells derived from an organism and used directly (primary cells) as well as cells grown for multiple generations or indefinitely in culture are encompassed within the term "in vivo" as used herein. As an example, an oocyte removed from an organism such as a frog and used directly or grown in a tissue culture dish constitutes an in vivo environment.

In vivo assays include those in which a Bit1 polypeptide or AES polypeptide or both are recombinantly expressed, for example, in a mammalian, human, murine, yeast or bacterial cell, such as an established mammalian, human, murine, yeast or cell line and including a Chinese hamster ovary (CHO) cell line or human embryonic kidney (HEK) 293 cell line. It is understood that in vivo assays can be performed with cells expressing endogenous or exogenous Bit1 polypeptide and with cells expressing endogenous or exogenous AES polypeptide. As non-limiting examples, in vivo assays can be performed with cells expressing only endogenous Bit1 and AES polypeptides; with cells expressing exogenous Bit1 and AES polypeptides; with cells expressing only endogenous Bit1 polypeptide and further expressing exogenous AES polypeptide; and with cells expressing exogenous Bit1 polypeptide and further expressing only endogenous AES polypeptide. Where an exogenous polypeptide it expressed, it is understood that it can be expressed in a cell background having no, low or high levels of the corresponding endogenous protein. In one embodiment, Bit1 is exogenously expressed in a cell that has low or undetectable levels of endogenous Bit1 polypeptide. In another embodiment, Bit1 and AES are exogenously expressed in a cell that has low or undetectable levels of endogenous Bit1 as well as endogenous AES.

In vitro assays also are useful in the methods of the invention. As used herein, the term "in vitro" means an environment outside of a living organism or cell. Assays performed, for example, in a microfuge tube, or a 96, 384 or 1536 well plate, or another assay format with purified or partially purified proteins or cellular extracts outside of a living organism are in vitro assays. Thus, assays performed using whole-cell or fractionated extracts derived from lysed cells, or performed with reconstituted systems, are encompassed within the term "in vitro" as used herein. Furthermore, assays performed in cells or tissues that have been fixed and are therefore dead, denoted in situ assays, also are encompassed within the term "in vitro" as used herein. In view of the above, it is understood that in vitro assays can utilize isolated polypeptides or whole or fractionated cell-free extracts derived, without limitation, from primary cells, transformed cells, cell lines, recombinant cells, mammalian cells, yeast cells or bacterial cells. Polypeptides useful for in vitro assays can be of recombinant origin, purified from cells or tissues, or chemically synthesized as described further below.

Conditions suitable for the association of Bit1 and AES polypeptides in vitro are described herein in Example II and further can be established empirically by well known methods. As an example, the overall charge of the polypeptides can be considered when adjusting the salt concentration or pH of a binding solution to optimize association of the polypeptides. A useful salt concentration and pH generally falls in the physiological range, for example, roughly 100 mM KCl and pH 7.0, and additional components such as glycerol or protease inhibitors can be added to the solution, for example, to inhibit polypeptide degradation. The optimal temperature for association of a Bit1 polypeptide and AES polypeptide can be determined empirically by one skilled in the art; as non-limiting examples, binding reactions can be performed on ice (4° C.), at room temperature (about 25° C.) or at body temperature (37° C.).

A variety of in vitro screening assays rely on an immobilized Bit1 or AES polypeptide such as, without limitation, an immobilized Bit1 or AES fusion protein. A polypeptide can be immobilized on any convenient solid substrate including but not limited to columns, beads, filters, plastic dishes or wells, and other materials well known in the art and further encompass solid substrates having covalently attached anti-Bit1 or anti-AES antibodies. Similarly, fusion polypeptides such as HIS-Bit1 or HIS-AES fusion polypeptides can be attached to a nickel chelate substrate through the histidine component of the fusion polypeptide (Invitrogen, Carlsbad, Calif.). Other fusion protein systems are well known in the art and commercially available, including glutathione-S-transferase (GST) fusion proteins, which can be immobilized on a glutathione affinity resin (Stratagene, La Jolla, Calif.) or using an anti-GST antibody (DAKO, Carpinteria, Calif.); "FLAG" fusion proteins, which can be immobilized on a substrate using an anti-FLAG antibody; "AU" fusion proteins, which can be immobilized on a substrate using an anti-AU antibody, commercially available from Berkeley Antibody Co., Richmond, Calif.; or Myc tag fusion proteins, which can be immobilized on a substrate using an anti-Myc antibody, commercially available from Invitrogen.

An in vitro screening assay can be performed by allowing a Bit1 polypeptide, for example, to bind to a solid substrate, then adding an AES polypeptide and an agent to be tested. Control reactions, which do not contain an agent or which contain a known negative or positive control agent, can be performed, if desired, in parallel. Incubation is performed under suitable conditions, which include, for example, an appropriate buffer concentration and pH time, and temperature. An altered association can be detected by attaching a detectable moiety such as a radionuclide or a fluorescent or antigenic label to the soluble (non-immobilized) AES polypeptide, and measuring the amount of label that is associated with the solid support. An effective agent can be identified by comparing the amount of association in the presence of an agent to a control level of association in the absence of the agent.

A variety of assays suitable for detecting an altered association or selective binding are known in the art and can be useful in the methods of the invention. Such binding assays include, without limitation, two-hybrid assays, co-immunoprecipitation assays, co-localization assays, scintillation proximity assays (SPAs), UV or chemical cross-linking assays, biomolecular interaction analysis (BIA), mass spectrometry assays (MS), nuclear magnetic resonance assays (NMR), and fluorescence polarization assays (FPA). One skilled in the art understands that such assays include low- and high-throughput assays and further encompass, without limitation, direct binding assays and competition binding assays (Yamamura et al., *Methods in Neurotransmitter Receptor Analysis*, Raven Press, New York 1990).

Assays useful in the invention for detecting an altered association of Bit1 and AES polypeptides or for detecting selective binding to a Bit1 polypeptide or AES polypeptide include transcription-based assays such as reporter assays or two-hybrid assays, for example, yeast or mammalian cell two-hybrid assays. Such transcription-based assays are well known in the art as described in standard reference texts such as Ausubel et al., supra, 1999. An example of a yeast two-hybrid assay is described herein in Example II.

Assays useful in the invention for detecting an altered association of a Bit1 polypeptide to an AES polypeptide, or for detecting selective binding to a Bit1 polypeptide or AES polypeptide, or for inhibiting the association of a Bit1 polypeptide and an AES polypeptide, or for inhibiting selective binding to a Bit1 polypeptide or AES polypeptide, further include but are not limited to, co-immunoprecipitation assays, co-localization assays, ELISA assays, and fluorescence-activated cell sorting (FACS) based assays, which are described, for example, in Harlow and Lane, Eds., *Antibodies: A Laboratory Manual*, Cold Spring Harbor Laboratory (1988). An an example, an agent such as a small molecule or polypeptide can be added to a Bit1/AES co-immunoprecipitation assay under the conditions described in Example II to detect an altered association of a Bit1 polypeptide and AES polypeptide.

High-throughput methods for identifying an effective agent according to one of the methods of the invention encompass, without limitation, scintillation proximity assays (SPA; Alouani, *Methods Mol. Biol.* 138:135-41 (2000)) and fluorescence polarization assays (FPA; Degterev et al., *Nature Cell Biology* 3:173-182 (2001)). SPA involves the use of a fluomicrosphere coated with an acceptor molecule, such as an antibody, to which a ligand can bind selectively in a reversible manner. Such an assay can be used to detect an altered association of a Bit1 polypeptide and an AES polypeptide due to an agent. As one example, an AES polypeptide can be bound to a fluomicrosphere, and the amount of light generated in the presence of a labeled Bit1 polypeptide can be measured. A candidate agent can be added to the reaction, and the amount of light generated can be measured and compared to the reaction without the agent. Similarly, a SPA assay can be used, for example to detect selective binding of an agent to a Bit1 polypeptide. As an example, human Bit1 can be bound to a fluomicrosphere using an anti-Bit1 antibody and a $^3$H or $^{125}$I-labeled agent can be added. Upon binding of the labeled agent to human Bit1, radiation energy from the labeled agent is absorbed by the fluomicrosphere, thereby producing light which is readily measured.

A fluorescence polarization assay (FPA) also can also be useful in the screening methods of the invention. As an example, a Bit1 polypeptide can be labeled with a fluorophore such as Oregon Green (Molecular Probes; Eugene, Oreg.) and can associate with an GST-AES fusion protein. After addition of an agent, displacement of fluorescent Bit1 from, for example, a GST-AES fusion protein can be measured using a spectrophotometer, for example an Analyst plate reader (LJL Biosystems), to determine whether the agent is an effective agent.

Biomolecular interaction analysis (BIA) (Weinberger et al., *Pharmacogenomics* 1:395-416 (2000)) also can be useful in the screening methods of the invention. In particular, biomolecular interaction analysis can be use to detect an altered association of a Bit1 polypeptide with an AES polypeptide or to detect selective binding to a Bit1 polypeptide or AES polypeptide. Using BIA for detection of effective agents that alter the association of a Bit1 polypeptide with an AES polypeptide, one polypeptide such as Bit1 can be bound to the chip, and the other polypeptide (AES) passed over the chip. An electrical signal is generated upon interaction of the two polypeptides. After addition of an agent, the signal is measured to determine the effect of the agent on the binding of the Bit1 polypeptide to the AES polypeptide. Similarly, for detection of selective binding, the polypeptide of interest, for example, Bit1, is bound to a BIA chip; the second component, agent, is passed over the chip. If the agent interacts with Bit1, an electrical signal is generated, thereby identifying the agent as an effective agent that selectively binds the Bit1 polypeptide. Commercially available systems for biomolecular interaction assays include surface plasmon resonance (SPR) systems such as Biacore® from Biacore (Piscataway, N.J.).

A variety of additional well known assays also can be useful in the screening methods of the invention. Such assays include mass spectrometry (MS; McLafferty et al., *Science*

284:1289-1290 (1999); and Degterev et al., *Nature Cell Biology* 3:173-182 (2001)); and nuclear magnetic resonance (NMR; Shuker et al., *Science* 274:1531-1534 (1996); Hajduk et al., *J. Med. Chem.* 42:2315-2317 (1999); and Chen and Shapiro, *Anal. Chem.* 71:669A-675A (1999)). Mass spectrometry is useful for detecting an altered association or selective binding, for example, of unlabeled polypeptides. As an example, a polypeptide such as Bit1 can be covalently attached to a SELDI chip (Ciphergen), and the binding of a second component (an agent) to immobilized Bit1 polypeptide monitored by mass spectrometry. Samples embedded in the matrix can be analyzed for mass by matrix-assisted laser desorption ionization time-of-flight (MALDI-TOF) mass spectrometry. In the same manner, NMR spectroscopy can detect an altered association of a Bit1 polypeptide with an AES polypeptide. For example $^1H/^{15}N$ HSQC spectra can be recorded by adding different amounts of an agent and an AES polypeptide to $^{15}N$-labeled $His_6$-tagged Bit1.

Virtual computational analysis also can be useful in the screening methods of the invention (see for example, Shukur et al., supra, 1996; Lengauer et al., *Current Opinions in Structural Biology* 6:402-406 (1996); Choichet et al., *Journal of Molecular Biology* 221:327-346 (1991); Cherfils et al., *Proteins* 11:271-280 (1991); Palma et al., *Proteins* 39:372-384 (2000); Eckert et al., *Cell* 99:103-115 (1999); and Loo et al., *Med. Res. Rev.* 19:307-319 (1999)). Exemplary virtual computational methodology involves virtual docking of, for example, small-molecule agents on a virtual representation of Bit1 or AES polypeptide structure. One skilled in the art understands that these and additional methods for detecting the association of two polypeptides or selective binding to a polypeptide can be useful in the screening methods of the invention.

Further provided herein is a method of identifying an effective agent that modulates cell death by contacting a cell containing an exogenous nucleic acid molecule encoding a Bit1 polypeptide or active fragment thereof with an agent; and detecting altered cell death, where altered cell death indicates that the agent is an effective agent that modulates cell death. In one embodiment, the contacted cell expresses an AES polypeptide or active fragment thereof, for example, an exogenous AES polypeptide or active fragment thereof.

The present invention also provides a method of identifying an effective agent that modulates cell death by contacting a cell containing an exogenous nucleic acid molecule encoding an AES polypeptide or active fragment thereof with an agent; and detecting altered cell death, where altered cell death indicates that the agent is an effective agent that modulates cell death. In one embodiment, the contacted cell expresses a Bit1 polypeptide or active fragment thereof, for example, an exogenous Bit1 polypeptide or active fragment thereof.

Also provided by the invention is a method for identifying an effective agent that modulates cell death that involves (a) determining an amount of Bit1 polypeptide in the cytoplasm of a cell in the presence or absence of a candidate agent, and (b) identifying an agent that modulates the amount of Bit1 polypeptide in the cytoplasm, wherein an agent that modulates the amount of Bit1 polypeptide in the cytoplasm of a cell is an effective agent that modulates cell death.

As is described herein above, Bit1 localized to the cytoplasm can function to promote apoptosis whereas Bit1 localized to the mitochondria can be inactive in promoting apoptosis. Therefore, the invention provides a method of detecting an apoptotic state of a cell. The method involves (a) determining an amount of Bit1 polypeptide in the cytoplasm of the cell; (b) comparing the determined amount of Bit1 polypeptide to a reference amount of Bit1 polypeptide indicative of a pro-apoptotic or non-apoptotic cellular state, and (c) identifying the apoptotic state of the cell.

As disclosed herein, Bit1 expressed in cell cytoplasm promotes apoptosis, while Bit1 expressed in mitochondria does not promote apoptosis. Therefore, the apoptotic state of a cell can be determined by assessing the amount of Bit1 polypeptide in the cytoplasm of a cell in comparison to a reference amount of Bit1 polypeptide. The reference amount of Bit1 polypeptide can be an amount of Bit1 polypeptide associated with a pro-apoptotic state, such as an amount of Bit1 expression greater than that observed in a reference normal non-apoptotic cell, or an amount of Bit1 expression similar to that observed in a reference pro-apoptotic cell. The reference amount of Bit1 polypeptide also can be an amount of Bit1 polypeptide associated with a non-apoptotic state, such as an amount of Bit1 expression similar to or less than that observed in a reference normal non-apoptotic cell, or less than that observed in a reference pro-apoptotic cell.

A variety of cells are useful in the methods of the invention including, without limitation, mammalian cells. It further is understood that a variety of assays can be useful for detecting altered cell death, which can be increased or decreased cell death. Such assays include yet are not limited to trypan blue exclusion assays, thymidine uptake assays, TUNEL assays, digoxygenin labeling assays, and DNA filter elution assays.

The methods of the invention for identifying an effective agent that modulates cell death are based on detecting altered cell death in a cell containing an exogenous nucleic acid molecule encoding a Bit1 polypeptide or active fragment thereof or in a cell containing an exogenous nucleic acid molecule encoding an AES polypeptide or active fragment thereof. In the screening methods of the invention, altered cell death can be determined by a variety of assays well known in the art including any assay for cell survival or for cell death, including assays which do not discriminate between apoptotic and necrotic cell death and assays that are specific for apoptotic cell death. An example of a survival assay can be to express an exogenous Bit1-encoding nucleic acid molecule in a mammalian cell line under the control of an inducible promoter such that, upon exposure to the inducing agent, cells are no longer able to grow in culture. This cell line can be aliquoted into a 96 well plate with media that contains the inducer. An agent can be added to these cells or expressed in these cells. After incubating the cells under conditions amenable for cell growth for the desired period of time, generally one to three days, the amount of cell growth can be measured by a variety of assays as an indicator of the extent of cell death. Such assays include, without limitation, optical density measurements performed using a standard spectrophotometer; uptake of dyes such as trypan blue or alomar blue; uptake of $^3H$-thymidine or any other assay of DNA replication, cell proliferation or cell viability.

The methods of the invention can be practiced, if desired, by expressing a mammalian Bit1 polypeptide such as a human Bit1 polypeptide in a yeast cell. Such a yeast strain can be constructed with a mammalian Bit1 polypeptide under the control of an inducible promoter. Expression of the mammalian Bit1 polypeptide in yeast results in yeast cell death. An agent to be assayed can be added to or expressed in this yeast stain; agents that modulate Bit1-induced apoptosis result in enhanced survival or death of yeast colonies. Yeast cell survival can be easily detected by identifying colonies on solid media or by determining the optical density of liquid yeast cultures.

Methods for determining the extent of apoptotic cell death can be useful in the screening methods of the invention and include, without limitation, light microscopy for determining the presence of one or more morphological characteristics of apoptosis such as condensed or rounded morphology, shrinking and blebbing of the cytoplasm, preservation of the structure of cellular organelles including mitochondria, and condensation and margination of chromatin. The percentage of apoptotic cells also can be determined by assaying apoptotic activity using terminal deoxytransferase-mediated (TdT) dUTP biotin nick end-labeling (TUNEL; Gavriel et al., *J. Cell Biol.* 119:493 (1992); Gorczyca et al., *Int. J. Oncol.* 1:639 (1992); Studzinski (Ed.), *Cell Growth and Apoptosis*, Oxford: Oxford University Press (1995)). ApopTag™ (ONCOR, Inc., Gaithersburg, Md.) is a commercially available kit for identification of apoptotic cells using digoxygenin labeling. In addition, the extent of apoptotic cell death can be determined by detecting characteristic nucleosomal DNA fragments using agarose gel electrophoresis (Studzinski, supra, 1995; Gong et al., *Anal. Biochem.* 218:314 (1994)) or using DNA filter elution methodology to detect apoptosis-associated DNA fragmentation-(Bertrand et al., *Drug Devel* 34:138 (1995)). One skilled in the art understands that the methods of the invention can be practiced using one of these or other routine methodologies for detection of cell death, including apoptotic and necrotic cell death.

The present invention also provides a method of identifying an effective agent that modulates apoptosis by contacting a cell containing an exogenous nucleic acid molecule encoding a Bit1 polypeptide or active fragment thereof and a Bcl-2 promoter with an agent; and detecting an altered Bcl-2 level, where the altered Bcl-2 level indicates that the agent is an effective agent that modulates apoptosis. A cell useful in the invention can optionally express an AES polypeptide or active fragment thereof and, in one embodiment, expresses an exogenous AES polypeptide or active fragment thereof. The altered Bcl-2 level can be an increased or decreased Bcl-2 level. Bcl-2 promoters useful in the invention include endogenous and exogenous promoters and encompass the P1 and P2 Bcl-2 promoters, which can be used individually or in combination. In the methods of the invention, the Bcl-2 promoter can optionally be operably linked to a reporter gene such as, without limitation, a luciferase, green fluorescent protein (GFP) or β-galactosidase (β-GAL) reporter gene.

As used herein, the term "Bcl-2 level" means the amount of Bcl-2 mRNA or encoded polypeptide. The methods of the invention for detecting an altered "Bcl-2 level" can be practiced by directly or indirectly assaying for the amount of Bcl-2 mRNA, Bcl-2 protein or Bcl-2 activity and include, but are not limited to, detection of endogenous Bcl-2 mRNA or protein, detection of an exogenous reporter gene RNA and detection of an encoded reporter gene product operably linked to a Bcl-2 promoter. As non-limiting examples, a method of the invention can be practiced by assaying for the rate of transcription at the Bcl-2 promoter, by assaying for the amount of Bcl-2 mRNA, by assaying for the amount of a reporter gene RNA linked to a Bcl-2 promoter, by assaying for the amount of Bcl-2 polypeptide, or by assaying for the amount or function of a gene product encoded by a reporter gene operably linked to a Bcl-2 promoter.

Hybridization methods can be useful for detecting Bcl-2 mRNA levels or the levels of mRNA expressed from a linked reporter gene; numerous methods are well known in the art for determining mRNA levels by specific or selective hybridization with a complementary nucleic acid probe. Such methods include solution hybridization procedures as well as solid-phase hybridization procedures in which the probe or sample is immobilized on a solid support. Specific examples of useful methods include amplification methods such as target and signal amplification methods and include the polymerase chain reaction (PCR) and reverse-transcriptase-PCR (RT-PCR); transcription-mediated amplification (Gen-Probe Incorporated; San Diego, Calif.); branched chain DNA (bDNA) amplification (Bayer Diagnostics; Emeryville, Calif.); strand displacement amplification (SDA; Becton Dickinson; Franklin Lakes, N.J.); and ligase chain reaction (LCR) amplification (Abbott Laboratories; Abbott Park, Ill.). Additional methods useful in the invention include RNase protection; nuclear run-on assays; northern analysis or other RNA blot, dot blot or membrane-based technology; dip stick; pin; or two-dimensional array immobilized onto a chip. Conditions are well known in the art for quantitative determination of mRNA levels using both solution and solid phase hybridization procedures as described, for example, in Ausubel et al., *Current Protocols in Molecular Biology* (Supplement 47), John Wiley & Sons, New York (1999).

Polymerase chain reaction (PCR) or RT-PCR can be useful in the methods of the invention. PCR or RT-PCR can be performed with isolated RNA or crude or partially fractionated samples. PCR methods are well known in the art as described, for example, in Dieffenbach and Dveksler, *PCR Primer: A Laboratory Manual*, Cold Spring Harbor Press, Plainview, N.Y. (1995). Multisample formats including two-dimensional arrays also are known in the art and offer the advantage of analyzing numerous different agents in a single assay.

Nucleic acid probes for detecting a Bcl-2 mRNA level are well known in the art. One skilled in the art can use, for example, a probe corresponding to some or all of the human Bcl-2 coding sequence available, for example, from GenBank accession P01415 (see, also, Tsujimoto and Croce, *Proc. Natl. Acad. Sci., USA* 83:5214-5218 (1986)). Similarly, a probe corresponding to some or all of the murine Bcl-2 coding sequence can be prepared from the sequence available, for example, from GenBank accession P10417 or Negrini et al., *Cell* 49:455-463 (1987). Appropriate conditions and various assay formats for detecting a Bcl-2 or reporter gene mRNA are well known in the art or can be established using routine methods. As non-limiting examples, a Bcl-2 promoter-green fluorescence protein (GFP) reporter construct can be prepared and quantitation of resulting GFP fluorescence can be performed as described, for example, in Matter and Ruoslahti, *J. Biol. Chem.* 276:27757-27763 (2001). Similarly, a Bcl-2 promoter-luciferase construct can be prepared and a luciferase assay can be performed as described, for example, in Gomez-Manzano et al., *Cancer Res.* 61:6693-6697 (2001); Wilson et al., *Mol. Cell. Biol.* 16:5546-5556 (1996); Ji et al., *J. Biol. Chem.* 271:22687-22691 (1996); and Heckman et al., *J. Biol. Chem.* 275:6499-6508 (2000). Competitive RT-PCR for quantitation of endogenous human Bcl-2 mRNA can be performed, for example, using primers 5'-ACTTGTGGC-CCAGATAGGCACCCAG-3' (SEQ ID NO:10) and 5'-CGACTTCGCCGAGATGTCCAGCCAG-3' (SEQ ID NO:11) to amplify a 385 bp fragment of endogenous Bcl-2 as described, for example, in Wu et al., *Oncoaene* 20:240-251 (2001). Furthermore, Northern blot analysis and nuclear run-on assays for Bcl-2 transcription can be routinely performed as described, for example, in Lesault et al., *EMBO J.* 21:694-703 (2002). Commercially available kits and products for detecting an altered Bcl-2 mRNA or polypeptide level also are known in the art; for example, Serologicals Corporation (Norcross, Ga.) provides a fluorescent quantitative PCR kit (Amplifluor™) for quantifying human Bcl-2 expression, and Maxim Biotech (South San Francisco, Calif.) provides RT-PCR kits for quantitation of human, murine or rat Bcl-2 expression. The skilled person understands that these and other assays can be useful for detecting an altered Bcl-2 level in the screening methods of the invention.

Assays for detecting the amount of a polypeptide also can be useful in the methods of the invention. Such assays can be used, for example, to assay for the amount of endogenous or exogenous Bcl-2 polypeptide or for the level of an encoded reporter gene product, which is expressed from a nucleic acid molecule operably linked to a Bcl-2 promoter. Purification of Bcl-2 or a reporter gene product can be achieved, for example, by HPLC, alone or in combination with mass spectrophotometry. Quantitation can be determined by well known methods including Bradford assays, Coomassie blue staining and assays for radiolabeled protein.

Immunoassays can be useful for detecting an altered Bcl-2 level in a method of the invention. Immunoassays, including competitive and non-competitive immunoassay formats, antigen capture assays and two-antibody sandwich assays are well known in the art and useful the methods of the invention, as are capillary electrophoresis based immunoassays (CEIA), which can be automated, if desired; immunoassays performed in conjunction with laser-induced fluorescence; liposome immunoassays including flow-injection liposome immunoassays; and western blotting including quantitative western blotting performed, for example, using densitometry. In particular embodiments, the invention is practiced with a radioimmunoassay or enzyme-linked immunosorbent assay (ELISA), which are well known in the art. See, for example, Harlow and Lane, *Antibodies A Laboratory Manual* Cold Spring Harbor Laboratory: New York, 1988)).

Anti-Bcl-2 antibodies or antibodies that immunoreact with convenient reporter gene products are well known in the art; as non-limiting examples, anti-Bcl-2 antibodies are commercially available from Santa Cruz Biotechnology (Santa Cruz, Calif.); Trevigen (Gaithersburg, Md.) and Roche Diagnostics (Indianapolis, Ind.); anti-β-galactosidase antibodies are available from Research Diagnostics (Flanders, N.J.) and Roche Diagnostics; and anti-GFP antibodies are available, for example, from Novus Biologicals (Littleton, Colo.). Western blotting to determine the expression level of Bcl-2 is described, for example, in Miyake et al., *Oncogene* 16:933-943 (1998) and Gomez-Monzano et al., supra, 2001.

The Bit1 encoding and AES encoding nucleic acid molecules disclosed herein as encoding polypeptides with pro-apoptotic activity can be used to diagnose, treat or reduce the severity of a cell accumulation disorder or a disorder of cell loss. As an example, Bit1 or AES encoding nucleic acid molecules, polypeptides and fragments thereof can be used for diagnosis of a cell accumulation disorder or a disorder of cell loss or can be used to generate reagents useful for such diagnoses. As described further below, diagnosis can be performed, without limitation, by nucleic acid probe hybridization, by amplification of Bit1 or AES encoding nucleic acid sequences and subsequent analysis, for example, electrophoretic analysis such as DNA sequencing. Diagnosis also can be performed, for example, using antibody or ligand-based detection with a binding-agent that selectively binds a Bit1 polypeptide or that selectively binds an AES polypeptide. It is understood that determination of a test expression level of Bit1 mRNA or polypeptide, or a test expression level of AES mRNA or polypeptide, can be performed ex vivo if desired, for example, by removing a cell or tissue sample from an asymptomatic individual with no risk factors, or from an individual at risk of, suspected of having, or exhibiting one or more symptoms of a cell accumulation disorder or a disorder of cell loss. An altered expression level of Bit1 mRNA or polypeptide, or an altered expression level of AES mRNA or polypeptide is indicative of a disorder of cell accumulation or a disorder of cell loss, or a predisposition thereto.

Thus, the present invention provides a method of diagnosing or predicting susceptibility to a cell accumulation disorder or a disorder of cell loss in an individual by contacting a sample from the individual with a Bit1 nucleic acid molecule; determining a test expression level of Bit1 mRNA in the sample; and comparing the test expression level to a control expression level of Bit1 mRNA, where an altered test expression level as compared to the control expression level indicates the presence of a cell accumulation disorder or a disorder of cell loss, or a predisposition thereto. In a method of the invention, the Bit1 nucleic acid molecule can include, for example, at least 10 contiguous nucleotides of SEQ ID NO:1.

Also provided herein is a method of diagnosing or predicting susceptibility to a cell accumulation disorder or a disorder of cell loss in an individual by contacting a sample from the individual with an AES nucleic acid molecule; determining a test expression level of AES mRNA in the sample; and comparing the test expression level to a control expression level of AES mRNA, where an altered test expression level as compared to the control expression level indicates the presence of a cell accumulation disorder or a disorder of cell loss, or a predisposition thereto.

In the above methods of the invention, the altered test expression level can be an increased expression level that indicates the presence of a disorder of cell loss, or a predisposition thereto. As non-limiting examples, the disorder of cell loss can be Alzheimer's disease, Parkinson's disease, amyotrophic lateral sclerosis, retinitis pigmentosa, anemia, myocardial infarction or stroke. The altered test expression level also can be a decreased expression level that indicates the presence of a cell accumulation disorder, or a predisposition thereto. Examplary cell accumulation disorders include, without limitation, cancer, autoimmune disease and atherosclerosis.

Also provided herein is a method of diagnosing or predicting susceptibility to a cell accumulation disorder or a disorder of cell loss in an individual by contacting a sample from the individual with a binding agent that selectively binds a Bit1 polypeptide; determining a test expression level of Bit1 polypeptide in the sample; and comparing the test expression level to a control expression level of Bit1 polypeptide, where an altered test expression level as compared to the control expression level indicates the presence of a cell accumulation disorder or a disorder of cell loss, or a predisposition thereto. As a non-limiting example, the binding agent can be an antibody or antigen-binding fragment thereof. In one embodiment, the altered test expression level is an increased expression level that indicates the presence of a disorder of cell loss, or a predisposition thereto. Such a disorder of cell loss can be, for example, Alzheimer's disease, Parkinson's disease, amyotrophic lateral sclerosis, retinitis pigmentosa, anemia, myocardial infarction or stroke. In another embodiment, the altered test expression level is a decreased expression level that indicates the presence of a cell accumulation disorder, or a predisposition thereto, including but not limited to cancer, autoimmune disease or atherosclerosis.

The present invention also provides a method of diagnosing or predicting susceptibility to a cell accumulation disorder or a disorder of cell loss in an individual by contacting a sample from the individual with a binding agent that selectively binds an AES polypeptide; determining a test expression level of AES polypeptide in the sample; and comparing the test expression level to a control expression level of AES polypeptide, where an altered test expression level as compared to the control expression level indicates the presence of a cell accumulation disorder or a disorder of cell loss, or a predisposition thereto. Useful binding agents include, without limitation, antibodies and antigen-binding fragments thereof. In a method of the invention, the altered test expression level can be, for example, an increased expression level that indicates the presence of a disorder of cell loss, or a predisposition thereto. The altered test expression level also can be, for example, a decreased expression level that indicates the presence of a cell accumulation disorder, or a predisposition thereto.

The present invention further provides a method of diagnosing or predicting susceptibility to a cell accumulation disorder or a disorder of cell loss in an individual by determining a test amount of Bit1 polypeptide-AES polypeptide complex in a sample from the individual; and comparing the test amount to a control amount of Bit1 polypeptide-AES polypeptide complex, where an altered test amount as compared to the control amount indicates the presence of a cell accumulation disorder or a disorder of cell loss, or a predisposition thereto. The altered test amount can be an increased or decreased test amount. In particular embodiments, the invention is practiced to diagnose or predict susceptibility to one of the following disorders of cell loss: Alzheimer's disease, Parkinson's disease, amyotrophic lateral sclerosis, retinitis pigmentosa, anemia, myocardial infarction or stroke. In other embodiments, the invention is practiced to diagnose or predict susceptibility to one of the following cell accumulation disorders: cancer, autoimmune disease or atherosclerosis. A variety of means can be used to determine the amount of a Bit1 polypeptide-AES polypeptide complex including, without limitation, co-immunoprecipitation assays.

Also provided by the invention is a method of diagnosing or predicting susceptibility to a cell accumulation disorder or a disorder of cell loss in an individual that involves (a) contacting a cell or subcellular fraction thereof from the individual with a binding agent that selectively binds a Bit1 polypeptide; (b) determining a test expression level of Bit1 polypeptide in a cellular location or subcellular fraction; and (c) comparing the test expression level to a control expression level of Bit1 polypeptide in the cellular location or subcellular fraction, wherein an altered test expression level as compared to the control expression level indicates the presence of a cell accumulation disorder or a disorder of cell loss, or a predisposition thereto. In one embodiment, the cellular location or subcellular fraction is a cytoplasmic location or fraction. In another embodiment, the cellular location or subcellular fraction is a mitochondrial location or fraction.

As disclosed herein, Bit1 polypeptide expression in the cytoplasm of a cell is associated with Bit1 pro-apoptotic activity. Therefore, the expression level of Bit1 can be determined to assess whether a cell is in a pro-apoptotic or non-apoptotic state. For example, an increased level of Bit1 expression as compared to a control expression level would indicate increased apoptosis characteristic of a disorder of cell loss or predisposition thereto. Similarly, a decreased level of Bit1 expression in the mitochondria as compared to a control expression level would indicate increased apoptosis characteristic of a disorder of cell loss or predisposition thereto. Conversely, a decreased level of cytoplasmic Bit1 expression as compared to a control cytoplasmic expression level, or increased level of mitochondrial Bit1 expression as compared to a control mitochondrial expression level, would indicate a non-apoptotic state characteristic of a accumulation disorder or a predisposition thereto.

A Bit1 expression level in a cellular location refers to Bit1 polypeptide expression in a cell, which can be intact, fixed, or processed in any manner so long as cytoplasmic and mitochondrial compartments remain discernible. A Bit1 expression level in a cellular location can be determined using any method that can distinguish cytoplasm from other cellular locations, such as mitochondrial or nuclear locations.

A Bit1 expression level in a cytoplasmic fraction refers to Bit1 polypeptide expression in an isolated compartment or portion of a cell, such as a cell cytoplasm or mitochondrial portion. Bit1 expression levels in a subcellular fraction can be determined using any of a variety of methods for detecting Bit1 expression. Exemplary methods for determining Bit1 expression levels in particular cellular locations and in subcellular fractions are described herein below.

Antibodies can be useful in the diagnostic methods of the invention. As used herein, the term "antibody" is used in its broadest sense to include polyclonal and monoclonal antibodies, as well as polypeptide fragments of antibodies that retain binding activity for a Bit1 polypeptide or AES polypeptide of at least about $1 \times 10^5$ $M^{-1}$. One skilled in the art understands that anti-Bit1 antibody fragments and anti-AES antibody fragments, such as Fab, F(ab')$_2$ and Fv fragments, can retain binding activity for Bit1 or AES and, thus, are included within the definition of the term antibody. In addition, the term "antibody," as used herein, encompasses non-naturally occurring antibodies and fragments containing, at a minimum, one $V_H$ and one $V_L$ domain, such as chimeric antibodies, humanized antibodies and single chain Fv fragments (scFv) that specifically bind a Bit1 polypeptide or AES polypeptide. Such non-naturally occurring antibodies can be constructed using solid phase peptide synthesis, produced recombinantly or obtained, for example, by screening combinatorial libraries consisting of variable heavy chains and variable light chains as described by Borrebaeck (Ed.), *Antibody Engineering* (Second edition) New York: Oxford University Press (1995)). One skilled in the art understands that such antibodies can be useful for diagnosing or predicting susceptibility to a cell accumulation disorder or a disorder of cell loss according to a method of the invention.

Anti-Bit1 or anti-AES antibodies can be prepared, for example, using a Bit1 or AES fusion protein or a synthetic peptide encoding a portion of a Bit1 or AES as an immunogen. One skilled in the art understands that purified Bit1 and AES, which can be produced recombinantly, or fragments of Bit1 and AES, including peptide portions of Bit1 and AES such as synthetic peptides, can be used as immunogens. Furthermore, non-immunogenic fragments or synthetic peptides of Bit1 and AES can be made immunogenic by coupling the hapten to a carrier molecule such as bovine serum albumin (BSA) or keyhole limpet hemocyanin (KLH). In addition, various other carrier molecules and methods for coupling a hapten to a carrier molecule are well known in the art are described, for example, by Harlow and Lane, *Antibodies: A Laboratory Manual* (Cold Spring Harbor Laboratory Press, 1988)).

The methods of the invention are useful, in part, for diagnosing or predicting susceptibility to cell accumulation disorders, and for preventing or reducing the severity of these disorders. Cell accumulation disorders include cancers. As non-limiting examples, Bit1 is prominently expressed, for example, in testis, prostate, and liver tissue; reduced levels of Bit1 and, therefore, diminished apoptotic cell death, can contribute, for example, to testicular cancer, prostate cancer and hepatic cancer. Additionally, autoimmune diseases, such as myasthenia gravis, rheumatoid arthritis, systemic lupus erythematosus and immune-mediated glomerulonephritis, and viral infections such as herpesvirus, poxvirus and adenovirus are encompassed by the term "cell accumulation disorder." Pathological conditions involving smooth or cardiac muscle cells, such as hepatic necrosis vasculitis, angiogenesis, atherosclerosis and myocarditis, also can result from increased cell accumulation and are encompassed by the term cell accumulation disorder as used herein. Similar pathological conditions can exist where there is activation of a cell regulatory molecule causing the inappropriate survival of the cell. Any such pathology is encompassed within the term "cell accumulation disorder," which, as used herein, means a disease, pathology or other condition resulting in an abnormally high number of cells of a particular type. Such disorders are frequently characterized by diminished cell death or differentiation or excess cellular proliferation or cellular lifespan. The methods of the invention are useful for diagnosing or treating any of such disorders.

The methods of the invention also can be useful for diagnosing or predicting susceptibility to a disorder of cell loss or for treating such a disorder as disclosed hereinbelow. Non-limiting examples of disorders of cell loss, which can result, for example, from excessive programmed cell death, include AIDS and degenerative disorders such as Alzheimer's disease, Parkinson's disease, amyotrophic lateral sclerosis, retinitis pigmentosa, and cerebellar degeneration. Disorders of cell loss resulting from excessive programmed cell death further include, without limitation, myelodysplastic syndromes such as aplastic anemia and ischemic injuries such as myocardial infarction, stroke and reperfusion injury. Any such pathology is encompassed by the term "disorder of cell loss," which, as used herein, means a disease, pathology or other condition resulting in an abnormally reduced number of cells of a particular type. Such disorders frequently are characterized by excessive cell death or differentiation or inadequate cellular proliferation or truncated cellular life-span.

The methods of the invention relate to diagnosing or predicting susceptibility in an individual. As used herein, the term "individual" means any animal capable of having a cell accumulation disorder or a disorder of cell loss. Individuals to be diagnosed according to a method of the invention include mammals such as primates and, in one embodiment, are humans. It is understood that an individual to be diagnosed can be, for example, symptomatic or asymptomatic, can have no risk factors or one or several risk factors for a cell accumulation disorder or a disorder of cell loss, and also can be suspected of having a cell accumulation disorder or a disorder of cell loss. It further is understood that the methods of the invention can be combined, if desired, with one or more additional molecular tests or clinical criteria to diagnose or predict susceptibility to a cell accumulation disorder or a disorder of cell loss.

Figure 9:
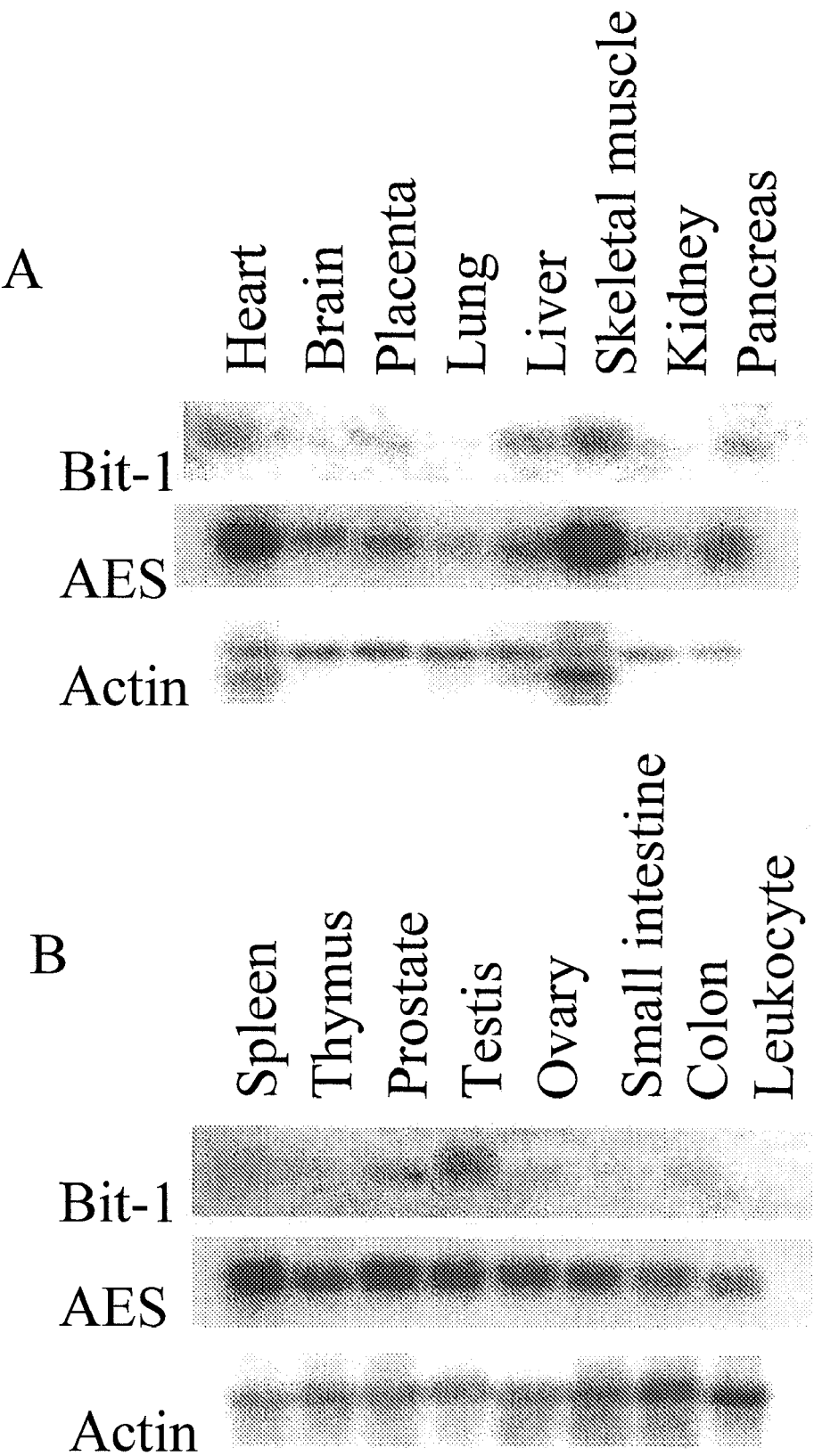
FIG. 9 shows Bit1 and AES expression in various human tissues and cell lines. (A and B) Human tissues analyzed by Northern blotting with full-length Bit1 and AES cDNA probes. Actin mRNA was used as a loading control. (C) Cell lines analyzed by Northern blotting with full-length Bit1 and AES cDNA probes.

Several of the methods of the invention relate to determining a test expression level of Bit1 or AES mRNA or polypeptide in a sample. As used herein, the term "sample" means any biological matter in which Bit1 or AES can be expressed under normal or pathological conditions. In one embodiment, a "sample" is a tissue biopsy. Samples useful in the invention include, but are not limited to, heart, brain, placenta, lung, liver, skeletal muscle, kidney, pancreas, spleen, thymus, prostate, testis, ovary, small intestine, and leukocyte samples. Normal human tissues that express Bit1 and AES are shown in FIG. 9.

Any of the above methods for diagnosing or predicting susceptibility to a cell accumulation disorder or a disorder of cell loss also can be used to monitor the effectiveness of therapy, to subtype or stage the disorder or to assess patient prognosis. As an example, the diagnostic methods disclosed herein can also be adapted for use as prognostic assays. Such an application takes advantage of the observation that alterations in the expression or structure of different molecules involved in apoptosis can take place at characteristic stages in the progression of a cell accumulation disorder or a disorder of cell loss. Knowledge of the stage of the disorder allows the clinician to select the most appropriate treatment and to predict the likelihood of success of that treatment.

Procedures useful for in vitro or in vivo determination of a test amount of Bit1-AES complex in a sample include immunoassays that employ a detectable antibody. Such immunoassays include, without limitation, immunohistochemical assays, immunofluorescence assays, ELISA assays, radioimmunoassays, fluorescence activated cell sorting, immunoprecipitation assays, immunoblotting, Pandex microfluorimetric assays, agglutination assays, flow cytometric assays and serum diagnostic assays, which are well known in the art (Harlow and Lane, supra, 1988; Harlow and Lane, *Using Antibodies: A Laboratory Manual*, Cold Spring Harbor Press (1999)). An antibody can be made detectable by various means well known in the art. As non-limiting examples, a detectable label can be directly attached to the antibody or indirectly attached using, for example, a secondary compound that recognizes an anti-Bit1 or AES antibody. Useful labels include, for example, radiolabels, enzymes, biotin, fluorescent labels, chromogenic labels and chemiluminescent labels.

Further provided herein are methods of preventing or reducing the severity of a disorder of cell loss in a subject by administering to the subject an effective agent that selectively decreases Bit1 expression or activity, thereby inhibiting apoptosis in the subject. Disorders of cell loss to be treated according to a method of the invention include, without limitation, Alzheimer's disease, Parkinson's disease, amyotrophic lateral sclerosis, retinitis pigmentosa, anemia, myocardial infarction and stroke. A variety of effective agents that selectively decrease Bit1 expression or activity can be useful in the invention. As non-limiting examples, such effective agents include small molecules, nucleic acid molecules, polypeptides, peptides, peptidomimetics, and antibodies or antigen-binding fragments thereof. Any of the above effective agents can be linked, if desired, to a homing molecule, which can be a homing peptide such as a tumor homing peptide.

The invention also provides a method of preventing or reducing the severity of a cell accumulation disorder in a subject by administering to the subject an effective agent that selectively increases Bit1 expression or activity, thereby enhancing apoptosis in the subject. A variety of cell accumulation disorders can be treated according to a method of the invention including, for example, cancer, autoimmune disease and atherosclerosis. Exemplary effective agents that selectively increase Bit1 expression or activity include, without limitation, small molecules, nucleic acid molecules, and polypeptides. Nucleic acid molecules useful in the invention include, without limitation, those encoding Bit1 or a pro-apoptotic fragment thereof. These and other effective agents can be optionally linked to a homing molecule, which can be a homing peptide such as a tumor homing peptide.

The present invention additionally provides methods of preventing or reducing the severity of a disorder of cell loss in a subject by administering to the subject an effective agent that selectively decreases AES expression or activity, thereby inhibiting apoptosis in the subject. A variety of effective agents that selectively decrease AES expression or activity can be useful in the invention including, without limitation, small molecules, nucleic acid molecules, polypeptides, peptides, peptidomimetics, and antibodies or antigen-binding fragments thereof. Any of the above or other disorders of cell loss can be treated with an effective agent that selectively decreases AES expression or activity according to a method of the invention. If desired, the effective agent can be linked to a homing peptide or other homing molecule, for example, a tumor homing peptide.

Also provided herein is a method of preventing or reducing the severity of a cell accumulation disorder in a subject by administering to the subject an effective agent that selectively increases AES expression or activity, thereby enhancing apoptosis in the subject. A variety of cell accumulation disorders can be treated according to a method of the invention; exemplary disorders include cancer, autoimmune disease and atherosclerosis. A variety of effective agents that selectively increase AES expression or activity can be useful in the invention such as, without limitation, small molecules, nucleic acid molecules, and polypeptides. Such effective agents include, yet are not limited to, nucleic acid molecules encoding AES or a pro-apoptotic fragment thereof. Furthermore, these and other effective agents can be optionally linked to a homing peptide or other homing molecule, for example, a tumor homing peptide.

The present invention also provides a method of inducing apoptosis in cancer cells in vivo by administering to a subject Bit1 or a pro-apoptotic fragment thereof, thereby inducing apoptosis in the cancer cells. A pro-apoptotic Bit1 fragment can be, for example, a Bit1 fragment including residues 1-76 of Bit1 or residues 27-76 of Bit1. AES or a pro-apoptotic fragment thereof can optionally also be administered to the subject.

Further provided herein is a method of inducing apoptosis in cancer cells in vivo by administering to a subject AES or a pro-apoptotic fragment thereof, thereby inducing apoptosis in the cancer cells. A method of the invention can be practiced, for example, with a pro-apoptotic AES fragment containing residues 57-105 of AES or a pro-apoptotic AES fragment containing residues 57-88 of AES.

As used herein, the term "subject" means any animal capable of having a cell accumulation disorder or a disorder of cell loss. A subject typically has one or more risk factors for a cell accumulation disorder or a disorder of cell loss, or exhibits one or more symptoms of a cell accumulation disorder or a disorder of cell loss, or has a previous confirmed or unconfirmed diagnosis of having a cell accumulation disorder or a disorder of cell loss. Subjects to be treated according to a method of the invention include mammals such as primates. In particular embodiments, the methods of the invention are practiced to prevent or reduce the severity of a cell accumulation disorder or a disorder of cell loss in a human.

As disclosed herein, an effective agent that selectively decreases Bit1 expression or activity, or that selectively decreases AES expression or activity can be a useful therapeutic molecule. As used herein, the term "effective agent that selectively decreases Bit1 expression or activity" means a molecule that reduces the level of Bit1 RNA or polypeptide, or that inhibits one or more biological activities, such as pro-apoptotic activity, of Bit1 relative to an unrelated polypeptide. Similarly, the term "effective agent that selectively decreases AES expression or activity" means a molecule that reduces the level of AES RNA or polypeptide, or that inhibits one or more biological activities, such as pro-apoptotic activity, of AES relative to an unrelated polypeptide.

Such effective agents useful in the invention include, without limitation, small molecules, proteins, peptides, peptidomimetics, ribozymes, nucleic acid molecules and oligonucleotides, oligosaccharides, cells, phages and viruses, and combinations thereof. As non-limiting examples, effective agents that selectively decrease Bit1 expression or activity encompass dominant negative Bit1 polypeptides or encoding nucleic acid molecules; Bit1 binding molecules including molecules that bind the AES-binding domain, including antibodies, proteins, small molecules and oligonucleotides that prevent or diminish binding to AES; anti-Bit1 antibodies; conjugates in which a Bit1 binding molecule is linked to a toxin; ribozymes, antisense nucleic acid molecules and nucleic acid molecules encoding negative regulatory transcription factors that prevent or reduce Bit1 expression, as well as cells or viruses containing such ribozymes and nucleic acid molecules.

Similarly, effective agents that selectively decrease AES expression or activity encompass, without limitation, dominant negative AES polypeptides or encoding nucleic acid molecules; AES binding molecules including molecules that bind the Bit1-binding domain of AES, including antibodies, proteins, small molecules and oligonucleotides that prevent or diminish binding to Bit1; anti-AES antibodies; conjugates in which an AES binding molecule is linked to a toxin; ribozymes, antisense nucleic acid molecules and nucleic acid molecules encoding negative regulatory transcription factors that prevent or reduce AES expression, as well as cells or viruses containing such ribozymes and nucleic acid molecules. One skilled in the art understands that these and other effective agents that selectively decrease Bit1 or AES expression or activity can be useful in the methods of the invention.

Effective agents that selectively increase Bit1 expression or activity, or that selectively increase AES expression or activity also can be useful therapeutic molecules. As used herein, the term "effective agent that selectively increases Bit1 expression or activity" means a molecule that upregulates the level of Bit1 RNA or polypeptide, or that enhances or accelerates one or more biological activities, such as pro-apoptotic activity, of Bit1 relative to an unrelated polypeptide. Similarly, the term "effective agent that selectively increases AES expression or activity" means a molecule that upregulates the level of AES RNA or polypeptide, or that enhances or accelerates one or more biological activities, such as pro-apoptotic activity, of AES relative to an unrelated polypeptide.

Effective agents that selectively increase Bit1 expression or activity encompass full-length and truncated Bit1 polypeptides such as carboxy-terminal deletions having, for example, residues 1-76 of Bit1; nucleic acid molecules encoding full-length or truncated forms of Bit1 such as a nucleic acid molecule encoding residues 1-76 of Bit1; Bit1 binding molecules; antibodies, proteins, small molecules and oligonucleotides that stabilize or increase binding to AES; transcription factors that increase Bit1 expression, and nucleic acid molecules encoding such transcription factors; molecules that enhance or accelerate Bit1 pro-apoptotic activity; and cells or viruses expressing any of the above molecules. In a similar manner, effective agents that selectively increase AES expression or activity encompass full-length and truncated AES polypeptides such as AES polypeptide deletions retaining residues 57-105 or 57-88 of AES; nucleic acid molecules encoding full-length or truncated forms of AES including nucleic acid molecules encoding residues 57-105 or residues 57-88 of AES; AES binding molecules; antibodies, proteins, small molecules and oligonucleotides that stabilize or increase binding to Bit1; transcription factors that increase AES expression, and nucleic acid molecules encoding such transcription factors; molecules that enhance or accelerate AES pro-apoptotic activity; and cells or viruses expressing any of the above molecules.

The present invention also provides a method of selectively inducing apoptosis in cancer cells in vivo by administering to a subject a conjugate which contains a homing peptide linked to Bit1 or a pro-apoptotic fragment thereof, where the conjugate selectively homes to cancer cells and induces apoptosis in the cancer cells. In a method of the invention, the conjugate can include, for example, a pro-apoptotic Bit1 fragment which includes residues 1-76 of Bit1, or which includes residues 27-76 of Bit1. If desired, AES or a pro-apoptotic fragment thereof can additionally be administered to the subject.

The present invention further provides a method of selectively inducing apoptosis in cancer cells in vivo by administering to a subject a conjugate which contains a homing peptide linked to AES or a pro-apoptotic fragment thereof, where the conjugate selectively homes to cancer cells and induces apoptosis in the cancer cells. A conjugate useful in the invention can contain, for example, a pro-apoptotic AES fragment that includes residues 57-105 of AES or a pro-apoptotic AES fragment that includes residues 57-88 of AES.

The term "homing molecule" is synonymous with "organ homing homing" and means an organic chemical such as a drug; a nucleic acid molecule; a peptide or peptidomimetic or protein that selectively homes in vivo to a selected cell type or tissue. By "selectively homes" is meant that, in vivo, the homing molecule binds preferentially to a selected cell type or tissue as compared to a control cell type, tissue or organ and generally is characterized by at least a two-fold greater localization at the selected cell type or tissue compared to a control cell type or tissue. A homing molecule useful in the invention can be, for example, a molecule that binds preferentially to the endothelial cells of prostate vasculature as compared to other vasculature.

Similarly, the term "tumor homing molecule," as used herein, means an organic chemical such as a drug; a nucleic acid molecule; a peptide or peptidomimetic or protein that selectively homes in vivo to one or more selected tumor types. By "selectively homes" is meant that, in vivo, the tumor homing molecule binds preferentially to a selected tumor type as compared to a control cell type, tissue or organ and generally is characterized by at least a two-fold greater localization at the selected tumor type compared to a control cell type or tissue. A tumor homing molecule useful in the invention can be, for example, a molecule that binds preferentially to the endothelial cells of angiogenic vasculature as compared to other cell types or angiostatic vasculature.

Tumor homing peptides include those which have the sequence arginine-glycine-aspartic acid (RGD); those having the sequence asparagine-glycine-arginine (NGR); and those having a glycine-serine-leucine (GSL) motif. Exemplary tumor homing peptides include CDCRGDCFC (SEQ ID NO:12); CNGRC (SEQ ID NO:13); NGRAHA (SEQ ID NO:14) and CNGRCVSGCAGRC (SEQ ID NO:15); and CGSLVRC (SEQ ID NO:16); tumor homing peptides and molecules that selectively home to lymphatic vasculature; and tumor homing peptides which are fragments of HMGN2, or analogs thereof. A variety of different tumor homing peptides are known in the art, as described, for example, in WO98/10795; Arap et al., *Science* 279:377-380 (1998); Arap et al., *Curr. Opin. Oncol.* 10:560-565 (1998); Porkka et al., *Proc. Natl. Acad. Sci., USA* 99:7444-7449 (2002); and Laakkonen et al., *Nat. Medicine* 8:751-755 (2002), each of which is incorporated herein by reference. The skilled person understands that these and other tumor homing peptides and tumor homing molecules can be useful in the methods of the invention.

A variety of homing peptides and homing molecules also can be useful in the methods of the invention. These include, but are not limited to, prostate homing molecules, breast homing molecules such as those that bind to aminopeptidase P, lung homing molecules such as those that bind to membrane dipeptidase; and molecules that selectively home to skin, pancreas, retina, ovary, lymph node, adrenal gland, liver or gut. A variety of such organ homing molecules are known in the art as described, for example, in Rajotte et al., *J. Clin. Invest.* 102:430-437 (1998); Ruoslahti and Rajotte, *Annual Rev. Immunol.* 18:813-827 (2000); Rajotte and Ruoslahti, *J. Biol. Chem.* 274:11593-11598 (1999); Arap et al., *Proc. Natl. Acad. Sci. USA* 99:1527-1531 (2002); and Essler and Ruoslahti, *Proc. Natl. Acad. Sci., USA* 99:2252-2257 (2002). These and other organ homing molecules including organ homing peptides and peptidomimetics can be useful in the methods of the invention.

Effective agents useful in the invention can optionally be formulated together with a pharmaceutically acceptable carrier for delivery to a cultured cell or to a subject. Suitable pharmaceutically acceptable carriers are well known in the art and include, without limitation, aqueous or organic solvents such as physiologically buffered saline, glycols, glycerol, oils or injectable organic esters. A pharmaceutically acceptable carrier can also contain a physiologically acceptable compound that acts, for example, to stabilize or increase the solubility of a pharmaceutical composition. Such physiologically acceptable compounds include but are not limited to carbohydrates, such as glucose, sucrose or dextrans; antioxidants, such as ascorbic acid or glutathione; chelating agents; low molecular weight polypeptides; and other stabilizers or excipients. Furthermore, such pharmaceutically acceptable carriers, including solvents, stabilizers, solubilizers and preservatives, are well known in the art as described, for example, in Martin, *Remington's Pharm. Sci.,* 15th Ed. (Mack Publ. Co., Easton, 1975).

Effective agents useful in the invention can be administered to a subject by any effective route. Suitable routes for delivering the therapeutic molecules of the invention include local and systemic routes of administration such as, without limitation, oral, topical, subcutaneous, intravenous, intramuscular, parenteral, intraocular, intradermal, intranasal, intraspinal and intracerebral administration.

Methods of ensuring appropriate distribution in vivo can also be provided by rechargeable or biodegradable devices, particularly where gradients of concentrations of drug in a tissue are desired. Various slow release polymeric devices are known in the art for the controlled delivery of drugs, and include biodegradable and non-degradable polymers and hydrogels as well as implantable devices. Those skilled in the art understand that the choice of the pharmaceutical formulation and the appropriate preparation of the composition will depend on the intended use and mode of administration.

An appropriate dose of an effective agent useful in the invention can be determined, for example, by extrapolation from the concentration required for altered association, selective binding, altered cell death or altered Bcl-2 transcription in an assay disclosed herein or by the dose required to modulate cellular proliferation. An appropriate dose useful in the invention also be determined from appropriate animal models, including transgenic models. The appropriate dose for treatment of a human subject can be determined by one skilled in the art, and is dependent on the nature and bioactivity of the particular effective agent, the half-life of the agent, the desired route of administration, the gender, age and health of the subject, the number of doses and duration of treatment, and the particular disorder being treated.

The methods of the invention involve gene therapy methods in which a nucleic acid molecule encoding, for example, Bit1 or AES or a pro-apoptotic fragment thereof, is administered to a subject. A variety of vectors can be useful in the gene therapy methods of the invention including, without limitation, viral vectors such as retroviral vectors, adenovirus, adeno-associated virus, lentivirus, herpesvirus, and non-viral vectors such as plasmid vectors. Such vectors are useful for providing therapeutic amounts of a nucleic acid molecule such as a nucleic acid molecule encoding Bit1 or AES or a pro-apoptotic fragment thereof.

Viral based systems provide the advantage of being able to introduce relatively high levels of the heterologous nucleic acid molecule into a variety of cells. Suitable viral vectors include yet are not limited to Herpes simplex virus vectors (Geller et al., *Science* 241:1667-1669 (1988)); vaccinia virus vectors (Piccini et al., *Meth. Enzymology* 153:545-563 (1987)); cytomegalovirus vectors (Mocarski et al., in *Viral Vectors*, Y. Gluzman and S. H. Hughes, Eds., Cold Spring Harbor Laboratory, Cold Spring Harbor, N.Y., 1988, pp. 78-84)); Moloney murine leukemia virus vectors (Danos et al., *Proc. Natl. Acad. Sci. USA* 85:6460-6464 (1988); Blaese et al., *Science* 270:475-479 (1995); Onodera et al., *J. Virol.* 72:1769-1774 (1998)); adenovirus vectors (Berkner, *Biotechniques* 6:616-626 (1988); Cotten et al., *Proc. Natl. Acad. Sci., USA* 89:6094-6098 (19.92); Graham et al., *Meth. Mol. Biol.* 7:109-127 (1991); Li et al., *Human Gene Therapy* 4:403-409 (1993); Zabner et al., *Nature Genetics* 6:75-83 (1994)); adeno-associated virus vectors (Goldman et al., *Human Gene Therapy* 10:2261-2268 (1997); Greelish et al., *Nature Med.* 5:439-443 (1999); Wang et al., *Proc. Natl. Acad. Sci., USA* 96:3906-3910 (1999); Snyder et al., *Nature Med.* 5:64-70 (1999); Herzog et al., *Nature Med.* 5:56-63 (1999)); retrovirus vectors (Donahue et al., *Nature Med.* 4:181-186 (1998); Shackleford et al., *Proc. Natl. Acad. Sci., USA* 85:9655-9659 (1988); U.S. Pat. Nos. 4,405,712, 4,650,764 and 5,252,479, and WIPO publications WO 92/07573, WO 90/06997, WO 89/05345, WO 92/05266 and WO 92/14829; and lentivirus vectors (Kafri et al., *Nature Genetics* 17:314-317 (1997)). The skilled person understands that these and other methodologies can be useful for administering a nucleic acid molecule according to a method of the invention.

The present invention further provides a pro-apoptotic Bit1 fragment which includes residues 1-76 of Bit1 or a portion thereof, where the pro-apoptotic Bit1 fragment has at most 150 residues of Bit1 and has pro-apoptotic activity. In one embodiment, the pro-apoptotic Bit1 fragment includes residues 1-76 of Bit1. In further embodiments, a pro-apoptotic Bit1 fragment of the invention includes residues 1-76 of Bit1 or a portion thereof and also includes at most 100 residues, at most 76 residues or at most 50 residues of Bit1. In a further embodiment, the pro-apoptotic Bit1 fragment consists of residues 1-76 of Bit1. In yet another embodiment, the pro-apoptotic Bit1 fragment consists of residues 27-76 of Bit1. It is understood that a pro-apoptotic Bit1 fragment can be fused to a heterologous protein or peptide such as a homing peptide as described above.

The present invention further provides a pro-apoptotic AES fragment that includes residues 57-105 of AES or a portion thereof, where the pro-apoptotic fragment includes at most 150 residues of AES and has pro-apoptotic activity. In one embodiment, a pro-apoptotic AES fragment of the invention includes residues 57-105 of AES. In further embodiments, the pro-apoptotic AES fragment includes residues 57-105 of AES or a portion thereof and also includes at most 100, at most 70 or at most 50 residues of AES. In a further embodiment, the pro-apoptotic AES fragment consists of residues 57-105 of AES.

The present invention further provides a pro-apoptotic AES fragment that includes residues 57-88 of AES or a portion thereof, where the pro-apoptotic fragment includes at most 75 residues of AES and has pro-apoptotic activity. In one embodiment, a pro-apoptotic AES fragment of the invention includes residues 57-88 of AES. In further embodiments, the pro-apoptotic AES fragment includes residues 57-88 of AES or a portion thereof and also includes at most 45, at most 40 or at most 35 residues of AES. In a further embodiment, the pro-apoptotic AES fragment consists of residues 57-88 of AES. Again, it is understood that a pro-apoptotic AES fragment can be fused to a heterologous protein or peptide such as a homing peptide.

The term "pro-apoptotic Bit1 fragment" means a peptide or polypeptide with pro-apoptotic activity that has substantially the same amino acid sequence as a portion of a Bit1 polypeptide. Similarly, the term "pro-apoptotic AES fragment" means a peptide or polypeptide with pro-apoptotic activity that has substantially the same amino acid sequence as a portion of an AES polypeptide. As disclosed herein, Bit1 and AES polypeptides have pro-apoptotic activity, as exemplified by their ability to induce or enhance apoptosis when expressed in mammalian cells (see Examples I and III). A Bit1 polypeptide can have, for example, pro-apoptotic activity in cells that express an AES polypeptide, while lacking this pro-apoptotic activity in the absence of AES polypeptide expression. Furthermore, a peptide or polypeptide having an amino acid sequence that is identical or substantially the same as a portion of human Bit1 (SEQ ID NO:2) such as residues 1-76 of human Bit1 (SEQ ID NO:4), encoded by the nucleotide sequence referenced as SEQ ID NO:3, or having an amino acid sequence that is identical or substantially the same as a portion of human AES (SEQ ID NO:6) such as residues 57-105 or residues 57-88 of human AES (SEQ ID NOS:8 or 9, respectively) also can have pro-apoptotic activity and can be a pro-apoptotic Bit1 fragment or a pro-apoptotic AES fragment, as defined herein. It is understood that a pro-apoptotic fragment of the invention can have apoptotic activity that is diminished or enhanced relative to the corresponding full-length Bit1 or AES polypeptide.

The term "apoptotic activity," as used herein, means the ability either alone, or in combination with another molecule, to produce cell death accompanied by at least one of the morphological or biochemical alterations which characterize apoptosis. As an example, a Bit1 polypeptide can have apoptotic activity in a cell expressing an AES polypeptide. Morphological alterations which characterize apoptosis are well known in the art and include, for example, condensed and rounded cellular morphology; membrane blebbing; the formation of apoptotic bodies, which are membrane-bound bodies containing cytoplasmic and nuclear components; and condensation of the nucleus, with cytoplasmic organelles being relatively well maintained (Studzinski (Ed.), *Cell Growth and Apoptosis*, Oxford: Oxford University Press (1995)). Biochemical alterations which characterize apoptosis also are well known in the art. A classical biochemical alteration which characterizes apoptosis is the appearance of oligonucleosome-sized fragments of DNA, which produce a "ladder" upon agarose gel electrophoresis. This extensive fragmentation may be preceded by an earlier endonucleolytic cleavage of chromatin producing DNA fragments of about 50 kb to 300 kb in size. A variety of assays known in the art for detecting apoptosis and are described hereinabove.

An isolated Bit1 or AES polypeptide, or a fragment or active fragment thereof useful in the invention, can be obtained by a variety of methods known within the art, including biochemical, recombinant and chemical synthesis methods. Biochemical methods for isolating a Bit1 or AES polypeptide or a fragment or active fragment thereof include preparative gel electrophoresis, gel filtration, affinity chromatography, ion exchange and reversed phase chromatography, chromatofocusing, isoelectric focusing and sucrose or glycerol density gradients (see, for example, Chapter 38 of Deutscher, *Methods in Enzymology: Guide to Protein Purification*, Vol. 182, Academic Press, Inc., San Diego and Chapter 8 of Balch et al., *Methods in Enzymology*, Vol. 257, Academic Press, Inc., San Diego (1995)).

Preparative gel electrophoresis can be useful in preparing an isolated Bit1 or AES polypeptide or a fragment or active fragment useful in the invention. As an example, a Bit1 or AES polypeptide or fragment or active fragment useful in the invention can be isolated by preparative polyacrylamide gel electrophoresis and elution of the polypeptide or fragment by diffusion or electroelution (see, for example, Chapter 33 of Deutscher, supra, 1990). Continuous elution gel electrophoresis using a system such as the Model 491 Prep Cell (BioRad, Hercules, Calif.) can be used to purify a Bit1 or AES polypeptide or fragment or active fragment thereof. If desired, continuous elution gel electrophoresis can be combined with further purification steps such as liquid phase preparative isoelectric focusing, for example, the Rotofor system (BioRad).

Affinity chromatography is particularly useful in preparing an isolated Bit1 or AES polypeptide or fragment or active fragment thereof useful in the invention. As disclosed herein, Bit1 co-immunoprecipitates with AES in vitro. Thus, an interacting polypeptide such as an AES polypeptide can be useful as an affinity matrix for isolation of Bit1.

Immunoaffinity chromatography can be particularly useful in isolating a Bit1 or AES polypeptide or fragment or active fragment thereof useful in the invention. As an example, immunoprecipitation or column chromatography with an antibody that selectively binds Bit1 can be used to isolate a Bit1 polypeptide or fragment or active fragment thereof. An anti-Bit1 monoclonal or polyclonal antibody that selectively binds Bit1 can be prepared using an immunogen such as the sequence shown as SEQ ID NO:2 or a synthetic peptide fragment thereof as described further below. Methods of affinity chromatography are well known in the art and are described, for example, in Chapters 29, 30 and 38 of Deutscher, supra, 1990.

Recombinant methods for producing a polypeptide through expression of a nucleic acid sequence in a suitable host cell also are well known in the art and are described, for example, in Sambrook et al., *Molecular Cloning: A Laboratory Manual*, Second edition, Volumes 1 to 3, Cold Spring Harbor Laboratory Press, New York (1989). A nucleic acid molecule for expression of human Bit1 polypeptide is provided herein as SEQ ID NO:1. Similarly, a nucleic acid molecule for expression of an AES polypeptide is provided herein as SEQ ID NO:5. For expression of a pro-apoptotic fragment of Bit1, a segment of the nucleic acid sequence provided as SEQ ID NO:1 can be used.

A recombinant Bit1 or AES polypeptide or fragment or active fragment thereof useful in the invention can be expressed as a fusion protein with a heterologous "tag" for convenient isolation away from bacterial or mammalian host proteins. Methods of preparing FLAG and myc-tagged Bit1 and AES fusion proteins are described herein in Example II. Similarly, histidine-tagged recombinant Bit1 or AES polypeptide, or a fragment or an active fragment thereof, which can be isolated by nickel-chelate chromatography, or polypeptides tagged with glutathione-S-transferase or an antigenic tag can be prepared by routine methods (Sambrook et al., supra, 1989).

A Bit1 or AES polypeptide or fragment or active fragment thereof also can be produced by chemical synthesis, for example, by the solid phase peptide synthesis method of Merrifield et al., *J. Am. Chem. Soc.* 85:2149 (1964). Standard solution methods well known in the art also can be used to synthesize a polypeptide or fragment or active fragment useful in the invention (Bodanszky, *Principles of Peptide Synthesis*, Springer-Verlag, Berlin (1984); Bodanszky, *Peptide Chemistry*, Springer-Verlag, Berlin (1993)). A newly synthesized polypeptide or fragment or active fragment can be purified, for example, by high performance liquid chromatography (HPLC) and can be characterized using mass spectrometry or amino acid sequence analysis.

The following examples are intended to illustrate but not limit the present invention.

EXAMPLE I

Identification of Bit1

This example describes isolation of a Bit1 clone based on regulation of Bcl-2 expression.

An expression cloning strategy was used to identify genes that can be involved in integrin-mediated regulation of Bcl-2 expression. To pursue this strategy, the integrin-Bcl-2 pathway was disabled by truncating the α5 integrin cytoplasmic domain (Matter and Ruoslahti, *J. Biol. Chem.* 276:27757-27763 (2001)). These cells (CHO-B2/α5Δcβ1) were cotransfected with a cDNA library and a reporter containing a green fluorescent protein (GFP) cDNA under control of the Bcl-2 promoter. Fluorescent cells were selected from the cotransfections, yielding five cDNA clones that produced increased GFP expression. Of these clones, two had multiple stop codons, and two were in the antisense orientation. The remaining clone, designated Clone-3, contained a 423 base pair open reading frame, which represented the 3' portion of a 537 base pair open reading frame in a gene denoted CGI-147. This gene encodes a protein with no known function that is evolutionarily conserved from *C. elegans* to man.

The entire CGI-147 open reading frame encodes a 27-kDa protein with no sequence similarity to other proteins. Clone-3, which is predicted to encode a protein with a molecular weight of 18 kDa, up-regulated expression of the Bcl-2 promoter construct when transfected into CHO cells. In contrast, the full-length form of this protein down-regulated Bcl-2 promoter activity in CHO cells. To denote this inhibitory transcriptional activity, the Clone-3 gene was denoted Bit1 for Bcl-2 inhibitor of transcription.

Bit1 activity was analyzed in the human embryonic kidney cell line, HEK 293. As shown in FIG. 1A, Bit1 transfection produced a profound change in cell morphology; the cells rounded up within a few hours of transfection and were essentially all detached from the culture dish when photographed 48 hours after transfection. Furthermore, HEK 293 cells were transfected with a Bcl-2-promoter-luciferase reporter construct together with increasing amounts of Bit1 expression construct; Bcl-2 transcription was measured by quantifying luciferase fluorescence after 24 hours in culture. In agreement with the CHO cell results, transcription from the Bcl-2 promoter was suppressed in the Bit1-transfected HEK 293 cells (see FIG. 1B). A DNA fragmentation assay revealed a DNA ladder typical of apoptosis, and annexin V-fluorescein isothiocyanate/propidium iodide (FITC/PI) staining confirmed that the Bit1-mediated cell death was apoptotic (see FIGS. 1C and 1D, respectively). In particular, the percentages of annexin V-positive cells (lower right quadrants) are about 1.4% in the control and about 4.7% in the Bit1-transfected cells. Late stage apoptosis, revealed by both annexin V and propidium iodide uptake (upper right quadrants), was also greater in the Bit1-transfected cells (7% versus 18%).

Figure 2:
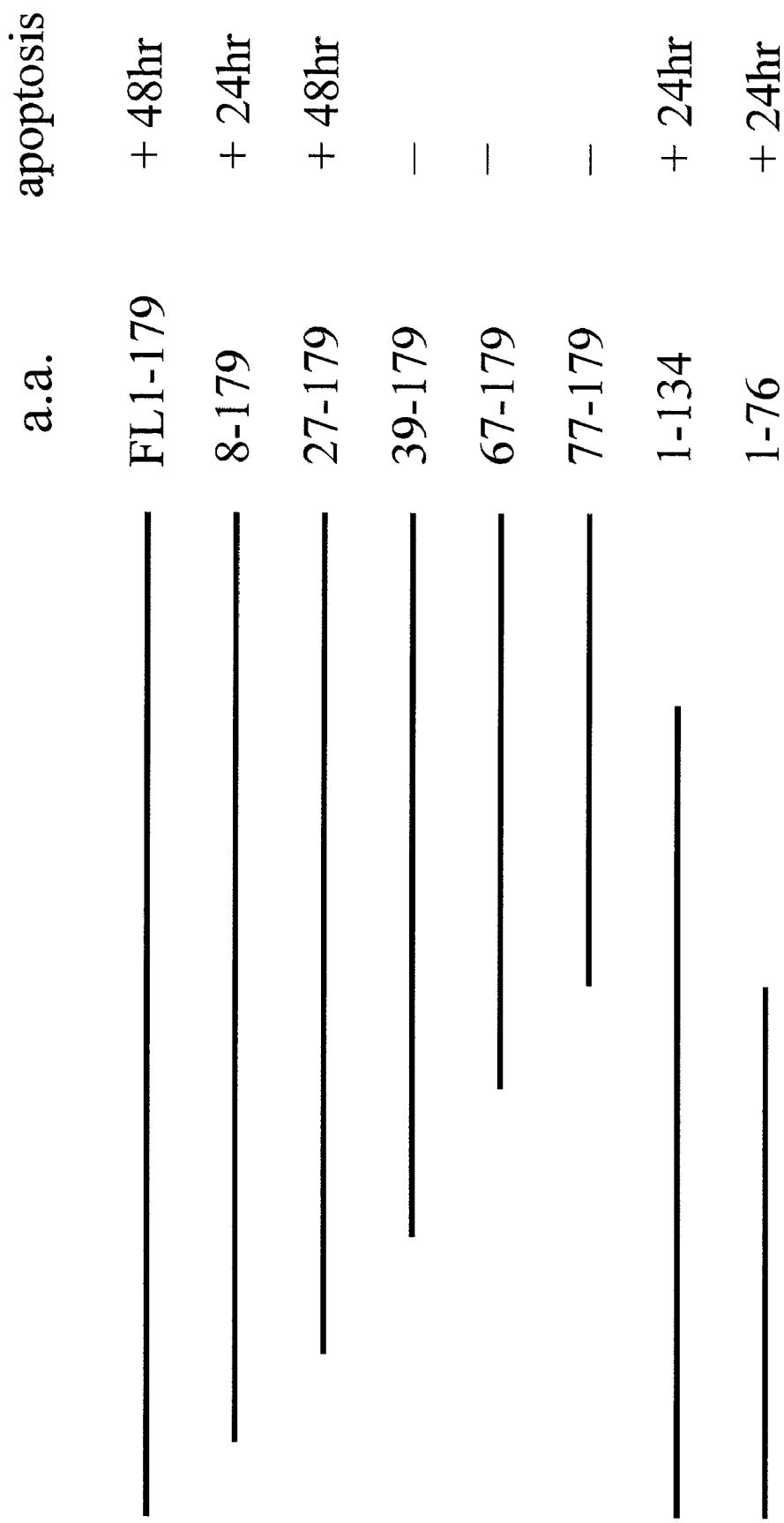
FIG. 2 shows pro-apoptotic activity of various Bit1 deletion mutants in CHO cells. A schematic of the Bit1 construct is shown in the left column. Bit1 residues present in the deletion construct are shown in the middle column. Cell death (right column) was measured by trypan blue exclusion 48 hours after transfection.

The amino-terminal portion of Bit1 (residues 16-40) is hydrophobic and can serve as a transmembrane domain or signal peptide sequence. When the hydrophobicity of this portion was reduced by substitution of glycine 22 and glycine 38 by serine, Bit1 apoptotic activity was reduced. Furthermore, as shown in FIG. 2, deletion of 26 amino-terminal residues of Bit1 did not affect pro-apoptotic activity. However, in agreement with activity of the truncated Bit1 clone isolated in the screening, deletion of 38 amino-terminal residues abolished the pro-apoptotic effect (see FIG. 2). In contrast, a large C-terminal deletion or deletion of the amino-terminal seven residues of Bit1 accelerated pro-apoptotic activity, indicating that the first few amino-terminal residues and the carboxy-terminal portion of Bit1 can serve as negative regulatory domains (see FIG. 2). Together with the results disclosed above, these results indicate that full-length Bit1 inhibits Bcl-2 transcription and induces apoptosis, whereas amino-terminally truncated forms of Bit1 can have dominant negative activity.

Cell culture and transfection were performed as follows. CHO-B2/α5ΔCβ1 cells (Zhang et al., *Proc. Natl. Acad. Sci. USA.* 92:6161-6165 (1995); Bauer et al., *J. Cell. Biol.* 116: 477-487 (1992); and Schreiner et al., *J. Cell. Biol.* 109:3157-3167 (1989)) were maintained in tissue culture plates in alpha modified Eagle's medium supplemented with 10% fetal bovine serum, glutamine/penicillin-streptomycin and 250 μg/ml G418. Hela and 293T cells were cultured in Dulbecco's modified Eagle's medium (DMEM) with glutamine containing 10% fetal bovine serum and penicillin-streptomycin. Cells were plated 18 hours prior to transfection, which was performed with FuGene6 (Roche; Basel, Switzerland) according to the manufacturer's protocol.

Expression cloning was performed as follows. CHO-B2/α5ΔCβ1 cells were plated on fibronectin under serum free conditions. Cells were co-transfected using lipofectAMINE (Gibco-BRL; Carlsbad, Calif.) with Bcl2-EGFP, a human fetal brain cDNA library in pcDNAI, and pPSVE1-PYE, which encodes the polyoma large T antigen. After 48 hours, transfected cells were monodispersed using an enzyme-free cell dissociation solution (Hank's based; Cell and Molecular Technology; Lavallette, N.J.) followed by sterile cell sorting of Bcl-2-EGFP positive cells. Plasmids from the sorted cells were isolated by the Hirt procedure and amplified in the host bacteria *E. coli* MC1061/P3 in the presence of ampicillin and tetracycline. Amplified plasmids were divided into 20 plates. Plasmids prepared from each of the 20 plates were transfected separately into CHO-B2 cells. Transfectants were screened by FACS analysis to identify a plasmid pool that directed the expression of the Bcl-2-EGFP construct. After five rounds of sibling selection, single clones containing the plasmid DNA encoding a human cDNA that directed the expression of Bcl-2-EGFP were isolated.

Analysis of cell viability and apoptosis was performed as follows. Cell viability was measured by trypan blue exclusion analysis. Apoptosis was confirmed by DNA fragmentation (Oncogene; La Jolla, Calif.) thirty-six hours after transfection. Annexin-V staining (BD Biosciences Clontech; Palo Alto, Calif.) was performed according to the manufacturer's protocol.

Deletion analysis was performed as follows. The indicated deletion mutants were cloned into vector pEGFP-C1, and 10 μg of each plasmid construct transfected into CHO cells. Cell death was measured by trypan blue exclusion 48 hours after transfection.

EXAMPLE II

Bit1 Interacts with the Groucho-Related Protein, AES

This example demonstrates that the Groucho-related protein, AES, can bind Bit1.

To explore the mechanism whereby Bit1 induces cell death, a yeast-two-hybrid screening assay was performed to search for binding partners for the Bit1 protein. Full-length Bit1 cDNA was fused to the Gal4 DNA-binding domain in the pGBKT7 vector and used as bait; a human fetal brain cDNA expression library fused to the Gal4 transcriptional activation domain was screened in cells expressing the Bit1/GAL4 DNA-binding domain fusion. Approximately one million transformants from the cDNA library were screened, and about 100 clones positive for both nutritional selection and α-galactosidase activity were obtained. Nucleotide sequence determination and comparison with the GenBank database (National Center for Biotechnology Information) revealed thirty clones that encoded human AES.

AES is approximately 5.0% identical to the amino-terminal region of the *Drosophila* protein Groucho. Groucho and its mammalian homologues, TLE (transducin-like enhancer of split) proteins, are developmentally regulated transcriptional co-repressors that do not themselves bind DNA. AES, the shortest member of the Groucho/TLE family, lacks the "WD-40" protein interaction domain present in longer Groucho/TLE proteins and can serve as a negative regulator of TLE functions. AES also can have gene regulatory activity independent of other Groucho/TLE proteins (Chen and Courey, *Gene* 249:1-16 (2000); and Fisher and Caudy, *Genes Dev.* 12:1931-1940 (1998)).

As shown in FIG. 3A, yeast grew when co-transformed with vectors encoding both Bit1 and AES, indicating an interaction between the two proteins. The ability of AES to interact with Bit1 was confirmed in mammalian cells.

As shown in FIG. 3B, co-immunoprecipitation of exogenously expressed Bit1 and AES confirmed interaction between these proteins. Tagged Bit1 and AES were transfected into cells, and cell extracts were immunoprecipitated with anti-flag and immunoblotted with anti-myc. Equal loading of the samples was confirmed by immunoblotting of the whole extract with anti-flag.

In contrast with this observation using exogenously expressed Bit1, endogenous Bit1 and AES did not detectably co-precipitate from attached HeLa cell extracts. However, endogenbus Bit1/AES complexes were detected when release of Bit1 from mitochondria into the cytoplasm was initiated by culturing the cells in suspension. To confirm that Bit1 released from mitochondria in suspended cells is capable of interacting with AES, HeLa cells were cultured in suspension for 24 hours to initiate apoptosis and cause the release of Bit1 from mitochondria. The cell extracts were immunoprecipitated with agarose-immobilized anti-Bit1 antibody and immunoblotted with anti-AES. FIG. 3C shows that C-terminally myc-tagged Bit1, which is sequestered in mitochondria, did not form complexes with AES in intact cells, but did so in suspended cells.

In another experiment to confirm that cytoplasmic Bit1 interacts with AES in cells, HeLa cells were transfected with C-terminally myc-tagged Bit1 together with flag-tagged AES and 24 hours later grown for another 24 h either attached or in suspension. Cell extracts were prepared and immunoprecipitated with anti-flag. The precipitates were immunoblotted with anti-myc. The whole cells extracts were immunoblotted with anti-myc or anti-flag as loading controls. The results of this experiment, shown in FIG. 3D, indicate that cytoplasmic Bit1 interacts with AES in cells.

To determine if Bit1 and AES are both required for apoptosis induction, HEK 293T, HOP92, and CHO cells were transfected with a GFP (vector), GFP-Bit1, or GFP-AES fusion protein constructs, as indicated in FIG. 3E. The cells were examined 48 hours (HEK 293T and CHO) or 72 hours (HOP92) after transfection, and the percentage of GFP-positive detached cells was measured. As shown in FIG. 3E, AES transfection induced apoptosis in CHO cells, but had no effect on the viability of the 293T cells, even though these cells responded to Bit1 transfection.

Because the HEK 293T cells lack detectable Bit1 activity, it seemed possible that AES required endogenous Bit1 for the pro-apoptotic activity. An NIH data bank identified HOP92 as a cell line that expresses only negligible amounts of AES. Significantly, these cells were resistant to Bit1-induced apoptosis. CHO cells (FIG. 3E) and HeLa cells, which express both Bit1 and AES, underwent apoptosis upon transfection with either protein. These results indicate that the transfected Bit1 and AES biologically interact with the endogenous AES and Bit1, respectively.

Yeast two-hybrid screening was performed as follows. Full length CGI-147 was cloned in-frame with the Gal4 DNA binding domain in vector pGBKT7 and used to screen a yeast two-hybrid library derived from human fetal brain (Clontech). Yeast strain AH109 was co-transformed with PGBKT7-Bit1, pACT-2-AES or both, and growth selected in SD medium -ADE/-His/-Leu/-Trp and assayed for α-galactosidase activity according to the manufacturer's instructions (Clontech).

Immunoprecipitation and immunoblotting were performed essentially as follows. Cells were transfected with full-length clones for Bit1 and AES, which were obtained by PCR from EST clones using Pfu enzyme (Stratagene; La Jolla, Calif.) and cloned into pCMV-Myc (Clontech) or pCMV-flag (Sigma; St. Louis, Mo.). After 24 to 48 hours, cells were harvested in ice-cold NP-40 lysis buffer (1% NP-40; 20 mM Tris-HCl, pH 7.4; 150 mM NaCl; 10% glycerol, 2 mM sodium vanadate; 1 mM phenylmethyl sulfonylfluoride; 10 µg/ml leupeptin; and 5 µg/ml aprotinin) and lysed at 4° C. for 15 minutes. Lysates were incubated for two hours with the indicated antibodies, and the antibody complexes precipitated with 20 µl of Gammabind (Amersham-Pharmacia; Piscataway, N.J.) for an additional hour. After washing the beads, bound proteins were solubilized in SDS-PAGE sample buffer. Western blot analysis was performed according to standard procedures.

These results indicate that Bit1 and AES physically interact in vivo in mammalian cells.

EXAMPLE III

AES is Part of a Bit1 Apoptotic Pathway

This example demonstrates that AES enhances Bit1-mediated apoptosis.

AES was assayed for pro-apoptotic activity in CHO cells transfected with a green fluorescent protein (GFP)-AES fusion protein. As seen in FIG. 4A, CHO cells receiving AES, as indicated by GFP fluorescence, died within 48 hours. GFP fluorescence (right panels) showed that the rounded-up cells predominantly were cells expressing AES. However, in HEK 293 cells, which express no detectable Bit1 by immunohistochemistry or Northern analysis, transfection of AES alone was not apoptotic. These results indicate that AES pro-apoptotic activity requires co-expression of Bit1.

Furthermore, apoptosis was measured in cells transfected with Bit1 (5 µg DNA), AES (5 µg DNA) or both (5 µg each). Rounded up cells expressing GFP were scored as dead cells 24 and 48 hours after the transfection. As shown in FIG. 4B, co-transfection of AES with Bit1 accelerated apoptosis in CHO cells, resulting in nearly complete death of doubly transfected cells within 24 hours.

To delineate the pro-apoptotic domain of AES, a series of AES deletion mutants was prepared as amino-terminal fusions with GFP in vector pEGFP-C1. Various AES deletion constructs (10 µg) were transfected into CHO cells, and cell death measured by trypan blue exclusion 48 hours after transfection. As summarized in FIG. 5, a construct expressing AES residues 57-105 or residues 57-88 efficiently induced apoptosis in CHO cells, whereas constructs encompassing residues 1-56 or 106-197 had no apoptotic activity. These results indicate that residues 57-105 or residues 57-88 are sufficient for AES pro-apoptotic activity.

EXAMPLE IV

TLE1 Blocks AES-Induced Apoptosis

This example demonstrates that AES-induced cell death is blocked by TLE1 co-expression.

To determine if TLE1 suppresses apoptosis induced by AES in CHO cells, cells were transfected with GFP-AES or GFP-TLE1 alone, or both. Cell death was assessed by scoring rounded-up cells expressing GFP 48 hours later. As is shown in FIG. 6A, transfection of CHO with a TLE1 expression vector or both TLE1 and AES expression vectors together reduced apoptosis.

To determine if Bit1-AES association is reduced in HEK 293T cells transfected with TLE1, HEK 293T cells were transfected with plasmids encoding myc-Bit1, flag-AES or GFP-TLE1 as indicated in FIG. 6B. Cell lysates were harvested 24 hours after transfection and subjected to immunoprecipitation with anti-flag and immunoblotting with anti-myc.

In agreement with the ability of fibronectin attachment to prevent apoptosis induced by Bit1 or AES, immunoprecipitation experiments also reveals less Bit1-AES complex in HeLa cells plated on fibronectin than on collagen (FIG. 6C). In these experiments, HeLa cells were plated on fibronectin or collagen before transfection with pCMV-Myc-Bit1 (3 µg) and pCMV-flag-AES (3 µg) plasmids. Cell lysates were harvested 24 h after transfection and immunoprecipitated with anti-flag and immunoblotted with anti-myc. The total amount of DNA used was adjusted to 10 µg with empty vector in each transfection. The expression of the transfected AES in each sample was confirmed by immunoblotting 20 µl of the whole extract with anti-flag as is shown in FIG. 6C, lower boxes in B and C.

Quantification of the gel bands in FIG. 6C showed that the reduction in Bit1/AES complex on fibronectin was approximately 75%. Controls indicated that HeLa cells express higher levels of collagen receptors than of $\alpha_5\beta_1$. Thus, a low level of Bit1/AES complex correlated with cell survival and a high level is associated with apoptosis. FIG. 6D shows that TLE2 modestly suppresses apoptosis induced by AES in CHO cells.

These results confirm the ability of Bit1/AES to induce apoptosis, and demonstrate that TLE1 antagonizes apoptosis resulting from activation of the Bit1/AES pathway.

EXAMPLE V

Bit1/AES Pathway Down-Regulates HSP-70 and Thymosin 54

This example demonstrates that HSP-70 and thymosin 54 are down-regulated by expression of Bit1 or AES.

To determine whether the Bit1/AES pathway can regulate the transcription of genes other than Bcl-2, two stable cell lines were established expressing either-Bit1 or AES under control of an ecdysone-inducible promoter. To detect genes regulated by Bit1 or AES, probes were prepared from the ecdysone-induced cell lines and used to screen microarrays representing 19,000 human cDNAs. Analysis of total RNA isolated 36 hours after induction with ecdysone revealed two additional anti-apoptotic proteins, HSP-70 and thymosin β4, which were down-regulated by both Bit1 and AES (Table 1). Down-regulation of HSP-70 and thymosin 4 in cells induced to express Bit1 or AES was confirmed by Northern blot analysis (see FIG. 7). In contrast, Bcl-2 expression was not measurably altered in the Bit1 and AES stable cell lines.

HSP-70 and thymosin β4 are known anti-apoptotic proteins. HSP-70 suppresses apoptosis by preventing recruitment of pro-caspase-9 to the Apaf-1 apoptosome, and antagonizes apoptosis-inducing factor (AIF), which is part of a caspase-independent apoptosis pathway (Beere et al., *Nat. Cell. Biol.* 2:469-475 (2000); and Ravagnan et al., *Nat. Cell. Biol.* 3:839-843 (2001)). Down-regulation of HSP-70 can activate a tumor-specific death program (Nylandsted et al., *Proc. Natl. Acad. Sci. USA* 97:7871-7876 (2000)). Thymosin β4, an actin binding protein present at high concentrations in many vertebrate tissues and cell lines, also can suppress apoptosis (Niu and Nachmias, *Cell Adhes. Commun.* 7:311-320 (2000)) and enhance metastasis (Clark et al., *Nature* 406:532-535 (2000)).

TABLE 1

| Microarray result | Gene | UniGene number | Northern result |
|---|---|---|---|
| Suppressed by Bit1* | Heat Shock 70 kD protein 1A | Hs.8997 | 3 fold |
| | Thymosin β-4 | Hs.75968 | 5 fold |
| | Actin-binding LIM protein | Hs.158203 | |
| | sialytransferase | Hs.107573 | |
| Induced by Bit1* | Tissue factor pathway inhibitor 2 | Hs.78045 | |
| | Atrophin-1 interacting protein 1 | Hs.22599 | |
| | Mannosyl (β-1,4)-glycoprotein β-1,4-N-acetylglucosaminyltransferase | Hs.112 | |
| | insulin-like growth factor-binding protein-4 | Hs.1516 | |
| Suppressed by AES* | Heat shock 70 KD protein 1A | Hs.8997 | 3 fold |
| | Thymosin β-4 | Hs.75968 | 4 fold |
| | KCNAB2 | Hs.154417 | |
| | FLJ10386 | Hs.236556 | |
| | NET-5 | Hs.129826 | |
| | SRY-related HMG-box gene 4 | Hs.83484 | |
| Induced by AES* | DNA replication licensing factor MCM5 | Hs.77171 | |
| | NIK-related kinase 17 | Hs.112028 | |
| | CMP-N-acetylneuraminic acid synthase 12 | Hs.12492 | |

*At least a two-fold suppression or induction was observed cDNA microarray analysis was performed as follows. Total RNA was purified 48 hours after treatment with 10 μM ponasterone A (Invitrogen; San Diego, Calif.) from the ecdysone inducible cell line ECR-293-Bit1 or ECR-293-AES according to the manufacturer's instructions (Qiagen; Valencia, Calif.). cDNA probes were generated and hybridized with a microarray containing 19,000 human cDNAs from Microarray Centre at University Health Network, Ontario Cancer institute. cDNAs were labeled with fluorescent dyes (Cy3 or Cy5) using reverse transcription. Arrays were processed and hybridized essentially as described in Iyer et al., *Science* 283:83-87 (1999). After hybridization, arrays were scanned to measure fluorescence using a ScanArray 4000 scanner (Perkin Elmer; Meriden, Conn.). Raw data files generated by scanner software were imported into ImaGene and Gene Spring for analysis. Experiments were performed in duplicate using color reversals.

Northern blot analysis was performed as follows. Total RNA (10 μg) was electrophoresed on a 1% agarose-formaldehyde gel and transferred to nitrocellulose filters. The filters were hybridized using the same RNA probes as in the microarray experiments in Rapid-hyb buffer and washed according to the manufacturer's instructions (Amersham-Pharmacia).

EXAMPLE VI

Cell Attachment and PI3K Regulate Bit1-Induced Apoptosis

This example demonstrates that Bit1 is part of a cell-attachment regulated cell death pathway.

Several extracellular matrix proteins were assayed for the ability to modulate Bit1-mediated apoptosis. Cells were plated onto bacterial culture dishes pre-coated overnight with fibronectin (Chemicon; Temecula; CA), vitronectin (SIGMA; St. Louis, Mo.) or type I collagen (SIGMA), and transfected and assayed for apoptosis as described above. As shown in FIG. 8A, HEK 293 cells plated onto dishes coated with fibronectin (FN) or vitronectin (VN) were largely protected from Bit1-induced apoptosis. In contrast, collagen (Col) could not confer the same protective effect.

Dominant negative R-Ras and an activated form of H-Ras, both of which are negative regulators of integrin activity, also were assayed for the ability to modulate Bit1-mediated apoptosis. FIG. 8B shows that dominant negative R-Ras and activated H-Ras each enhanced the apoptosis-inducing effect of Bit1. Dominant negative FAK (FRNK) also enhanced the pro-apoptotic effect of Bit1. These results indicate that integrin-mediated cell attachment can regulate the Bit1 pathway, thereby preventing apoptosis, and that detachment of cells and inactivation of integrins can enhance the pro-apoptotic effects of Bit1.

To analyze integrin involvement in protecting attached cells against the pro-apoptotic effect of Bit1, Bit1 cell lines expressing either α5β1 or αvβ1 as the main fibronectin receptor were compared. The two cell lines attach equally well to fibronectin but, like cytoplasmically truncated α5β1, αvβ1 fails to protect cells against apoptosis induced by serum deprivation (Zhang et al., supra, 1995; and Matter and Ruoslahti, supra, 2001). As shown in FIG. 8C, CHO-B2-α5β1 cells that attached to fibronectin were protected from Bit1-induced apoptosis, whereas CHO-B2-αvβ1 cells were not. As further shown in FIG. 5D, function-blocking anti-α5 μl integrin antibodies eliminated the protective effect of fibronectin attachment against Bit1-induced apoptosis in HEK 293 cells, but did not detectably influence the attachment of the cells to fibronectin. In sum, these results indicate that the α5β1 integrin initiates signals capable of blocking Bit1-induced apoptosis.

HEK 293 cells also were co-transfected with Bit1 and an activated form of PI3K, or Bcl-2 or Bcl-xL or one of various caspase inhibitors (XIAP, p35 or CrmA). However, each of these proteins had little or no effect on apoptosis induced by Bit1 (see FIG. 8E). To confirm that constructs with no effect on Bit1 apoptosis were functional, apoptosis was also induced via Fas (0.5 μg or Bax (0.25 μg). The same proteins were assayed in CHO cells transfected with AES. The activated form of PI3K partially suppressed AES-induced apoptosis in CHO cells; however, the other transfected proteins were inactive.

To determine whether Bit1-induced apoptosis is caspase-dependent, cell lysates from Bit1-transfected 293T cells were tested for poly (ADP-ribose) polymerase (PARP) cleavage. Results from these experiments indicated no increase of 85-kD PARP apoptotic fragment in the lysates, indicating lack of caspase activation. 293T cells were also co-transfected with Bit1 or AES and the caspase inhibitor proteins crmA and XIAP. As shown in FIG. 8F, CrmA and XIAP had no effect on apoptosis induced by either Bit1 or AES. A chemical pan-caspase inhibitor, z-VAD-fmk, was also ineffective against Bit1 and AES. In addition, Bcl-2 and Bcl-xL had no effect on cytosolic Bit1-induced apoptosis, but were partially effective against AES. Constitutively activated PI3-K (p110) and AKT also suppressed AES-induced cell death, but were ineffective in Bit1, suggesting a mitochondrial target for their activity. The unique ability of integrin-mediated cell attachment to reverse Bit1-induced apoptosis provides evidence that Bit1 functions in anoikis.

The role of Bit1 in the tendency of detached cells to undergo apoptosis (anoikis in the strictest sense) was then examined. HEK 293T cells were transfected with C-terminally myc-tagged (mitochondrial) Bit1 or with empty vector, and the cells were cultured either on tissue-culture plates (attached) or on poly-HEMA (detached) for 48 hours. The number of attached cells ($10^6$) was the same whether the cells were transfected with Bit1 or vector (assigned as 100% in FIG. 8H). In detached cultures, Bit1 significantly reduced the number of surviving cells (30% reduction vs. 8% in the vector transfection).

As is shown in FIG. 8H, Bit1 and control transfected cells had the same level of spontaneous apoptosis when grown attached to a culture dish. In striking contrast, detachment induced a higher level of cell death in the Bit1-transfected cells than in the control cells. Given that the transfection efficiency was about 50-70% in the 293T cells, the nearly 4-fold higher apoptosis level of the Bit1-transfected cells translates into more than 5-fold difference in anoikis sensitivity. These results, and the results documenting the ability of the α5β1 integrin to protect cells against the pro-apoptotic activity of Bit1 and AES, provide evidence that the Bit1/AES pathway plays a role in integrin-dependent cell survival.

Experiments with extracellular matrix proteins were performed as follows. Cells were plated onto uncoated tissue culture plates or onto bacterial culture plates coated with fibronectin, vitronectin or collagen, and allowed to attach in the presence of serum. The attachment was equal on all of these surfaces. The cells were then transfected with 10 μg of Bit1 expression plasmid; where indicated, cells were treated with a control IgG of unrelated specificity or monoclonal anti-human α5 antibody (Chemicon), both at 10 μg/ml. Cell death was measured by trypan blue staining 48 hours after the transfection.

Co-transfections were performed with cells plated on non-coated dishes transfected with 5 μg Bit1 plasmid alone or together with 10 μg dominant negative (DN) R-Ras, or activated H-Ras plasmid (Zou et al., *Proc. Natl. Acad. Sci. USA* 96: 13813-13818 (1999)). Cells were transfected as described above with expression constructs pcDNA3-Bcl-2, Bcl-xL, p35, CrmA or XIAP provided by Dr. Guy Salvesen (The Burnham Institute), and described in Ryan et al., Immediate publication, *DOI* 10:1042/BJ20020863 (2002); Deveraux et al., *EMBO J.* 18:5242 (1999); and Cardone et al., *Science* 282: 1318 (1998). Expression of the transfected proteins was confirmed by immunoblotting. Apoptosis was assayed as described above.

EXAMPLE VII

Bit1 Tissue Distribution

This example describes Bit1 mRNA expression in a variety of human tissues.

To develop an understanding as to the tissues in which the new Bit1/AES regulatory pathway can be active, Bit1 tissue distribution was studied by Northern blot analysis performed as described above using multiple tissue Northern blots purchased from Clontech. Blots were probed with $^{32}$P-labeled full-length Bit1 or AES cDNA, and actin mRNA was detected as a loading control. As shown in FIG. 9, a single Bit1 transcript of about 1 kilobase was observed in human tissues. Bit1 mRNA was prominent in testis, prostate, skeletal muscle, and liver tissue, with the heart, ovaries, placenta and colon expressing intermediate levels of Bit1 mRNA. No significant Bit1 mRNA signal was seen in thymus and peripheral leukocytes. A similar expression pattern was observed for AES, with expression particularly high in the prostate and skeletal muscle, two tissues also expressing high levels of Bit1.

Bit1 and AES expression also were analyzed in a variety of established cell lines. With the exception of HEK 293 cells, Bit1 expression was detected in the other cell lines tested by Northern blotting, immunohistochemical staining, or both. AES also was widely expressed in various cell lines; a panel of 80 malignant cell lines revealed only one cell line with marginal AES expression. The broad expression profiles of Bit1 and AES indicate that the Bit1/AES apoptosis-regulating pathway is active in many tissues and cell types.

EXAMPLE VIII

Localization of Bit1 in Mitochondria

This example describes Bit1 polypeptide expression in mitochondria.

Figure 12:
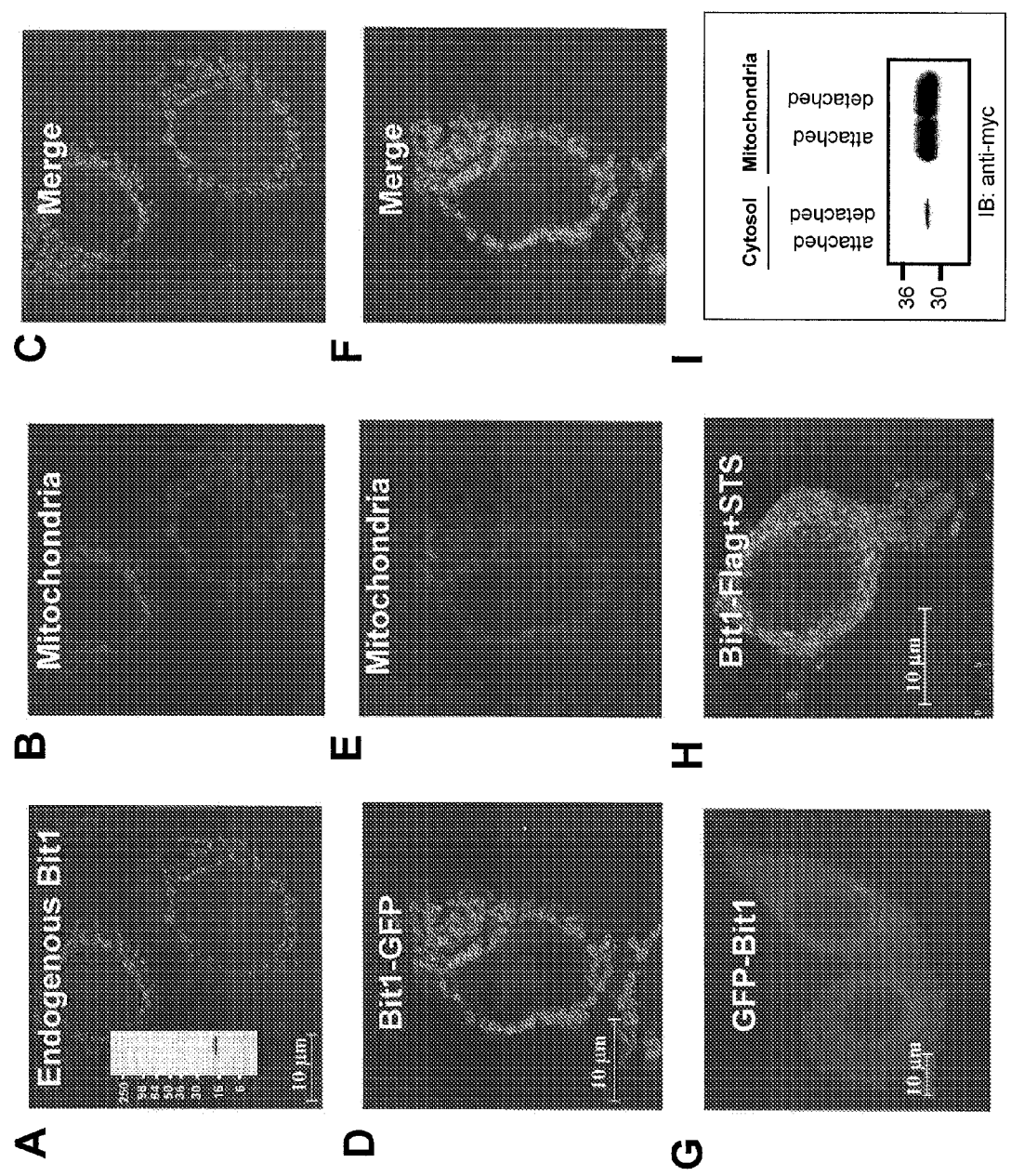
FIG. 12 shows that Bit1 is localized in mitochondria. (A-C) Immunostaining of endogenous Bit1. HeLa cells were transfected with the mitochondrial marker plasmid, pDsRed2-Mito, and stained with anti-Bit1 antibody 24 hours later. Photographs were taken under a confocal microscope to visualize Bit1 (panel A) or mitochondria (panel B). A merge of the two fluorescence images is shown in panel C. The inset in A shows immunoblotting of HeLa mitochondrial extract with the anti-Bit1 antibody used in panels A-C: (D-F) C-terminally GFP tagged Bit1 is localized in mitochondria. HeLa cells were co-transfected with Bit1-GFP and pDsRed2-Mito plasmids and photographed 24 hours later to visualize the proteins as indicated. (G) N-terminally tagged Bit1 is expressed in the cytoplasm. HeLa cells were transfected with GFP-Bit1 and photographed 24 hours later. (H) Bit1-flag transfected into HeLa cells localizes in mitochondria, but is released into the cytoplasm in cells induced to undergo apoptosis with 0.5 µM staurosporin (STS). (I) Cytoplasmic Bit1 in suspended cells. HEK 293T cells were transfected with C-terminally myc-tagged Bit1 and 24 hours later, the cells were left attached or plated on poly-HEMA coated plates to maintain a cell suspension. After 12 h, cell lysates were prepared, separated into cytosolic and mitochondrial (heavy membrane) fractions, run on SDS gels and immunoblotted with an anti-myc antibody.

To confirm that Bit1 polypeptide is expressed in mitochondria, HeLa cells were transfected with the mitochondrial marker plasmid, pDsRed2-Mito, and stained with anti-Bit1 antibody 24 hours later. Photographs were taken under a confocal microscope to visualize Bit1 (FIG. 12, panel A) or mitochondria (FIG. 12, panel B). A merge of the two images is shown in panel C. The anti-Bit1 antibody used in the immunofluorescence experiment detected Bit1 in HeLa mitochondrial extract, as shown by Western blotting (inset FIG. 12A)

To determine if a C-terminally GFP tagged Bit1 is localized in mitochondria, HeLa cells were co-transfected with Bit1-GFP and pDsRed2-Mito plasmids and photographed 24 hours later. Photographs were taken under a confocal microscope to visualize Bit1 (FIG. 12, panel D) or mitochondria (FIG. 12, panel E). A merge of the two images is shown in panel F. These results indicate that C-terminally tagged Bit1 is localized in mitochondria.

To determine if an N-terminally GFP tagged Bit1 is localized in mitochondria, HeLa cells were co-transfected with GFP-Bit1 and pDsRed2-Mito plasmids and photographed 24 hours later to visualize the proteins. FIG. 12 (panel G) shows that N-terminally tagged Bit1 is expressed in the cytoplasm and not in mitochondria. This result indicates that the N-terminal GFP tag disrupts the mitochondrial localization signal of the Bit1 polypeptide.

FIG. 12 (panel H) shows that C-terminally tagged Bit1 transfected into HeLa cells localizes in mitochondria, but is released into the cytoplasm in cells induced to undergo apoptosis with 0.5 μM staurosporin (STS). Colocalization of Bit1 with an endoplasmic reticulum or golgi marker was not observed.

Localization of Bit1 further was examined in suspended cells. HEK 293T cells were transfected with C-terminally myc-tagged Bit1 and 24 hours later, the cells were left attached or plated on poly-HEMA coated plates to maintain a cell suspension. After 12 hours, cell lysates were prepared, separated into cytosolic and mitochondrial (heavy membrane) fractions, run on SDS gels and immunoblotted with an anti-myc antibody. As is shown in FIG. 12 (panel I) Bit1 expression in the cytosol could be detected only when cells where detached.

Cell lysates were prepared as follows. HEK 293T cells were transfected with 8 μg of expression plasmid for c-terminal myc-tagged Bit1 or vector DNA, and 24 hours later the cells were left attached or plated on poly-HEMA coated plates and maintained in suspension for 12 hours. The cells were then washed once with PBS and $10^7$ cells were resuspended in 1 ml of isotonic mitochondrial buffer (250 mM mannitol, 70 mM sucrose, 1 mM EDTA, 10 mM Hepes, pH 7.5), homogenized with 40 strokes in a Dounce homogenizer. The lysates were centrifuged at 500×g for 5 min to eliminate nuclei and unbroken cells and the supernatant was further centrifuged at 10,000×g for 30 min at 4° C. The mitochondria-enriched pellet was resuspended in 50 up of isotonic mitochondrial buffer. The cytosolic supernatant and the mitochondrial fraction were fractionated on SDS-PAGE for subsequent immunoblot analysis.

EXAMPLE IX

Bit1 and AES Down-Regulate Bcl-1 Promoter Activity

This example describes that Bit1 and AES down-regulate Bcl-2 promoter activity, while TLE1 enhances Bcl-2 promoter activity.

Figure 13:
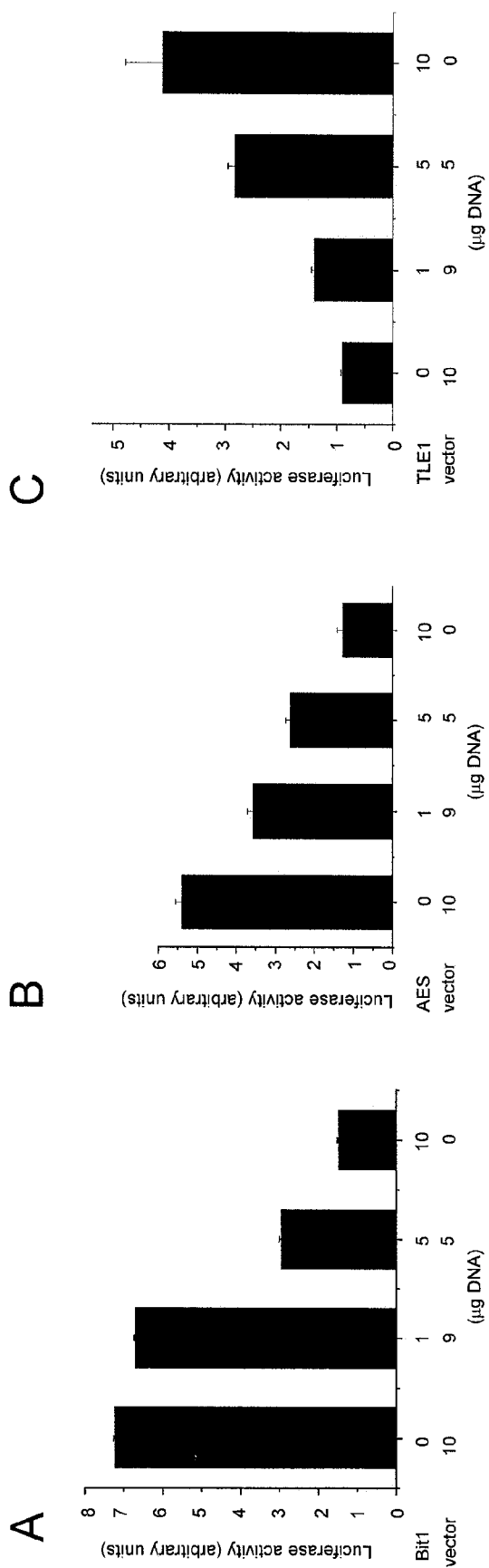
FIG. 13 shows that Bit1 and AES reduce Bcl-2 promoter activity, while TLE1 increases Bcl-2 promoter activity. CHO cells were transfected with 1 µg Bcl-2-luciferase reporter construct together with the indicated amounts (µg) of (A) Bit1, (B) AES, or (C) TLE1 expression vectors, and Bcl-2 transcription was measured by quantifying luciferase fluorescence after 24 hours in culture.

To determine the effect of Bit1, AES, and TLE1 on Bcl-2 promoter activity, CHO cells were transfected with 1 μg Bcl-2-luciferase reporter construct together with Bit1, AES, or TLE1 expression vectors, as shown in FIG. 13, and Bcl-2 transcription was measured by quantifying luciferase fluorescence after 24 hours in culture.

As is shown in FIG. 13, Bit1 and AES down-regulate Bcl-2 promoter activity whereas TLE1 enhances it. These results are in agreement with the ability of Bit1/AES to induce apoptosis, and for TLE1 to inhibit apoptosis.

All journal article, reference and patent citations provided above, in parentheses or otherwise, whether previously stated or not, are incorporated herein by reference in their entirety.

Although the invention has been described with reference to the examples provided above, it should be understood that various modifications can be made without departing from the spirit of the invention. Accordingly, the invention is limited only by the claims.

We claim:

1. A method of identifying an effective agent that modulates cell death, comprising the steps of:
   (a) contacting a cell containing an exogenous nucleic acid molecule encoding a Bit1 (Bcl-2 inhibitor of transcription) polypeptide or active fragment thereof with an agent, wherein said Bit1 polypeptide or active fragment thereof is selected from SEQ ID NO:2, a polypeptide comprising residues 8-179 of SEQ ID NO:2, a polypeptide comprising residues 27-179 of SEQ ID NO:2, a polypeptide comprising residues 1-134 of SEQ ID NO:2, a polypeptide comprising residues 1-76 of SEQ ID NO:2, and a polypeptide comprising residues 27-76 of SEQ ID NO:2, wherein said cell expresses an AES (amino enhancer of split) polypeptide or active fragment thereof and wherein said AES polypeptide or active fragment thereof is selected from a polypeptide comprising SEQ ID NO:6, a polypeptide comprising residues 57-105 of SEQ ID NO:6, a polypeptide comprising residues 57-88 of SEQ ID NO:6, a polypeptide comprising residues 1-157 of SEQ ID NO:6, a polypeptide comprising residues 1-132 of SEQ ID NO:6, a polypeptide comprising residues 1-104 of SEQ ID NO:6, a polypeptide comprising residues 56-197 of SEQ ID NO:6, and a polypeptide comprising residues 56-104 of SEQ ID NO:6; and
   (b) detecting an increase or decrease in cell death relative to a cell in the absence of said agent, said increase or decrease in cell death indicating that said agent is an effective agent that modulates cell death.

2. The method of claim 1, wherein said AES polypeptide is an exogenous AES polypeptide or active fragment thereof.

3. The method of claim 1, wherein said cell is a mammalian cell.

4. The method of claim 1, wherein increased cell death is detected.

5. The method of claim 1, wherein decreased cell death is detected.

6. The method of claim 1, wherein step (b) comprises detecting cell death using an assay selected from the group consisting of trypan blue exclusion, thymidine uptake, deoxytransferase-mediated (TdT) dUTP biotin nick end-labeling (TUNEL), digoxygenin labeling, and a DNA filter elution assay.

7. The method of claim 1, wherein said Bit1 polypeptide or active fragment thereof is SEQ ID NO:2.

8. The method of claim 1, wherein said Bit1 polypeptide or active fragment thereof is a polypeptide comprising residues 8-179 of SEQ ID NO:2.

9. The method of claim 1, wherein said Bit1 polypeptide or active fragment thereof is a polypeptide comprising residues 27-179 of SEQ ID NO:2.

10. The method of claim 1, wherein said Bit1 polypeptide or active fragment thereof is a polypeptide comprising residues 1-134 of SEQ ID NO:2.

11. The method of claim 1, wherein said Bit1 polypeptide or active fragment thereof is a polypeptide comprising residues 1-76 of SEQ ID NO:2.

12. The method of claim 1, wherein said Bit1 polypeptide or active fragment thereof is a polypeptide comprising residues 27-76 of SEQ ID NO:2.

13. The method of claim 1, wherein said AES polypeptide or active fragment thereof is a polypeptide comprising SEQ ID NO:6.

14. The method of claim 1, wherein said AES polypeptide or active fragment thereof is a polypeptide comprising residues 57-105 of SEQ ID NO:6.

15. The method of claim 1, wherein said AES polypeptide or active fragment thereof is a polypeptide comprising residues 57-88 of SEQ ID NO:6.

16. The method of claim 1, wherein said AES polypeptide or active fragment thereof is a polypeptide comprising residues 1-157 of SEQ ID NO:6.

17. The method of claim 1, wherein said AES polypeptide or active fragment thereof is a polypeptide comprising residues 1-132 of SEQ ID NO:6.

18. The method of claim 1, wherein said AES polypeptide or active fragment thereof is a polypeptide comprising residues 1-104 of SEQ ID NO:6.

19. The method of claim 1, wherein said AES polypeptide or active fragment thereof is a polypeptide comprising residues 56-197 of SEQ ID NO:6.

20. The method of claim 1, wherein said AES polypeptide or active fragment thereof is a polypeptide comprising residues 56-104 of SEQ ID NO:6.

21. A method of identifying an effective agent that modulates apoptosis, comprising the steps of:
   (a) contacting a cell containing an exogenous nucleic acid molecule encoding a Bit1 (Bcl-2 inhibitor of transcription) polypeptide or active fragment thereof and a Bcl-2 promoter with an agent, wherein said Bit1 polypeptide or active fragment thereof is selected from SEQ ID NO:2, a polypeptide comprising residues 8-179 of SEQ ID NO:2, a polypeptide comprising residues 27-179 of SEQ ID NO:2, a polypeptide comprising residues 1-134 of SEQ ID NO:2, a polypeptide comprising residues 1-76 of SEQ ID NO:2, and a polypeptide comprising residues 27-76 of SEQ ID NO:2; and
   (b) detecting an increase or decrease in Bcl-2 expression level relative to a cell in the absence of said agent, said increase or decrease in Bcl-2 level indicating that said agent is an effective agent that modulates apoptosis.

22. The method of claim 21, wherein said cell expresses an AES (amino enhancer of split) polypeptide or active fragment thereof, wherein said AES polypeptide or active fragment thereof is selected from a polypeptide comprising SEQ ID NO:6, a polypeptide comprising residues 57-105 of SEQ ID NO:6, a polypeptide comprising residues 57-88 of SEQ ID NO:6, a polypeptide comprising residues 1-157 of SEQ ID NO:6, a polypeptide comprising residues 1-132 of SEQ ID NO:6, a polypeptide comprising residues 1-104 of SEQ ID NO:6, a polypeptide comprising residues 56-197 of SEQ ID NO:6, and a polypeptide comprising residues 56-104 of SEQ ID NO:6.

23. The method of claim 22, wherein said AES polypeptide is an exogenous AES polypeptide or active fragment thereof.

24. The method of claim 21, wherein said Bcl-2 level is increased.

25. The method of claim 21, wherein said Bcl-2 level is decreased.

26. The method of claim 21, wherein said Bcl-2 promoter is operably linked to a reporter gene.

27. The method of claim 26, wherein said reporter gene is selected from the group consisting of luciferase, green fluorescent protein and β-galactosidase.

28. The method of claim 21, wherein said Bit1 polypeptide or active fragment thereof is SEQ ID NO:2.

29. The method of claim 21, wherein said Bit1 polypeptide or active fragment thereof is a polypeptide comprising residues 8-179 of SEQ ID NO:2.

30. The method of claim 21, wherein said Bit1 polypeptide or active fragment thereof is a polypeptide comprising residues 27-179 of SEQ ID NO:2.

31. The method of claim 21, wherein said Bit1 polypeptide or active fragment thereof is a polypeptide comprising residues 1-134 of SEQ ID NO:2.

32. The method of claim 21, wherein said Bit1 polypeptide or active fragment thereof is a polypeptide comprising residues 1-76 of SEQ ID NO:2.

33. The method of claim 21, wherein said Bit1 polypeptide or active fragment thereof is a polypeptide comprising residues 27-76 of SEQ ID NO:2.

34. The method of claim 22, wherein said AES polypeptide or active fragment thereof is a polypeptide comprising SEQ ID NO:6.

35. The method of claim 22, wherein said AES polypeptide or active fragment thereof is a polypeptide comprising residues 57-105 of SEQ ID NO:6.

36. The method of claim 22, wherein said AES polypeptide or active fragment thereof is a polypeptide comprising residues 57-88 of SEQ ID NO:6.

37. The method of claim 22, wherein said AES polypeptide or active fragment thereof is a polypeptide comprising residues 1-157 of SEQ ID NO:6.

38. The method of claim 22, wherein said AES polypeptide or active fragment thereof is a polypeptide comprising residues 1-132 of SEQ ID NO:6.

39. The method of claim 22, wherein said AES polypeptide or active fragment thereof is a polypeptide comprising residues 1-104 of SEQ ID NO:6.

40. The method of claim 22, wherein said AES polypeptide or active fragment thereof is a polypeptide comprising residues 56-197 of SEQ ID NO:6.

41. The method of claim 22, wherein said AES polypeptide or active fragment thereof is a polypeptide comprising residues 56-104 of SEQ ID NO:6.

* * * * *